United States Patent
Daugulis et al.

(10) Patent No.: US 8,114,993 B2
(45) Date of Patent: Feb. 14, 2012

(54) USE OF ARYL CHLORIDES IN PALLADIUM-CATALYZED C-H BOND FUNCTIONALIZATION

(75) Inventors: Olafs Daugulis, Houston, TX (US); Hendrich Chiong, Evansville, IN (US)

(73) Assignee: The University of Houston System, Houston, TX (US)

( * ) Notice: Subject to any disclaimer, the term of this patent is extended or adjusted under 35 U.S.C. 154(b) by 940 days.

(21) Appl. No.: 12/027,029

(22) Filed: Feb. 6, 2008

(65) Prior Publication Data
US 2009/0012293 A1    Jan. 8, 2009

Related U.S. Application Data

(60) Provisional application No. 60/888,471, filed on Feb. 6, 2007, provisional application No. 60/888,488, filed on Feb. 6, 2007.

(51) Int. Cl.
*C07D 487/06* (2006.01)
(52) U.S. Cl. ...................................................... 544/262
(58) Field of Classification Search .................... 544/262
See application file for complete search history.

(56) References Cited

OTHER PUBLICATIONS

Thompson et al., J. Chem. Soc. (1945) pp. 640-645.*

* cited by examiner

*Primary Examiner* — Taofiq A Solola
(74) *Attorney, Agent, or Firm* — Robert W Strozier

(57) ABSTRACT

A one-step method for efficiently converting carbon-hydrogen bonds into carbon-carbon bonds using chloroarenes and palladium catalysts is disclosed. This method allows faster introduction of complex molecular entities, a process that would otherwise require many more steps. This invention is particularly relevant for the organic synthesis of complex molecules such as, but not limited to, pharmacophores.

28 Claims, 72 Drawing Sheets

Entry 1, Table I

Entry 1, Table I
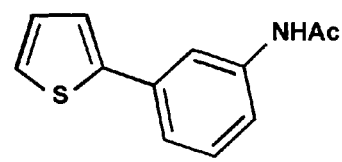
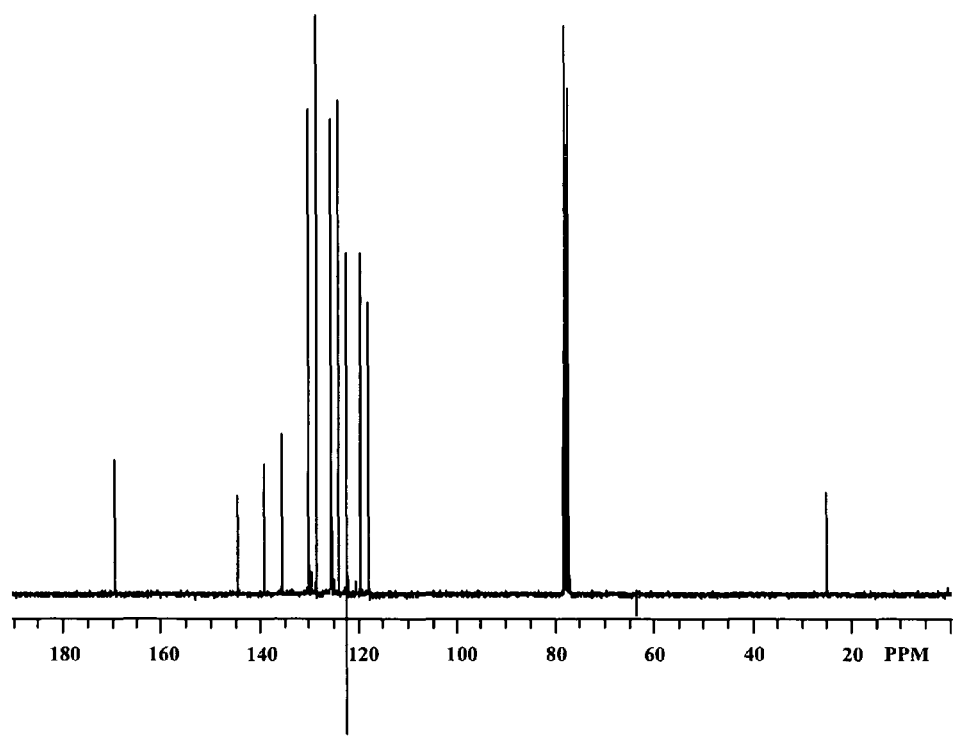
FIG. 3B

Entry 2, Table I

Entry 2, Table I

Entry 3, Table I

Entry 4, Table I

Entry 5, Table I

Entry 6, Table I

Entry 7, Table I

Entry 7, Table I

Entry 8, Table I

Entry 9, Table I

Entry 10, Table I

Entry 11, Table I

Entry 11, Table I

Entry 13, Table I

Entry 13, Table I

Entry 13, Table I

Entry 14, Table I

Entry 15, Table I

Entry 15, Table I

Entry 16, Table I

Entry 16, Table I

Entry 17, Table I

Entry 1, Table II
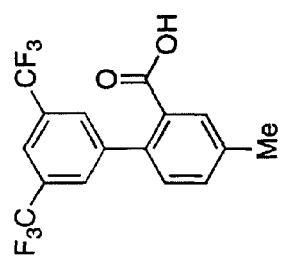
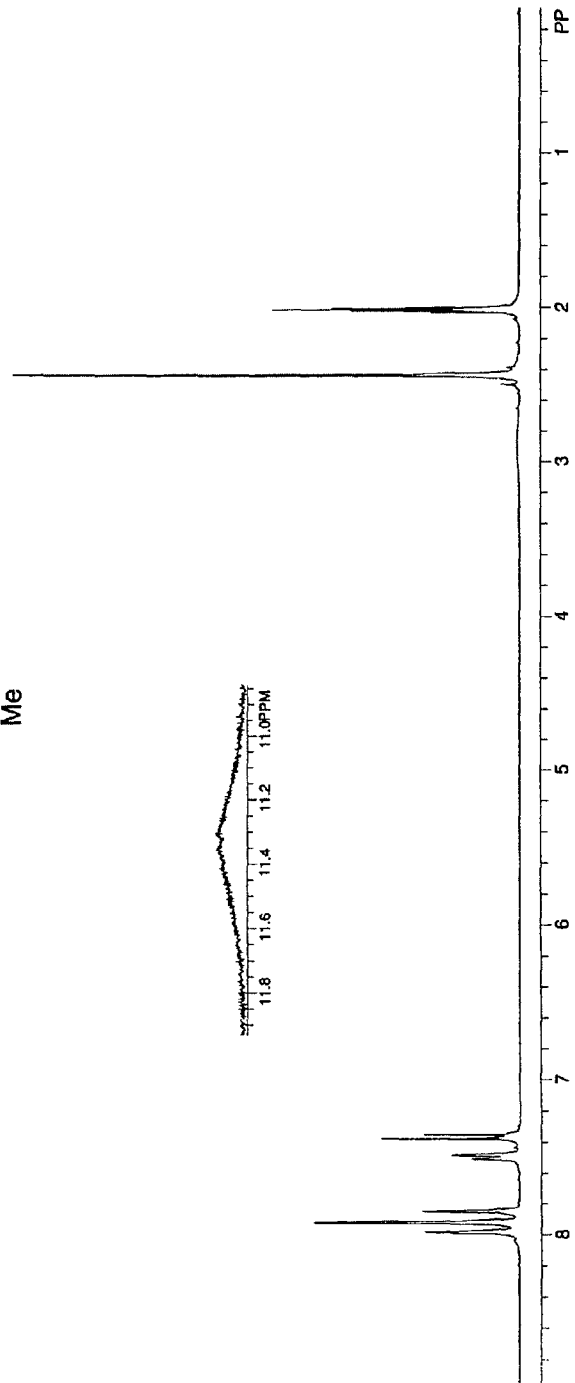
FIG. 24A

Entry 1, Table II

Entry 2, Table II
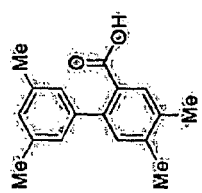
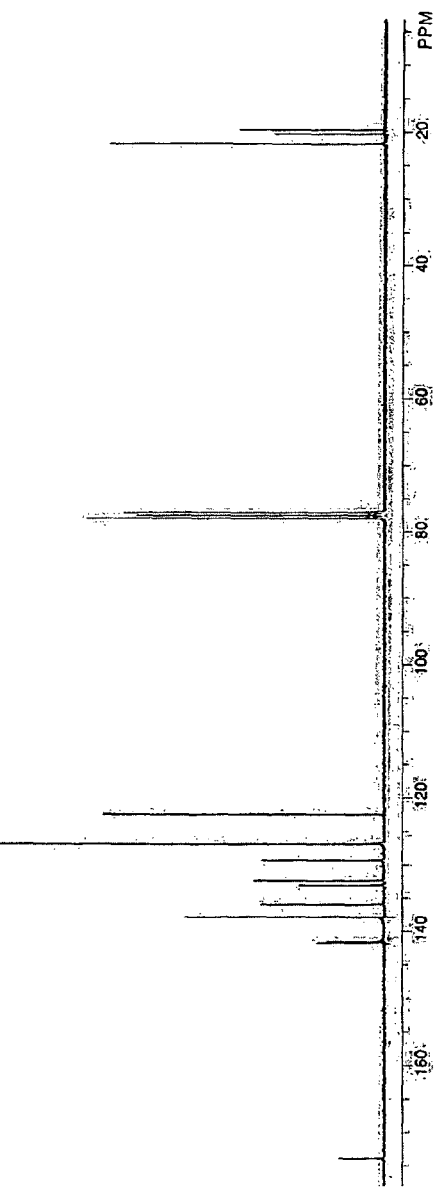
FIG. 25B

Entry 3, Table II

Entry 3, Table II
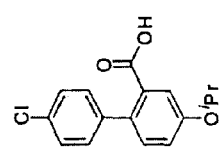
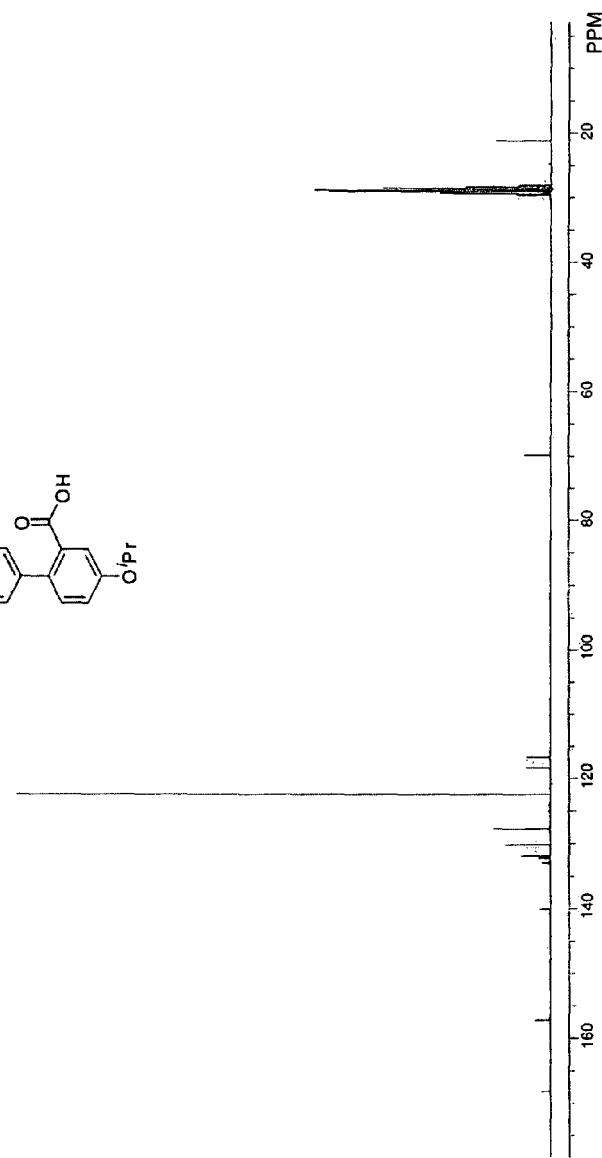
FIG. 26B

Entry 4, Table II

Entry 4, Table II
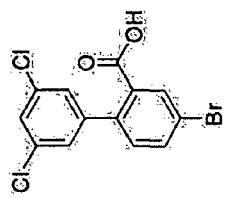
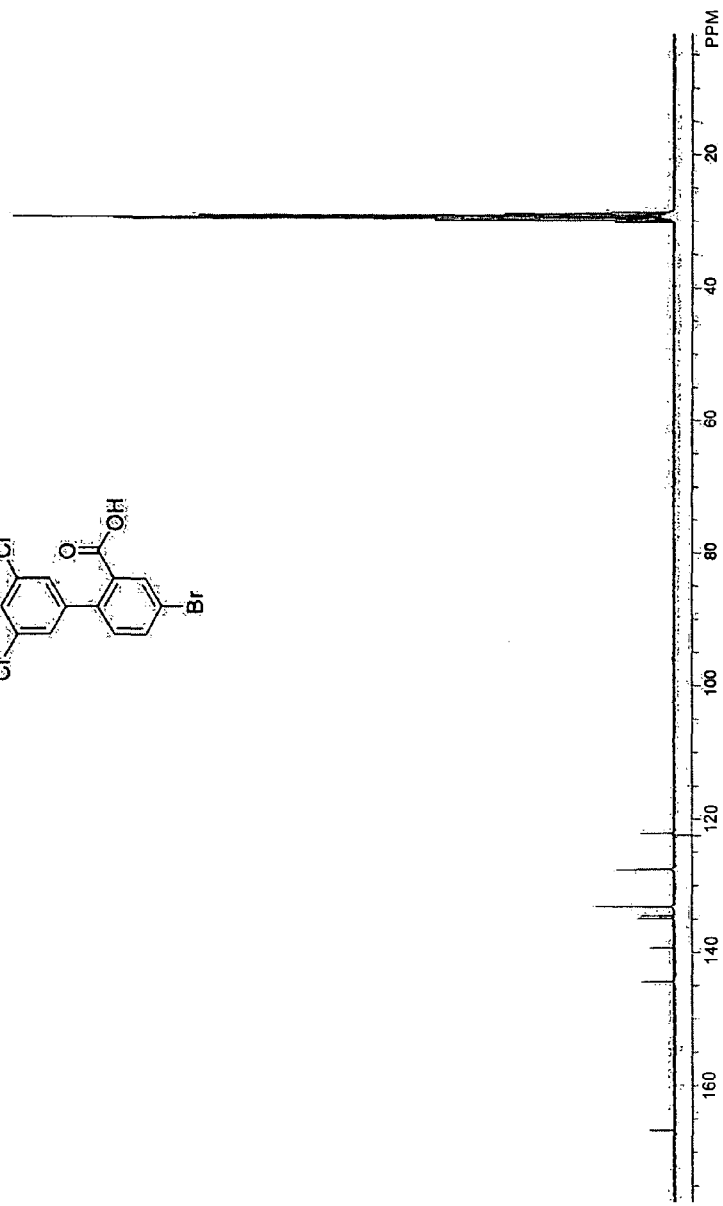
FIG. 27B

Entry 5, Table II

Entry 5, Table II

Entry 6, Table II

Entry 6, Table II

Entry 7, Table II

Entry 1, Table III

Entry 1, Table III

Entry 2, Table III

Entry 2, Table III

Entry 3, Table III

Entry 3, Table III

Entry 4, Table III
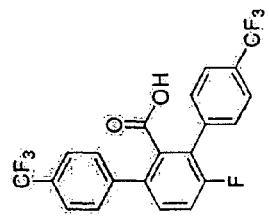
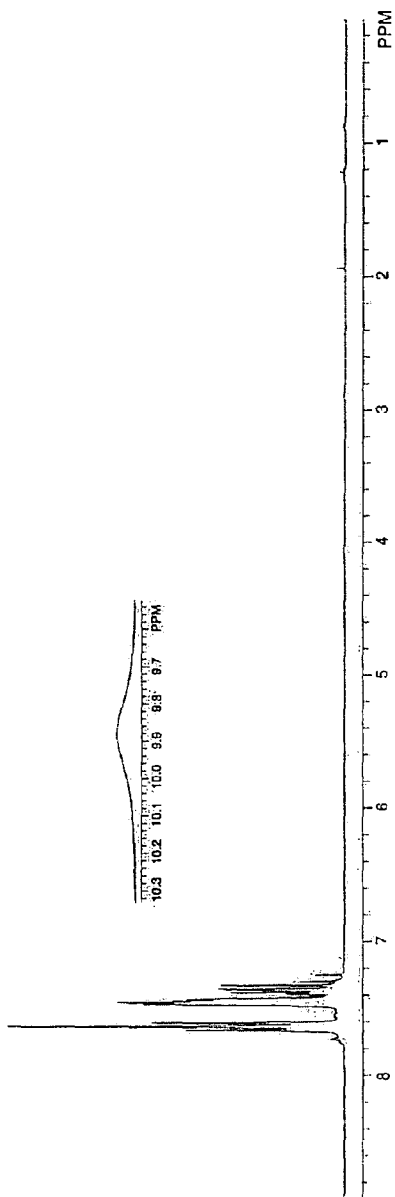
FIG. 34A

Entry 4, Table III

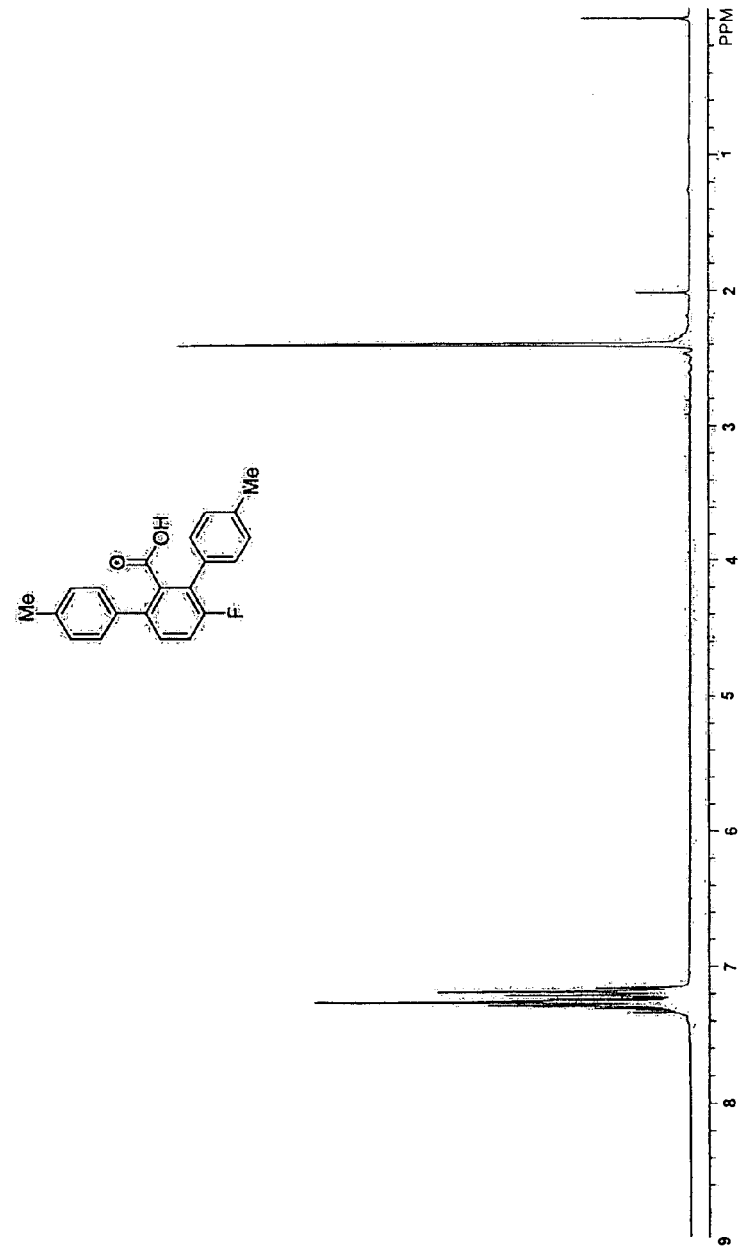

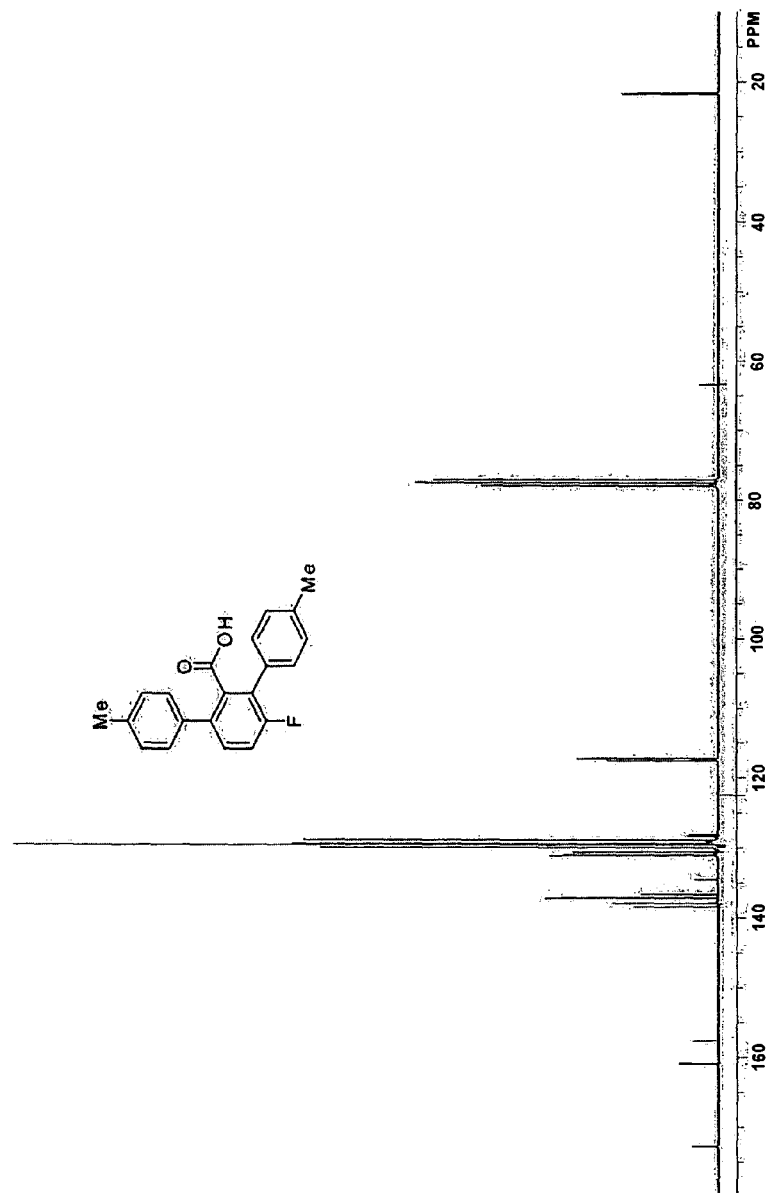

Entry 6, Table III

Entry 7, Table III
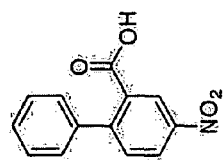
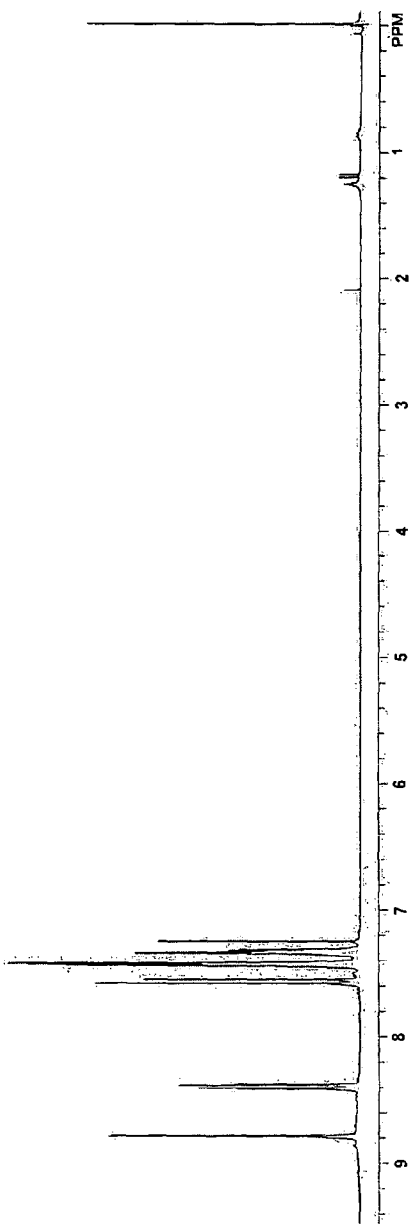
FIG. 37

Entry 8, Table III

Entry 9, Table III
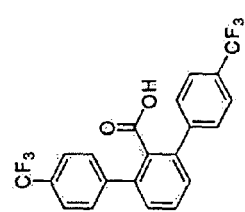
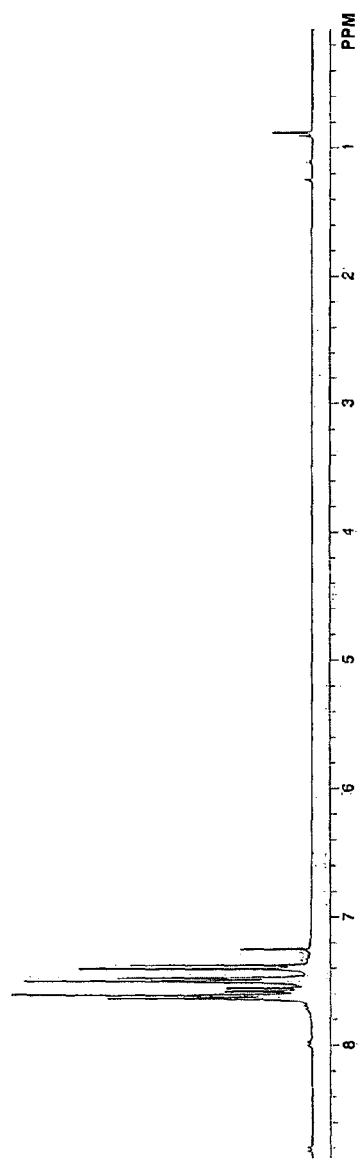
FIG. 39A

Entry 9, Table III

Entry 10, Table III
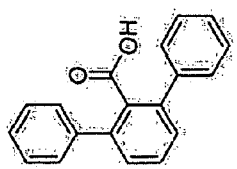
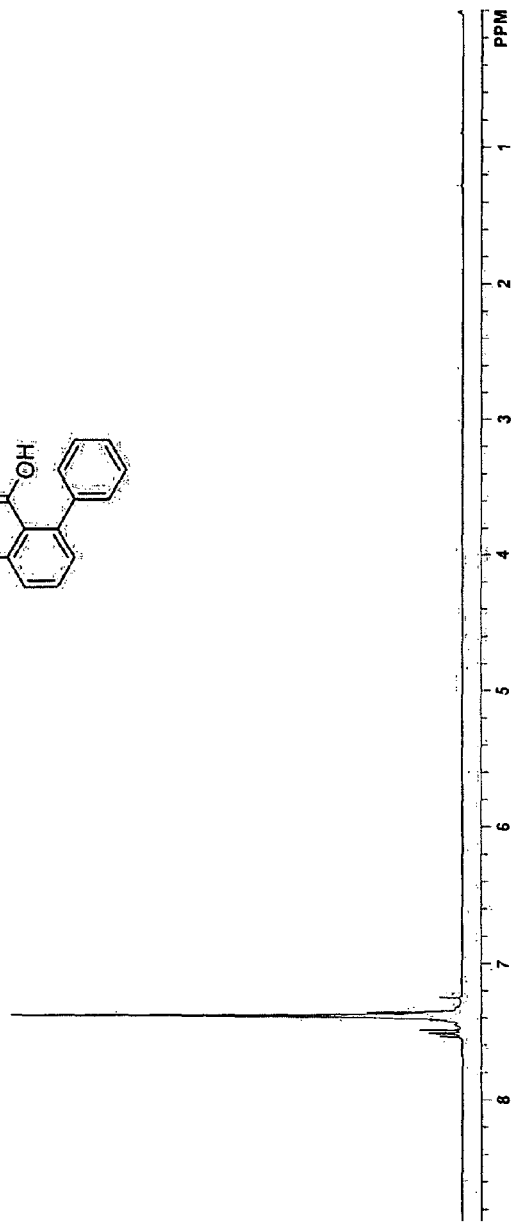
FIG. 40

Entry 11, Table III

Entry 11, Table III

Entry 11, Table III

Entry 12, Table III

Entry 13, Table III

Entry 13, Table III
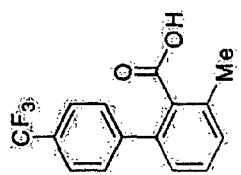
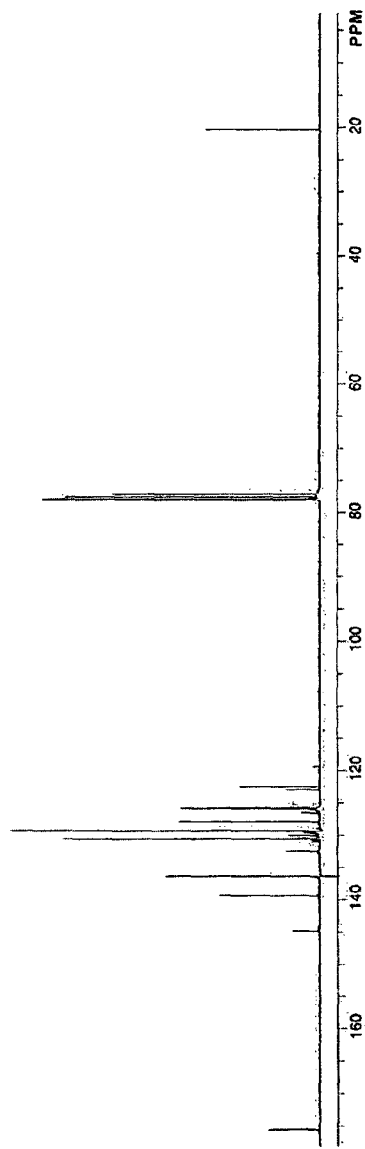
FIG. 44B

Entry 14, Table III

Entry 14, Table III
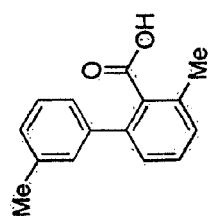
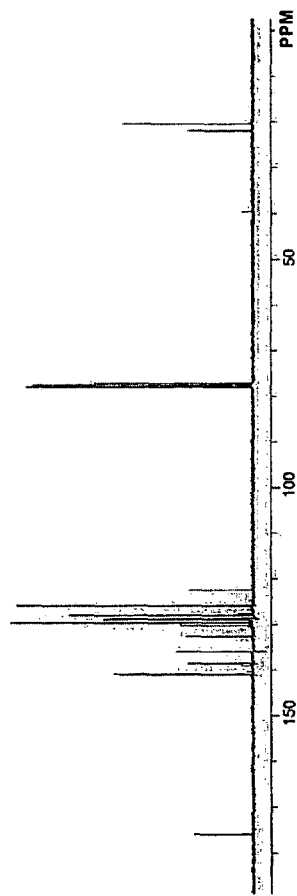
FIG. 45B

USE OF ARYL CHLORIDES IN PALLADIUM-CATALYZED C-H BOND FUNCTIONALIZATION

RELATED APPLICATIONS

This application claims priority to and the benefit of U.S. Provisional Patent Application Ser. Nos. 60/888,471 filed Feb. 6, 2007 and 60/888,488 filed Feb. 6, 2007, incorporated herein by reference.

GOVERNMENTAL SPONSORSHIP

National Science Foundation under Award Number DMR-9632667

BACKGROUND OF THE INVENTION

1. Field of the Invention

The present invention relates generally to a new method for the formation of carbon-carbon bonds and to compounds made by the method.

More specifically, the invention relates to a one-step method for converting carbon-hydrogen bonds into carbon-carbon bonds using a palladium catalyst and to compounds made by the method.

2. Description of the Related Art

The formation of carbon-carbon (C—C) bonds is perhaps one of the most important reactions inorganic chemistry and is commonly used for the synthesis of most molecules. Currently, the most developed methods for forming carbon-carbon double bonds involve transition-metal catalyzed cross-coupling reactions between Ar-M (Ar=aryl group and M=$SnR_3$, $B(OR)_2$ (O=oxygen and R=hydrogen or alkyl group), MgX) and Ar—X (X=halogen or sulfonate). Quite often these functionalized starting materials are either expensive or have to be prepared in several steps.

To overcome this problem, it is necessary to achieve the regioselective conversion of carbon-hydrogen (C—H) to C—C bonds. This chemical approach results in the shortening of many synthetic schemes.

Thus, there is a need in the art for forming C—C bonds through chemically modifying intermolecular electron-rich heterocycles, benzoic acids, and phenols by aryl chlorides for rapid introduction of molecular entities through C—C bond formation. This method considerably shortens organic synthetic schemes involving electron rich heterocycles, benzoic acids, and phenols and allows the use of cheap aryl chlorides for their transformations.

SUMMARY OF THE INVENTION

The present invention provides a method for a one-step intermolecular arylation of electron-rich, five-membered heterocycles, benzoic acids, and phenols, where the method includes the step of contacting one or a plurality of electron-rich, five-membered heterocycles, benzoic acids, and/or phenols with one or a plurality of aryl chlorides in the presence of a palladium catalyst solution for a time and at a temperature to product arylated heterocycle, arylated benzoic acid and/or arylated phenol products. This method affords cheaper and faster method for forming complex molecular entities, shortening many synthetic schemes.

The present invention also provides a one-step method including the step of contacting one or a plurality of electron-rich, five-membered heterocycles with one or a plurality of aryl chlorides in the presence of a palladium catalyst solution for a time and at a temperature to product arylated heterocycle, arylated benzoic acid and/or arylated phenol products. This method affords cheaper and faster method for forming complex molecular entities, shortening many synthetic schemes.

The present invention also provides a one-step method including the step of contacting one or a plurality of benzoic acids with one or a plurality of aryl chlorides in the presence of a palladium catalyst solution for a time and at a temperature to product arylated heterocycle, arylated benzoic acid and/or arylated phenol products. This method affords cheaper and faster method for forming complex molecular entities, shortening many synthetic schemes.

The present invention also provides a one-step method including the step of contacting one or a plurality of phenols with one or a plurality of aryl chlorides in the presence of a palladium catalyst solution for a time and at a temperature to product arylated heterocycle, arylated benzoic acid and/or arylated phenol products. This method affords cheaper and faster method for forming complex molecular entities, shortening many synthetic schemes.

All of the methods set forth above can also include the step of isolating the product and/or purifying the product. All of the methods can also include the step of optimizing the reaction conditions, catalyst, base, promoters and solvents to maximize the yield of a desired compound.

BRIEF DESCRIPTION OF THE DRAWINGS

The invention can be better understood with reference to the following detailed description together with the appended illustrative drawings in which like elements are numbered the same:

FIG. 3B depicts a $^{13}$C NMR spectrum of Entry 1 of Table I.

FIG. 24A depicts a $^1$H NMR spectrum of Entry 1 of Table II.

FIG. 25B depicts a $^{13}$C NMR spectrum of Entry 2 of Table II.

FIG. 26B depicts a $^{13}$C NMR spectrum of Entry 3 of Table II.

FIG. 27B depicts a $^{13}$C NMR spectrum of Entry 4 of Table II.

FIG. 34A depicts a $^1$H NMR spectrum of Entry 4 of Table III.

FIG. 35A depicts a $^1$H NMR spectrum of Entry 5 of Table III.

FIG. 35B depicts a $^{13}$C NMR spectrum of Entry 5 of Table III

FIG. 37 depicts a $^1$H NMR spectrum of Entry 7 of Table III.

FIG. 39A depicts a $^1$H NMR spectrum of Entry 9 of Table III.

FIG. 40 depicts a $^1$H NMR spectrum of Entry 10 of Table III.

FIG. 44B depicts a $^{13}$C. NMR spectrum of Entry 13 of Table III.

FIG. 45B depicts a $^{13}$C NMR spectrum of Entry 14 of Table III.

DETAILED DESCRIPTION OF THE INVENTION

The inventors have found

Figure 1:
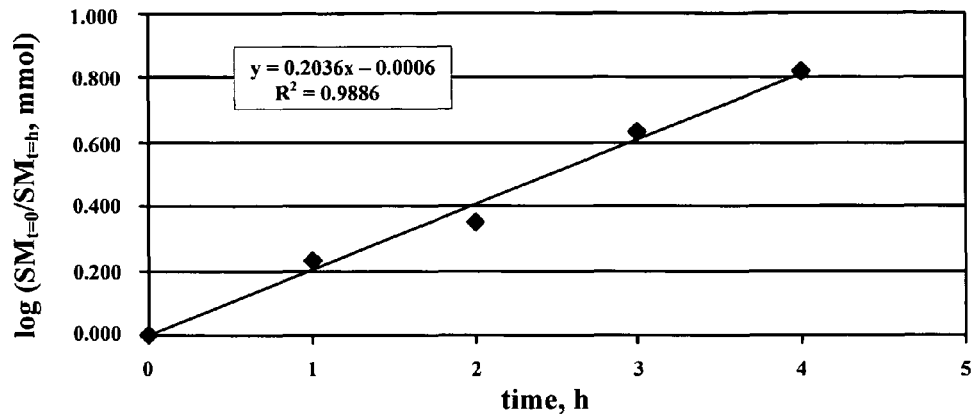
FIG. 1 depicts a graph of the reaction of 2-H-benzothiazole with PhCl versus time (h).

The present invention broadly relates to a method for the efficient formation of carbon-carbon bonds through the intermolecular arylation of electron-rich, five-membered heterocycles, benzoic acids, and phenols by aryl chlorides in the presence of a palladium catalyst. This method allows faster formation of complex molecular entities, a process that would otherwise require many more steps. This invention is particularly relevant for the organic synthesis of complex molecules such as, but not limited to, pharmacophores.

In one embodiment, the present invention includes a general procedure for the coupling of chloroarene with heterocyclic compounds according to Formula (I):

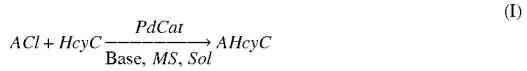

(I)

$$ACl + HcyC \xrightarrow[\text{Base, MS, Sol}]{\text{PdCat}} AHcyC$$

where A is are aryl group (A-Cl is an arene chloride or a chloro-arene), HcyC is a heterocyclic compound, PdCat is a palladium catalyst, Base is an inorganic base, MS is a molecular sieve and Sol is a solvent system. In certain embodiments, multiple aylations can occur to produce compounds of the general formula $(A)_n HcyC$, where A and HcyC are as previously defined and n is an integer between 2 and the maximum number of aryl group the HryC can accommodate. In other embodiments, n is between 2 and 4. In other embodiments, n is between 2 and 3. In other embodiments, n is 2. The reaction are generally performed at an elevated temperature. In certain embodiments, the elevated temperatures is sufficient to facilitate product formation, but not so high as to cause decomposition of the starting materials or products. In other embodiments, the temperature is between about 90° C. and about 160° C. In other embodiments, the temperatures is between about 100° C. and about 150° C. In other embodiments, the temperatures is between about 100° C. and about 140° C. In certain embodiments, the time is a period sufficient to achieve a desired conversion to product at a desired temperature. In other embodiments, the period of time is between about 30 minutes and about 24 hours. In other embodiments, the period of time is between about 1 hour and about 18 hours. In other embodiments, the period of time is between about 1 hour and about 12 hours. In other embodiments, the period of time is between about 2 hours and about 12 hours. In other embodiments, the period of time is between about 4 hours and about 12 hours. In other embodiments, the period of time is between about 6 hours and about 12 hours.

Although inmost embodiments arylchlorides are the preferred halogenated aryl for arylation using the method of this invention, other halogens can be use as well including bromine and iodine.

The general reaction conditions for the reaction (I) are: 5 mol % Pd(OAc)$_2$, 2 equiv Cs$_2$CO$_3$, MS 3 Å, dry DMF, stir for 15 min at RT then for 16 h at 125° C. Reactions were performed in 2-dram vials with PTFE caps. Outside the glovebox, a 2-dram vial equipped with a magnetic stir bar is charged with Pd(OAc)$_2$ (5 mol %), heterocycle (1.0 mmol) and chloroarene (1.5 equiv). The vial is flushed with argon, capped and placed inside a glovebox. To this mixture is added butyldi-1-adamantylphosphine (10 mol %), K$_3$PO$_4$ (2.0 equiv) and anhydrous N-methylpyrrolidinone (4 mL). The sealed vial is taken out of the glovebox, stirred at room temperature for 15 min and placed in a preheated oil bath (125° C.) for 24 h. The reaction mixture is cooled to room temperature and quenched with 1% aqueous KOH (10 mL). Resulting suspension is extracted with dichloromethane (3×5 mL) and the organic layer filtered through a pad of Celite®. The filtrate is concentrated under vacuum to a volume of about 2 mL. The mixture is absorbed on silica gel and subjected to flash chromatography. After concentration of the fraction, the residue is dried under reduced pressure (usually at 40° C.) to yield pure arylated heterocycle.

Oxidative addition of ArCl to palladium Pd$^0$ usually requires a bulky, electron-rich phosphine, secondary phosphine oxide, an N-heterocyclic carbene, or mixtures or combinations thereof. Electron-rich, bulky butyl-di-1-adamantylphosphine and t-butyldicyclohexylphosphine afford the best results as described herein. Other bulky, basic phosphines such as, but not limited to, also include methyl-di-t-butylphosphine, bulky N-heterocyclic carbenes, and bulky phosphine oxides or mixtures or combinations thereof.

Any inorganic bases compatible with the solvent are suitable as for these reactions. Most preferred bases include, but are not limited to, CsOAc, CsF, K$_3$PO$_4$, K$_2$CO$_3$, Cs$_2$CO$_3$ and any other carbonates, phosphates, or fluorides or mixtures or combinations thereof. Potassium phosphate affords somewhat better selectivity for monoarylation and is cheaper than cesium salts. Potassium phosphate is used in all subsequent reactions for the arylation of heterocycles, and thus constitutes the most preferred base. Cesium carbonate is the most preferred base for the arylation of benzoic acids and phenols.

In certain embodiments, palladium acetate is the palladium catalyst of choice; however, other palladium compounds such as, but not limited to, palladium trifluoroacetate, palladium complexes with dibenzilideneacetone, and palladium on carbon are also suitable as well as mixtures of all or some of these palladium catalysts or mixtures or combinations thereof.

Optimized embodiments of the solvent system include N-methylpyrrolidinone for heterocycles and dimethylformamide for benzoic acids and phenols. For heterocycles, the optimized reaction conditions include N-methylpyrrolidinone as solvent, K$_3$PO$_4$ as base, butyldi-1-adamantylphosphine as ligand, and Pd(OAc)$_2$ as catalyst. In certain embodiments, the medium for arylations includes dipolar, aprotic solvents. In other embodiment, the solvents include, but are not limited to, hydrocarbon solvents such as toluene. The solvent system used in any of the reactions of this invention can include a mixture of these solvents.

In another embodiment, the present invention includes a variety of electron-rich heterocycles that are arylated using the above mentioned methodology set forth in Table I.

TABLE I

| | | List of Reactants and Product of C-C Forming Using Heteroycyclic Compounds | | |
|---|---|---|---|---|
| Entry | Heterocycle | ArCl | Product | Yield |
| 1[a] | Thiophene | 3-ClC$_6$H$_4$NHAc | | 54% |
| 2 | Benzothiophene | 2-chloro-6-methoxypyridine | | 72% |
| 3 | Benzothiophene | C$_6$H$_5$Cl | | 63% |

TABLE I-continued

List of Reactants and Product of C-C Forming Using Heteroycyclic Compounds

| Entry | Heterocycle | ArCl | Product | Yield |
|---|---|---|---|---|
| 4 | 3,5-Dimethyl-isoxazole | 1-chloro-naphthalene | | 76% |
| 5[b] | Benzofuran | C₆H₅Cl | | 68% |
| 1[a] | Thiophene | 3-ClC₆H₄NHAc | | 54% |
| 2 | Benzothiophene | 2-chloro-6-methoxypyridine | | 72% |
| 6 | Benzoxazole | 2-chloropyridine | | 67% |
| 7 | Benzoxazole | 3-ClC₆H₄CO₂Et | | 84% |
| 8 | Benzoxazole | 3-ClC₆H₄OMe | | 58% |
| 9 | Benzothiazole | 4-ClC₆H₄CF₃ | | 82% |
| 10 | Benzothiazole | C₆H₅Cl | | 84% |
| 11 | 2-Isobutyl-thiazole | 3-ClC₆H₄F | | 83% |

TABLE I-continued

List of Reactants and Product of C-C Forming Using Heteroycyclic Compounds

| Entry | Heterocycle | ArCl | Product | Yield |
|---|---|---|---|---|
| 12 | 2-Pivaloylamino-thiazole | 3-ClC$_6$H$_4$CF$_3$ | (5-(3-trifluoromethylphenyl)thiazol-2-yl pivaloylamide) | 79% |
| 13[c] | 1-Butylimidazole | C$_6$H$_5$Cl | (1-butyl-5-phenylimidazole) | 52% |
| 14 | 1-Methyl-1,2,4-triazole | 3,5-(MeO)$_2$C$_6$H$_3$Cl | (5-(3,5-dimethoxyphenyl)-1-methyl-1,2,4-triazole) | 76% |
| 15 | Caffeine | 4-ClC$_6$H$_4$CH$_3$ | (8-(4-methylphenyl)caffeine) | 86% |
| 1[a] | Thiophene | 3-ClC$_6$H$_4$NHAc | (3-(thiophen-2-yl)phenyl acetamide) | 54% |
| 2 | Benzothiophene | 2-chloro-6-methoxypyridine | (2-(6-methoxypyridin-2-yl)benzothiophene) | 72% |
| 16 | Caffeine | 2-ClC$_6$H$_4$OMe | (8-(2-methoxyphenyl)caffeine) | 71% |
| 17 | Caffeine | 3,5-Me$_2$C$_6$H$_3$Cl | (8-(3,5-dimethylphenyl)caffeine) | 77% |

[a]Thiophene (3 equiv), chloroarene (1 equiv).
[b]Benzofuran (1 equiv), chloroarene (3 equiv).
[c]2,5-Diphenylated derivative also isolated in 13% yield.
[e]Substrate (1 equiv), ArCl (1.5 equiv), K$_3$PO$_4$ (2 equiv), Pd (OAc)$_2$ (5 mol %), 24 hours at 125° C.
Yields are isolated yields.

Table I shows that thiophene and benzothiophene are reactive (Entries 1-3). Also, both 1,2- and 1,3-oxazole derivatives are successfully arylated (Entries 4, 6-8). Benzofuran is diarylated in a reasonable yield (Entry 5). Thiazole and benzothiazole arylation is also successful (Entries 9-12). In 2-substituted thiazoles the aryl group is introduced next to sulfur (Entries 11, 12). 1-n-Butylimidazole is arylated in 5-position, with some diarylation product also formed (Entry 13). 1-Methyl-1,2,4-triazole is selectively arylated in 5-position (Entry 14). Caffeine is very reactive and some of the resulting products are useful as adenosine receptor antagonists (Entries 15-17). If C—H activation methodology is not used as described in the present invention, the synthetic sequences leading to these compounds require several steps instead of a single step. Amide substitution is tolerated both on aryl chloride and heterocycle (Entries 1, 12), and the NH bond is not arylated. Chlorobenzoic acid esters are also used (Entry 7). 2-Chloropyridines are reactive (Entries 2, 6) and the products of these arylations may find use as chelating ligands. Both electron rich and electron-poor aryl chlorides are used; however, as expected, electron-poor chlorides are more reactive. Steric hindrance is tolerated on the heterocycle (Entry 4) and aryl chloride (Entry 16).

In another embodiment, the present invention includes a general procedure for the coupling of chloroarene with benzoic acids as shown below:

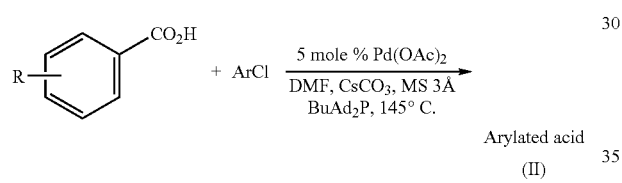

In certain embodiments, multiple aylations can occur, where multiple arylation is between 2 and the maximum number of aryl group the benzoic acid can accommodate. In other embodiments, n is between 2 and 4. In other embodiments, n is between 2 and 3. In other embodiments, n is 2. The reaction are generally performed at an elevated temperature. In certain embodiments, the elevated temperatures is sufficient to facilitate product formation, but not so high as to cause decomposition of the starting materials or products. In other embodiments, the temperature is between about 90° C. and about 160° C. In other embodiments, the temperatures is between about 100° C. and about 150° C. In other embodiments, the temperatures is between about 100° C. and about 140° C. In certain embodiments, the time is a period sufficient to achieve a desired conversion to product at a desired temperature. In other embodiments, the period of time is between about 30 minutes and about 24 hours. In other embodiments, the period of time is between about 1 hour and about 18 hours. In other embodiments, the period of time is between about 1 hour and about 12 hours. In other embodiments, the period of time is between about 2 hours and about 12 hours. In other embodiments, the period of time is between about 4 hours and about 12 hours. In other embodiments, the period of time is between about 6 hours and about 12 hours.

Although in most embodiments arylchlorides are the preferred halogenated aryl for arylation using the method of this invention, other halogens can be use as well including bromine and iodine.

TABLE II

List of Starting Benzoic Acids

| Entry | Starting Benzoic Acid | % Yield |
|---|---|---|
| 1 | (structure with F$_3$C, CF$_3$, Me, CO$_2$H) | 59 |
| 2 | (structure with Me, Me, Me, Me, CO$_2$H) | 53 |
| 3 | (structure with Cl, O$^i$Pr, CO$_2$H) | 69 |
| 4 | (structure with Cl, Cl, Br, CO$_2$H) | 53 |
| 5 | (structure with iPr, MeO, OMe, CO$_2$H) | 55 |

TABLE II-continued
List of Starting Benzoic Acids
| Entry | Starting Benzoic Acid | % Yield |
|---|---|---|
| 6 | 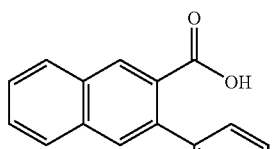 | 67 |
| 7 | 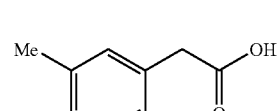 | 52 |
TABLE III
List of Starting Benzoic Acids and Resulting Arylated Benzoic Acids
| Entry | Acid, ArCl | Arylated Acid | % Yield |
|---|---|---|---|
| 1 | R-4-CF$_3$ (5)<br>Ar-4-CF$_3$C$_6$H$_4$ | | 75 |
| 2 | R-3-F (6)<br>Ar-4-CF$_3$C$_6$H$_4$ | | 91 |
| 3 | R-4-MeO$_2$C (7)<br>Ar-4-CF$_3$C$_6$H$_4$ | | 79 |
| 4 | R-3-CF$_3$ (6)<br>Ar-3-FC$_6$H$_4$ | | 72 |
| 5 | 6<br>Ar-4-MeC$_6$H$_4$ | | 83 |

TABLE III-continued

List of Starting Benzoic Acids and Resulting Arylated Benzoic Acids

| Entry | Acid, ArCl | Arylated Acid | % Yield |
|---|---|---|---|
| 6 | R—H (7)<br>Ar-4-CF$_3$C$_6$H$_4$ | [structure: 2,6-bis(4-trifluoromethylphenyl)benzoic acid] | 82 |
| 7 | R-2-Me (8)<br>Ar-4-CF$_3$C$_6$H$_4$ | [structure] | 72 |
| 8 | 8<br>Ar-3-CH$_3$C$_6$H$_4$ | [structure] | 91 |
| 9 | R-2-Ph<br>Ar-3,5-Me$_2$C$_6$H$_3$ | [structure] | 67 |
| 10 | R-3-Ph<br>Ar-Ph | [structure] | 71 |
| 11 | R-3-NO$_2$<br>Ar-Ph | [structure with N$_2$O] | 65 |
| 12 | R-3-CO$_2$Me<br>Ar-Ph | [structure] | 75 |

[a] Isolated as dimethyl ester

Outside the glovebox, a 2-dram vial equipped with a magnetic stir bar is charged with Pd(OAc)$_2$ (5 mol %), ArCO$_2$H (0.5 mmol) and chloroarene (2-3 equiv). The vial is flushed with argon, capped and placed inside a glovebox. To this mixture is added butyldi-1-adamantylphosphine (10 mol %), Cs$_2$CO$_3$ (2.2 equiv), molecular sieves 3 Å (155 mg) and anhydrous DMF (2.5 mL). The sealed vial is taken out of the glovebox, stirred at room temperature for 2 h and placed in a preheated oil bath (145° C.) for 24 h. The reaction mixture is allowed to cool to room temperature and quenched with 15% aqueous HCl (4 mL). Resulting suspension is extracted with ethyl acetate (3×3 mL) and the organic layer is filtered through a pad of Celite®. The filtrate is concentrated under vacuum to a volume of about 2 μmL. The mixture is adsorbed on silica gel and subjected to flash chromatography (hexanes then dichlorormethane-ethyl acetate 95:5). The DCM-EtOAc fraction is concentrated, the residue is triturated with distilled water (3×2 mL) and dried under reduced pressure. The residue, after trituration with hexanes (2×2 mL) and/or purification by preparative HPLC and drying under reduced pressure (50° C.) yield the product.

The reactions are optimized with respect to solvent, phosphine ligand, and the presence of molecular sieves. The best results are obtained in dry DMF in the presence of molecular sieves. Wet DMF in the presence of wet molecular sieves results in slower reactions, omission of molecular sieves results in incomplete reactions, and no reaction is observed in DMA. The best results are obtained with n-butyl-di-1-adamantylphosphine as ligand. Other ligands include trioctylphosphine, tri-o-tolylphosphine, and triphenylphosphine ligands, though substantial conversions are observed with tricyclohexylphosphine, di-t-butylmethylphosphine, and t-butyldicyclohexylphosphine. Both electron-poor (entries 6, 7) and electron-rich (entry 8) aryl chlorides are reactive.

In another embodiment, the present invention includes a general procedure for the coupling of chloroarene with phenols as shown below:

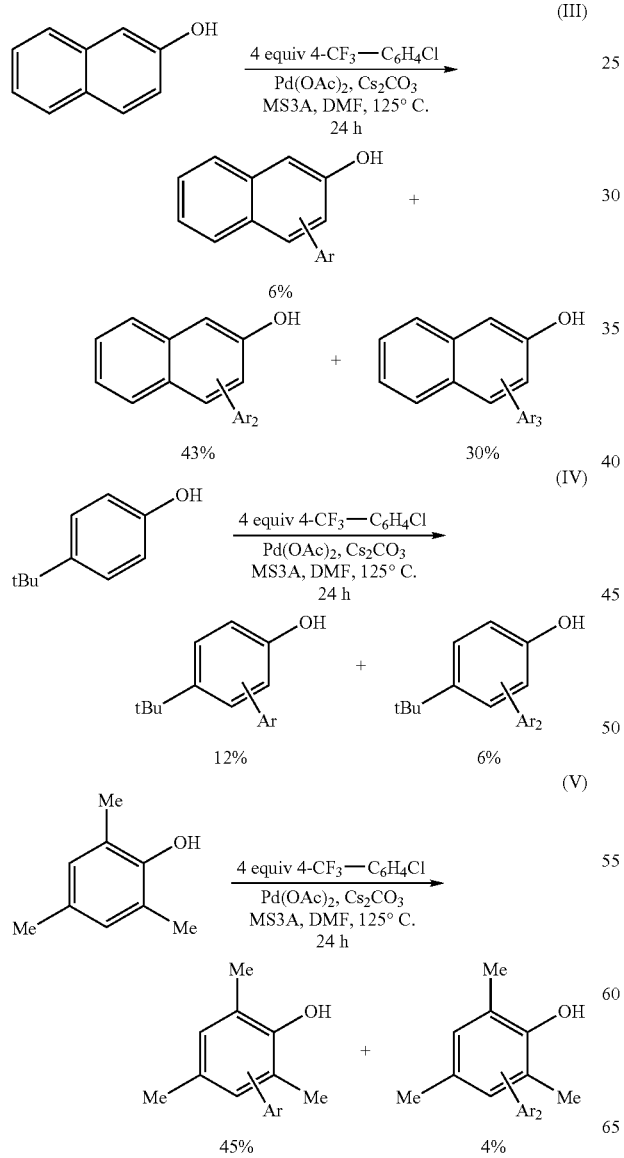

An example is given for the coupling of chlorobenzene with 2-naphthol. Outside the glovebox, a 2-dram vial equipped with a magnetic stir bar is charged with Pd(OAc)$_2$ (5 mol %), 2-naphthol (0.5 mmol) and chloroarene (5 equiv). The vial is flushed with argon, capped and placed inside a glovebox. To this mixture is added butyldi-1-adamantylphosphine (10 mol %), Cs$_2$CO$_3$ (2.2 equiv), molecular sieves 3 Å (155 mg) and anhydrous DMF (2.5 mL). The sealed vial is taken out of the glovebox, stirred at room temperature for 2 h and placed in a preheated oil bath (125° C.) for 24 h. The reaction mixture is allowed to cool to room temperature and quenched with 15% aqueous HCl (4 mL). Resulting suspension is extracted with ethyl acetate (3×3 mL) and the organic layer is filtered through a pad of Celite®. The conversion rate is determined by GC and is shown below the compounds. In certain embodiments, multiple aylations can occur, where multiple arylation is between 2 and the maximum number of aryl group the benzoic acid can accommodate. In other embodiments, n is between 2 and 4. In other embodiments, n is between 2 and 3. In other embodiments, n is 2. The reaction are generally performed at an elevated temperature. In certain embodiments, the elevated temperatures is sufficient to facilitate product formation, but not so high as to cause decomposition of the starting materials or products. In other embodiments, the temperature is between about 90° C. and about 160° C. In other embodiments, the temperature is between about 100° C. and about 150° C. In other embodiments, the temperatures is between about 100° C. and about 140° C. In certain embodiments, the time is a period sufficient to achieve a desired conversion to product at a desired temperature. In other embodiments, the period of time is between about 30 minutes and about 24 hours. In other embodiments, the period of time is between about 1 hour and about 18 hours. In other embodiments, the period of time is between about 1 hour and about 12 hours. In other embodiments, the period of time is between about 2 hours and about 12 hours. In other embodiments, the period of time is between about 4 hours and about 12 hours. In other embodiments, the period of time is between about 6 hours and about 12 hours.

EXPERIMENTS OF THE INVENTION

Experimental Section I

Palladium-Catalyzed Arylation of Electron-Rich Heterocycles with Aryl Chlorides

General Considerations
Reactions were performed in 2-dram vials with PTFE caps. Flash chromatography was performed on 60 Å silica gel (Sorbent Technologies). Purification by preparative HPLC was performed on a Shimadzu Prominence LC (LC-20AB) HPLC equipped with a SPD-20A UV-Vis detector and a Varian Dynamax (250 mm×21.4 mm) column. GC analyses were performed on a Shimadzu CG-2010 chromatograph equipped with a Restek column (Rtx®-5, 15 m, 0.25 mm ID). The $^1$H NMR and $^{13}$C NMR spectra were recorded on a GE QE-300 spectrophotometer using residual solvent peak as a reference. Melting points were measured on a Mel-Temp apparatus and are uncorrected. Elemental analyses were performed by Atlantic Microlab Inc. Of Norcross, Ga. IR spectra were obtained using ThermoNicolet Avatar 370 FT instrument.
Materials
Palladium acetate used in this study was obtained from J&J Materials and was used as received. Powdered K$_3$PO$_4$ (Aldrich), anhydrous NMP (Acros) and butyldi-1-adamantylphosphine (Strem) were stored under argon. The following starting materials were obtained from commercial sources and were used without further purification: 2-iso-butylthiazole, 4-chlorobenzotrifluoride, 1-chloro-3-fluorobenzene, 3-chlorobenzontrifluoride, 5-chloro-m-xylene were purchased from Oakwood Products. 2,3-Benzofuran, benzoxazole, benzothiazole, 3-chloroacetanilide, chlorobenzene, 3-chloroanisole, 5-chloro-1,3-dimethoxybenzene, 2-chloroanisole were obtained from Acros. 1-n-Butylimidazole, thiophene and benzothiophene were purchased from Aldrich. 3,5-Dimethylisoxazole, caffeine, 1-chloronaphthalene and 2-chloropyridine were purchased from Eastman, p-chlorotoluene from Matheson, and 2-chloro-6-methoxypyridine from Alfa Aesar. The ethyl 3-chlorobenzoate was prepared from 3-chlorobenzoic acid (Aldrich)[1]. 2-Pivaloylaminothiazole was prepared from 2-aminothiazole (Aldrich).[2] Benzothiazole and 2-deuterobenzothiazole[3] (>99% D by NMR integration) used in the kinetic experiments were purified by distillation under reduced pressure before use.

A. General Procedure for Coupling of Chloroarenes with Heterocyclic Compounds

Outside the glovebox a 2-dram vial equipped with a magnetic stir bar was charged with Pd(OAc)$_2$ (5 mol %), heterocycle (1.0 mmol) and chloroarene (1.5 equiv). The vial was flushed with argon, capped and placed inside a glovebox. To this mixture was added butyldi-1-adamantylphosphine (10 mol %), K$_3$PO$_4$ (2.0 equiv) and anhydrous NMP (4 mL). The sealed vial was taken out of the glovebox, stirred at room temperature for 15 min and placed in a preheated oil bath (125° C.) for 24 h. The reaction mixture was allowed to cool to room temperature and quenched with 1% aqueous KOH (10 mL). Resulting suspension was extracted with dichloromethane (3×5 mL) and the organic layer filtered through a pad of Celite®. The filtrate was concentrated under vacuum to a volume of about 2 mL. The mixture was absorbed on silica gel and subjected to flash chromatography. After concentration of the fractions containing the product, the residue was dried under reduced pressure (40° C.) to yield pure arylated heterocycle.

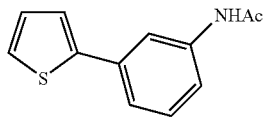

N-(3-Thiophen-2-yl-Phenyl)Acetamide (Entry 1, Table I)[4]

Figure 3A:
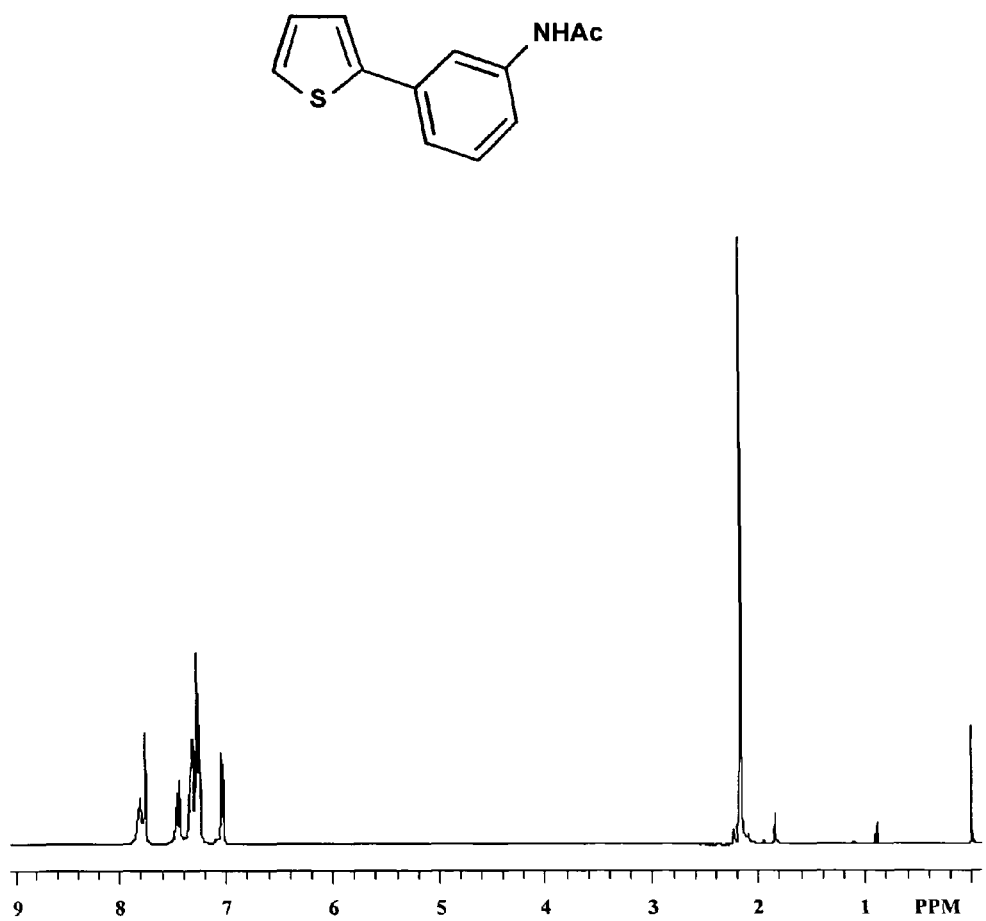
FIG. 3A depicts a $^1$H NMR spectrum of Entry 1 of Table I.

Palladium acetate (11.4 mg, 0.05 mmol), thiophene (252 mg, 3.0 mmol), 3-chloroacetanilide (170 mg 1.0 mmol), butyldi-1-adamantylphosphine (38.5 mg, 0.1 mmol), K$_3$PO$_4$ (425 mg, 2.0 mmol) and anhydrous NMP (4.0 mL). After column chromatography (1/1 ethyl acetate/hexanes) 117 mg (54%) of light tan needles were obtained, mp 134-135° C. (2,2,4-trimethylpentane). R$_f$-0.42 (1/1 ethyl acetate/hexanes). $^1$H NMR (300 MHz, CDCl$_3$) δ 2.17 (s, 3H), 7.02-7.05 (m, 1H), 7.24-7.35 (m, 5H), 7.60 (dm, J-7.2 Hz, 1H), 7.7 6 (s, 1H), 7.5 (br 1H). $^{13}$C NMR (75 MHz, CDCl$_3$) δ 25.1, 117.9, 119.6, 122.4, 124.0, 125.6, 128.6, 130.0, 135.7, 139.0, 144.4, 169.3. FT-IR (neat, cm$^1$) u 1664, 1482. The $^1$H NMR $^{13}$C NMR spectra are shown in FIGS. 3A&B, respectively.

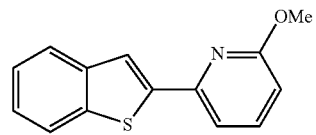

2-(6-Methoxy-1-Pyridyl)Benzothiophene (Entry 2, Table I)

Figure 4A:
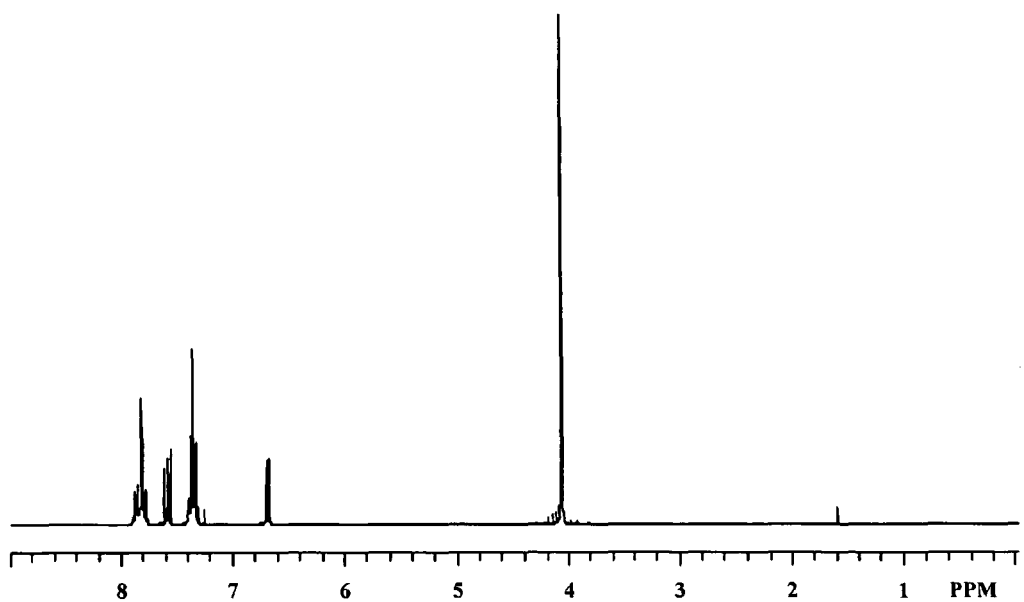
FIG. 4A depicts a $^1$H NMR spectrum of Entry 2 of Table I.
Figure 4B:
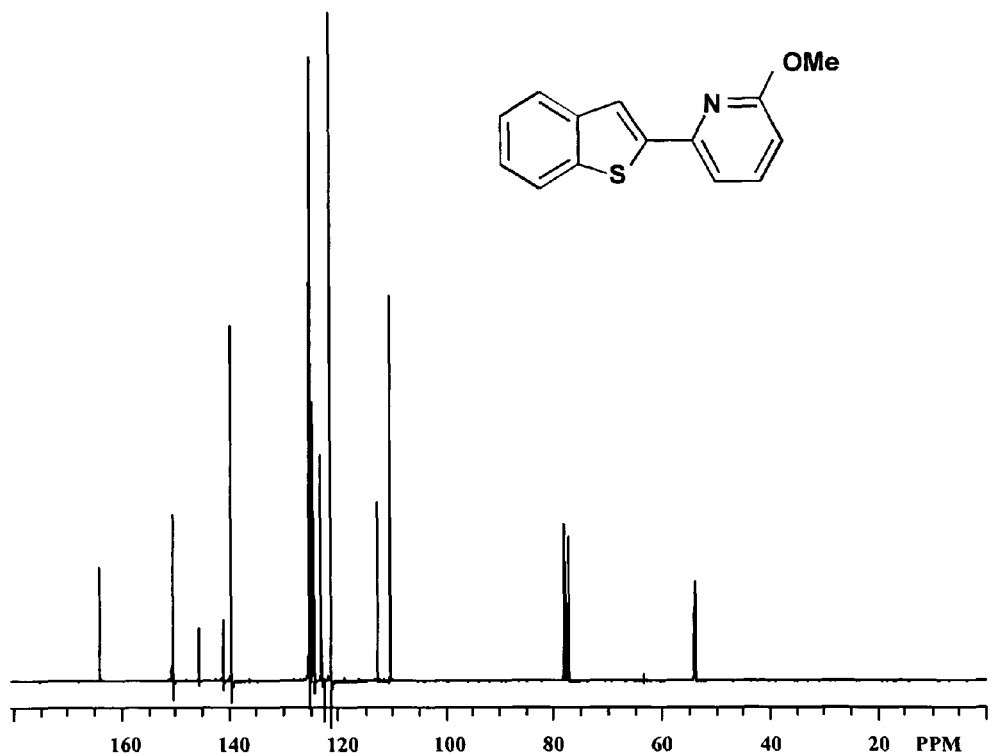
FIG. 4B depicts a $^{13}$C NMR spectrum of Entry 2 of Table I.

Palladium acetate (11.4 mg, 0.05 mmol), benzothiophene (134 mg, 1.0 mmol), 2-chloro-6-methoxypyridine (216 mg, 1.5 mmol), butyldi-1-adamantylphosphine (38.5 mg, 0.1 mmol), K$_3$PO$_4$ (425.0 mg, 2.0 mmol) and anhydrous NMP (4.0 mL). After column chromatography (1/9 ethyl acetate/hexanes) and preparative HPLC (2% ethyl acetate in hexanes) 174 mg (72%) of a white solid was obtained, mp 94-95° C. (2,2,4-trimethylpentane). R$_f$-0.54 (1/9 ethyl acetate/hexanes). $^1$H NMR (300 MHz, CDCl$_3$) δ 4.06 (s, 3H), 6.68 (d, J-8.4 Hz, 1H), 7.33-7.37 (m, 3H), 7.58 (dd, J-7.2 Hz, 7.5 Hz, 1H), 7.78-7.88 (m, 3H). $^{13}$C NMR (75 MHz, CDCl$_3$) δ 54.0, 110.4, 112.8, 121.4, 122.5, 124.6, 125.0, 125.4, 139.6, 141.0, 141.1, 145.6, 150.5, 164.1. FT-IR (neat, cm$^1$) u 1573, 1461. Anal calcd for C$_{14}$H$_{11}$NOS (241.31 g/mol): C, 69.68; H, 4.59; N, 5.80. Found C, 69.74; H, 4.67; N, 5.82. The $^1$H NMR and $^{13}$C NMR spectra are shown in FIGS. 4A&B, respectively.

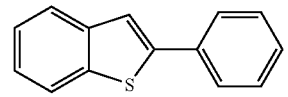

2-Phenylbenzo[b]Thiophene (Entry 3, Table I)

Figure 5:
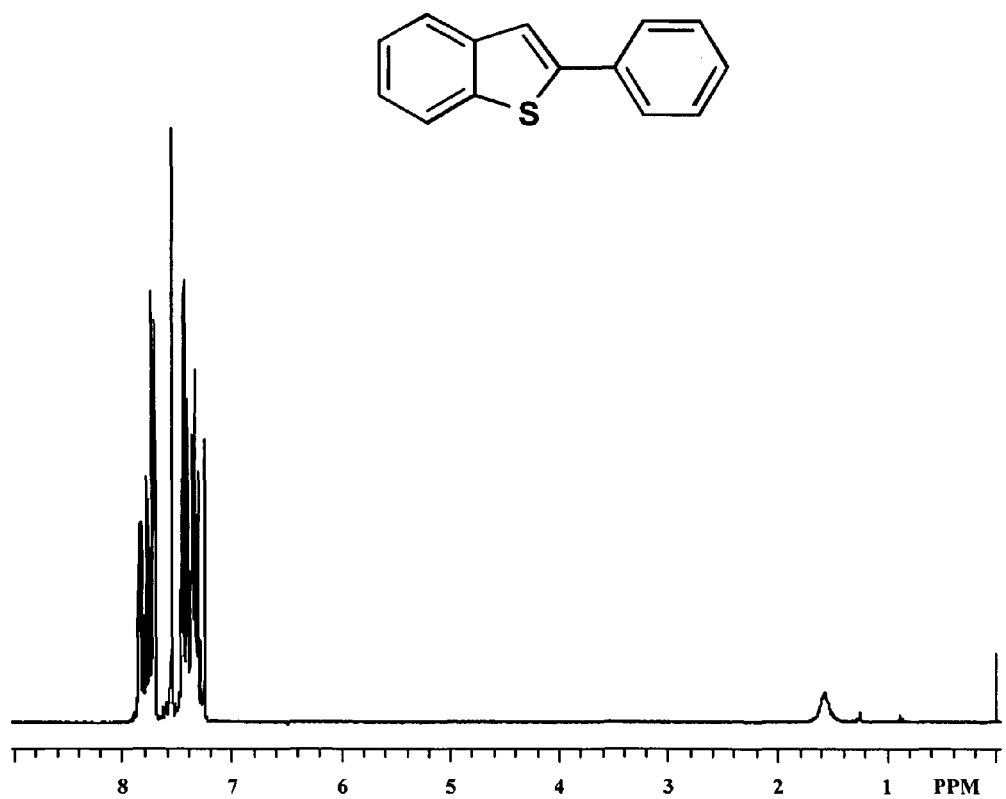
FIG. 5 depicts a $^1$H NMR spectrum of Entry 3 of Table I.

Palladium acetate (11.4 mg, 0.05 mmol), benzothiophene (134 mg, 1.0 mmol), chlorobenzene (169 mg, 1.5 mmol), butyldi-1-adamantylphosphine (38.5 mg, 0.1 mmol), K$_3$PO$_4$ (425 mg, 2.0 mmol) and anhydrous NMP (4 mL). After column chromatography (1/9 ethyl acetate/hexanes) 132 mg (63%) of a light yellow solid was obtained. This compound is known.[5] $^1$H NMR (300 MHz, CDCl$_3$) δ 7.29-7.47 (m, 5H), 7.56 (s, 1H), 7.71-7.85 (m, 4H). The $^1$H NMR spectrum is shown in FIG. 5.

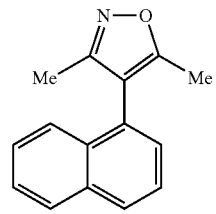

3,5-Dimethyl-4-(1-Naphtyl)Isoxazole (Entry 4, Table I)

Figure 6:
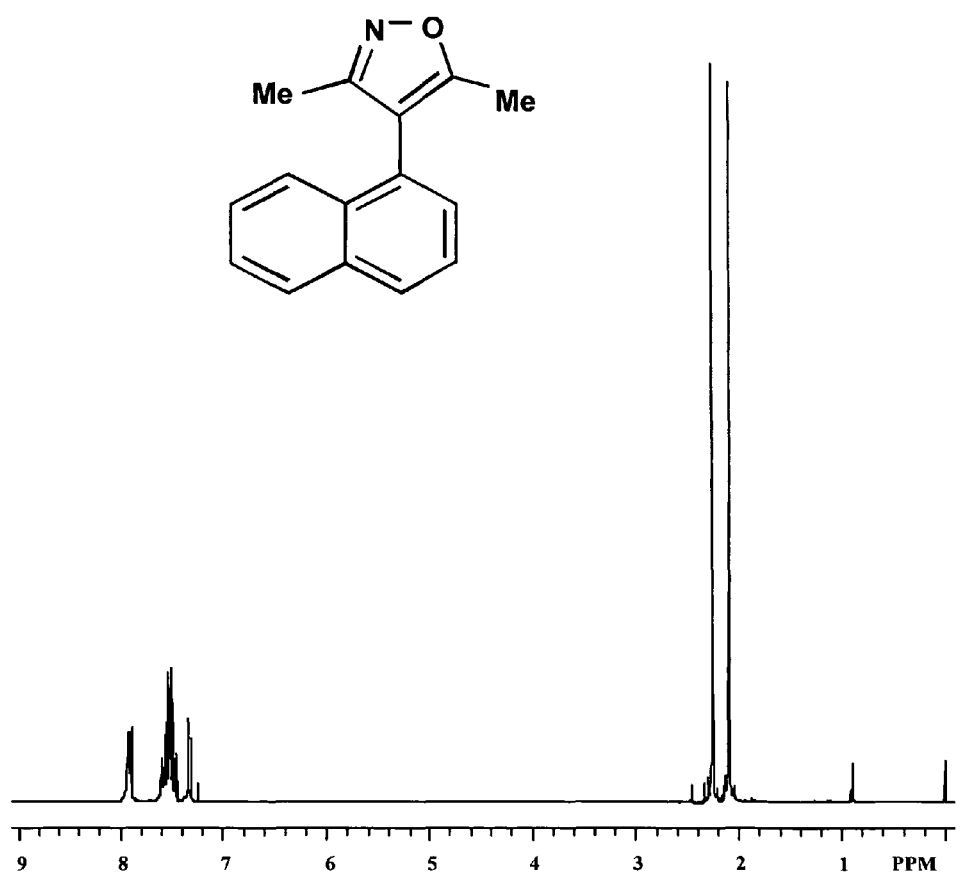
FIG. 6 depicts a $^1$H NMR spectrum of Entry 4 of Table I.

Palladium acetate (11.4 mg, 0.05 mmol), 3,5-dimethylisoxazole (97 mg, 1.0 mmol), 1-chloronaphthalene (244 mg, 1.5 mmol), butyldi-1-adamantylphosphine (38.5 mg, 0.1 mmol), K₃PO₄ (425 mg, 2.0 mmol) and anhydrous NMP (4 mL). After column chromatography (1/9 ethyl acetate/hexanes) 170 mg (76%) of a white solid was obtained. This compound is known.[6] ¹H NMR (300 MHz, CDCl₃) δ 2.10 (s, 3H), 2.26 (s, 3H), 7.33 (dd, J-7.2 Hz, 0.9 Hz, 1H), 7.45-7.60 (m 4H), 7.89-7.94 (m, 2H). The ¹H NMR spectrum is shown in FIG. 6.

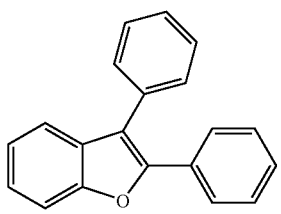

2,3-Diphenylbenzo[b]Furan (Entry 5, Table I)

Figure 7:
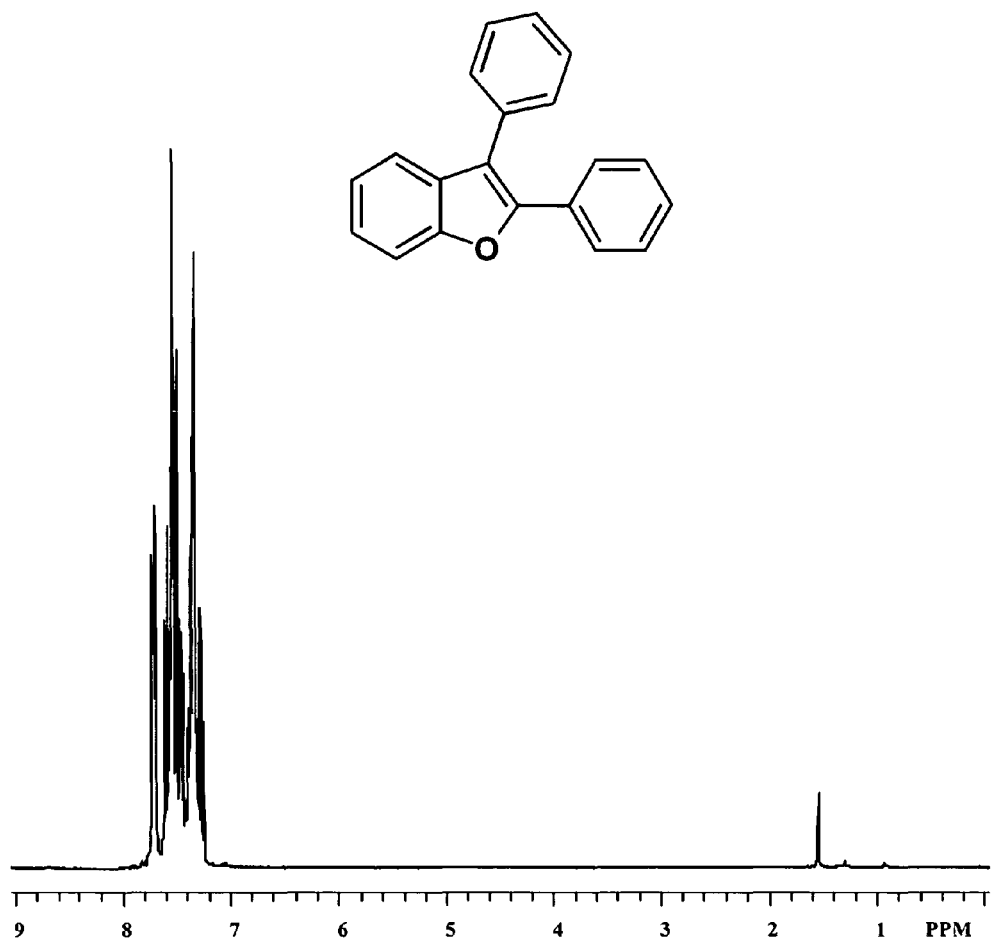
FIG. 7 depicts a $^1$H NMR spectrum of Entry 5 of Table I.

Palladium acetate (11.4 mg, 0.05 mmol), benzofuran (118 mg 1.0 mmol), chlorobenzene (338 mg, 3.0 mmol), butyldi-1-adamantylphosphine (38.5 mg, 0.1 mmol), K₃PO₄ (425 mg, 2.0 mmol) and anhydrous NMP (4 mL). After column chromatography (1/99 ethyl acetate/hexanes) 184 mg (68%) of a white solid was obtained. This compound is known.[7] ¹H NMR (300 MHz, CDCl₃) δ 7.27-7.39 (m, 5H), 7.44-7.61 (m, 7H), 7.69-7.73 (m, 2H). The ¹H NMR spectrum is shown in FIG. 7.

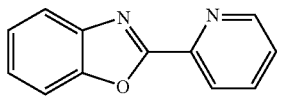

2-(2-Pyridyl)Benzoxazole (Entry 6, Table I)

Figure 8:
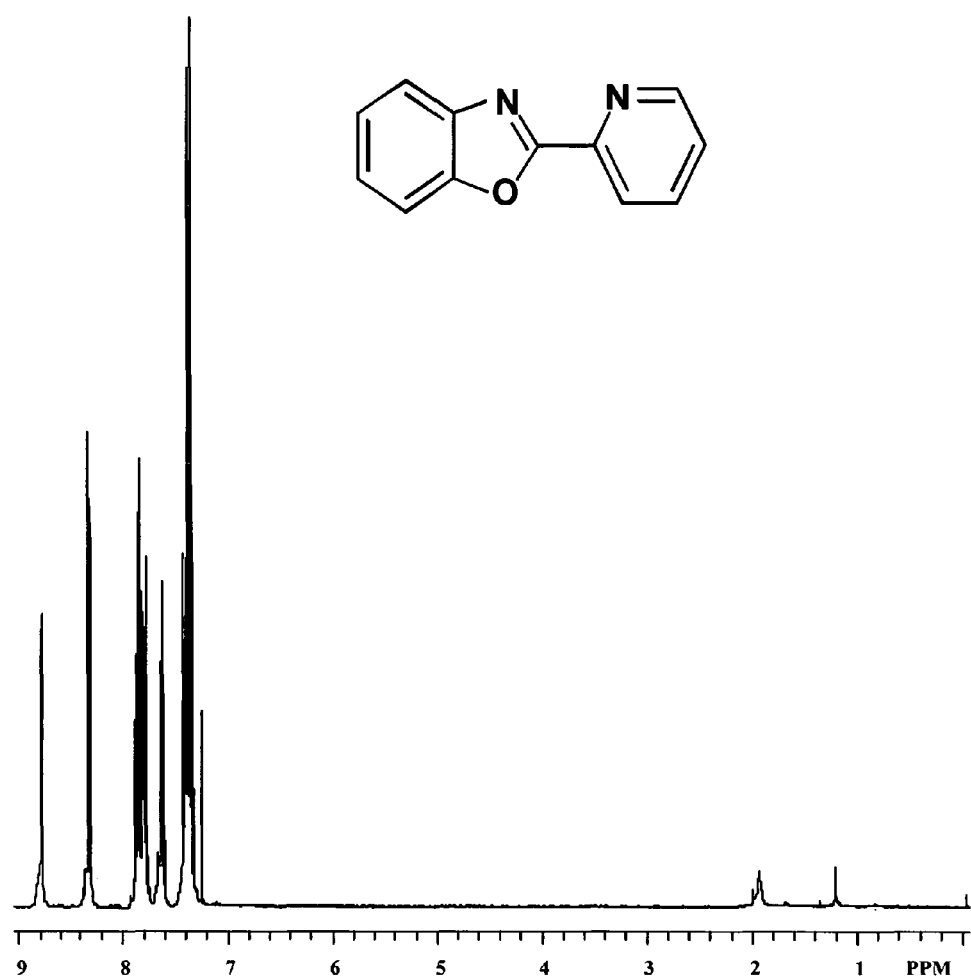
FIG. 8 depicts a $^1$H NMR spectrum of Entry 6 of Table I.

Palladium acetate (11.4 mg, 0.05 mmol), benzoxazole (119 mg, 1.0 mmol), 2-chloropyridine (171 mg, 1.5 mmol), butyldi-1-adamantylphosphine (38.5 mg, 0.1 mmol), K₃PO₄ (425 mg, 2.0 mmol) and anhydrous NMP (4 mL). After column chromatography (3/7 ethyl acetate/hexanes) 132 mg (67%) of a white solid was obtained. This compound is known. ¹H NMR (300 MHz, CDCl₃) δ 7.33-7.43 (m, 3H), 7.62-7.64 (m, 1H), 7.78-7.88 (m, 2H), 8.31-8.34 (m, 1H), 8.77-8.80 (m, 1H). The ¹H NMR spectrum is shown in FIG. 8.

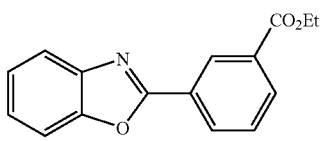

Ethyl 3-(2-Benzoxazolyl)Benzoate (Entry 7, Table I)

Figure 9A:
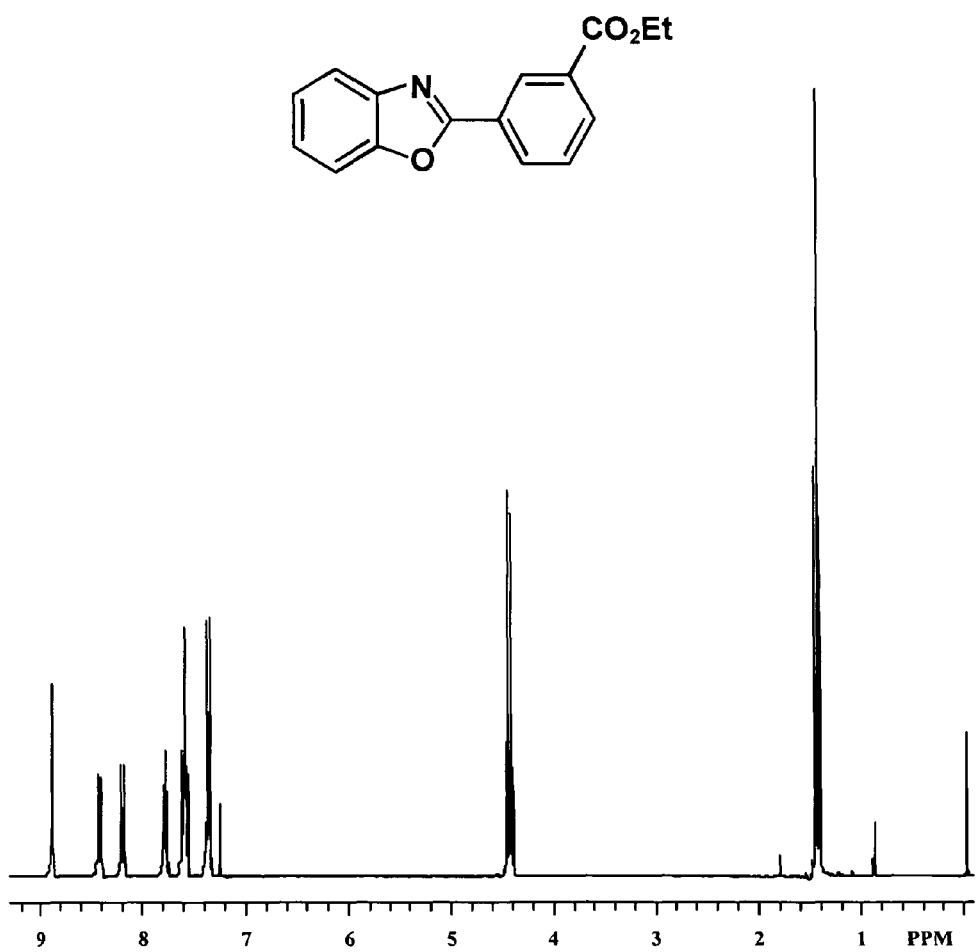
FIG. 9A depicts a $^1$H NMR spectrum of Entry 7 of Table I.
Figure 9B:
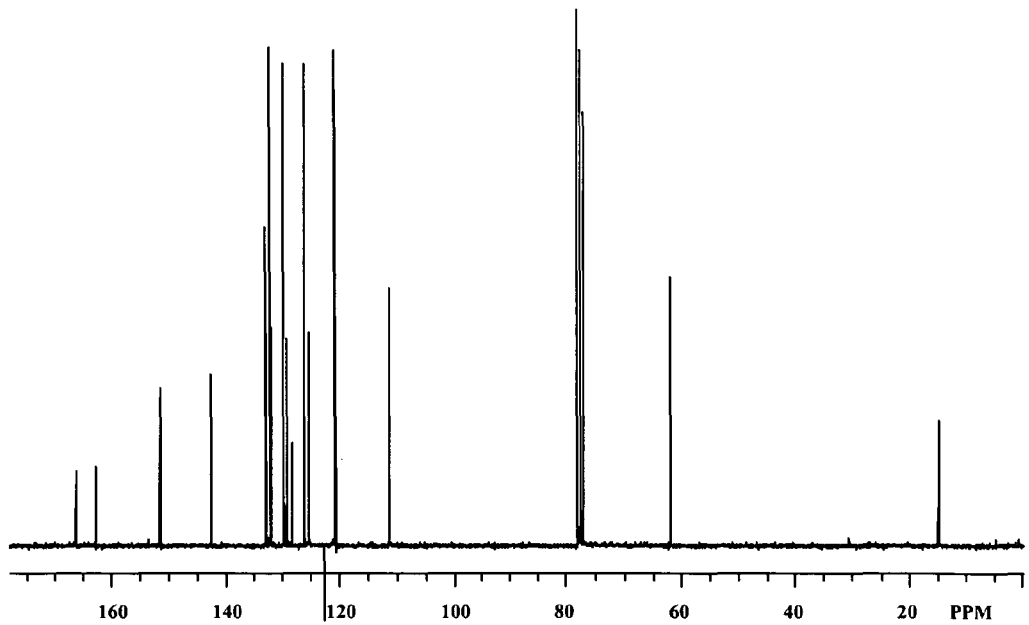
FIG. 9B depicts a $^{13}$C NMR spectrum of Entry 7 of Table I.

Palladium acetate (11.4 mg, 0.05 mmol), benzoxazole (119 mg, 1.0 mmol) ethyl 3-chlorobenzoate (277 mg, 1.5 mmol), butyldi-1-adamantylphosphine (38.5 mg, 0.1 mmol), K₃PO₄ (425 mg, 2.0 mmol) and anhydrous NMP (4 mL). After column chromatography (1/9 ethyl acetate/hexanes) 225 mg (84%) of a light brown solid was obtained, mp 103-104° C. (2,2,4-trimethylpentane). $R_f$-0.58 (1/9 ethyl acetate/hexanes). ¹H NMR (300 MHz, CDCl₃) δ 4.43 (t, J-7.2 Hz, 3H), 4.43 (q, J-7.2 Hz 2H), 7.35-7.38 (t, 2H), 7.57-7.62 (m, 2H), 7.77-7.80 (m, 1H), 8.19-8.21 (m, 1H), 8.41-8.44 (m, 1H), 8.88-8.89 (m 1H). ¹³C NMR (75 MHz, CDCl₃) δ 14.9, 61.9, 120.7, 122.5, 125.2, 125.9, 128.1, 129.1, 129.6, 132.0, 132.1, 133.0, 142.5, 151.3, 162.6, 166.3. FT-IR (neat cm¹) u 1715, 1240. Anal calcd for C₁₆H₁₃NO₃ (267.28 g/mol). C, 71.90; H, 4.90; N, 5.24. Found C, 71.91; H, 5.14; N, 5.15. The ¹H NMR and ¹³C NMR spectra are shown in FIGS. 9A&B, respectively.

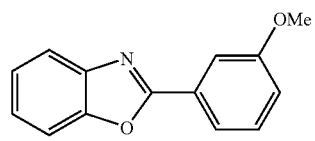

2-(3-Methoxyphenyl)Benzoxazole (Entry 8, Table I)

Figure 10:
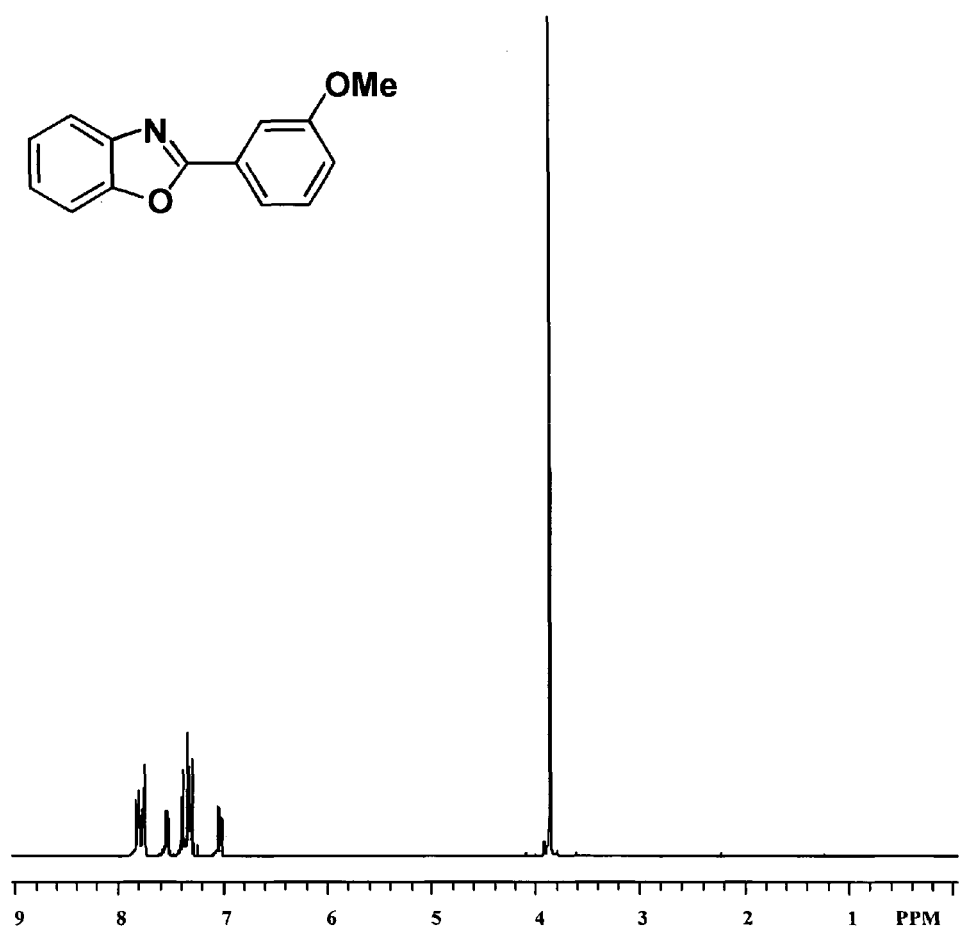
FIG. 10 depicts a $^1$H NMR spectrum of Entry 8 of Table I.

Palladium acetate (11.4 mg, 0.05 mmol), benzoxazole (119 mg, 1.0 mmol), 3-chloroanisole (214 mg, 1.5 mmol), butyldi-1-adamantylphosphine (38.5 mg, 0.1 mmol), K₃PO₄ (425 mg, 2.0 mmol) and anhydrous NMP (4 mL). After column chromatography (2/8 ethyl acetate/hexanes) 131 mg (58%) of a white solid was obtained. This compound is known.[9] ¹H NMR (300 MHz, CDCl₃) δ 3.86 (s, 3H), 7.02-7.06 (m, 1H), 7.30-7.41 (m, 3H), 7.52-7.55 (m, 1H), 7.74-7.83 (3H). The ¹H NMR spectrum is shown in FIG. 10.

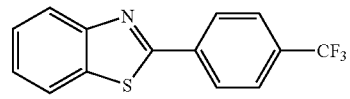

2-(4-Trifluoromethylphenyl)Benzothiazole (Entry 9, Table I)

Figure 11:
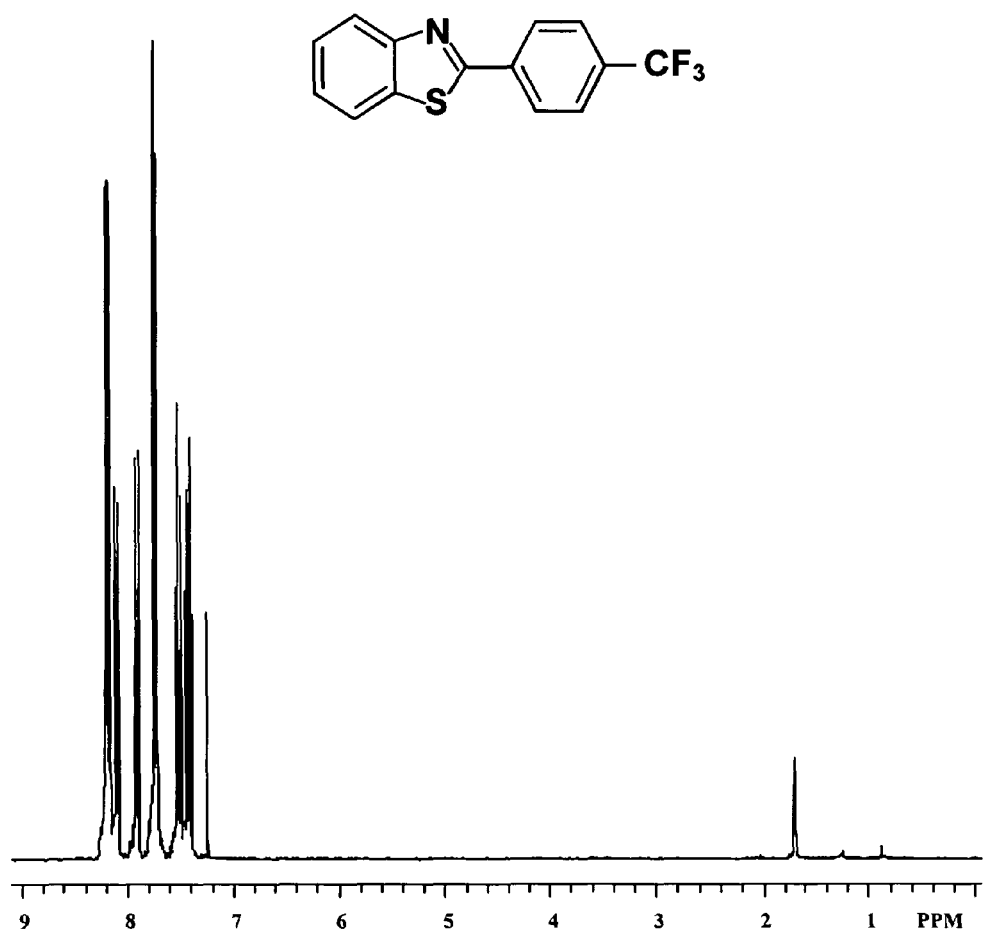
FIG. 11 depicts a $^1$H NMR spectrum of Entry 9 of Table I.

Palladium acetate (11.4 mg, 0.05 mmol), benzothiazole (135 mg 1.0 mmol), 4-chlorobenzotrifluoride (270 mg, 1.5 mmol), butyldi-1-adamantylphosphine (38.5 mg, 0.1 mmol), K₃PO₄ (425 mg, 2.0 mmol) and anhydrous NMP (4 mL). After column chromatography (1/9 ethyl acetate/hexanes) 229 mg (82%) of a white solid was obtained. This compound is known.[10] ¹H NMR (300 MHz, CDCl₃) δ 7.40-7.45 (m, 1H), 7.50-7.56 (m, 1H), 7.73 (d, J-8.7 Hz, 2H), 7.91 (d, J-6.6 Hz, 1H), 8.09 (d, J-6.9 Hz, 1H), 8.18 (d, J-8.4 Hz, 2H). The ¹H NMR spectrum is shown in FIG. 11.

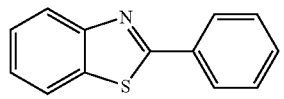

2-Phenylbenzothiazole (Entry 10, Table I)

Figure 12:
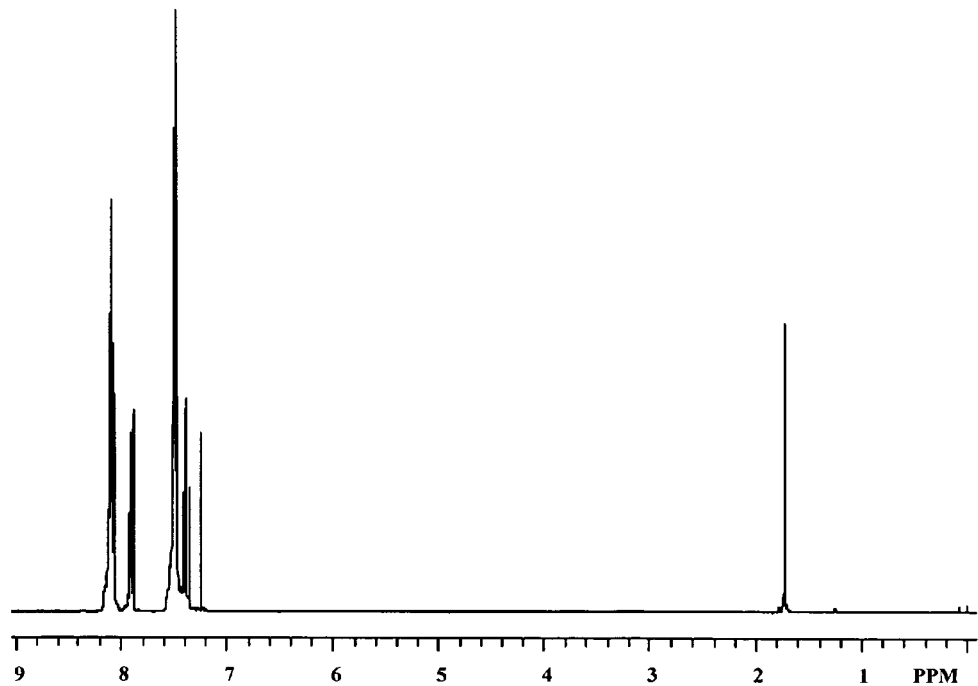
FIG. 12 depicts a $^1$H NMR spectrum of Entry 10 of Table I.

Palladium acetate (11.4 mg, 0.05 mmol), benzothiazole (135 mg, 1.0 mmol) 3-chlorobenzene (169 mg, 1.5 mmol), butyldi-1-adamantylphosphine (38.5 mg, 0.1 mmol), K₃PO₄ (425 mg, 2.0 mmol) and anhydrous NMP (4 mL). After column chromatography (1/9 ethyl acetate/hexanes) 177 mg (84%) of a light tan solid was obtained. This compound is known.[10] ¹H NMR (300 MHz, CDCl₃) δ 7.36-7.41 (m, 1H), 7.47-7.52 (m, 4H), 7.90 (d, J-6.9 Hz, 1H), 8.07-8.11 (m, 3H). The ¹H NMR spectrum is shown in FIG. 12.

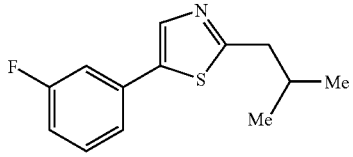

5-(3-Fluorophenyl)-2-Isobutylthiazole (Entry 11, Table I)

Figure 13A:
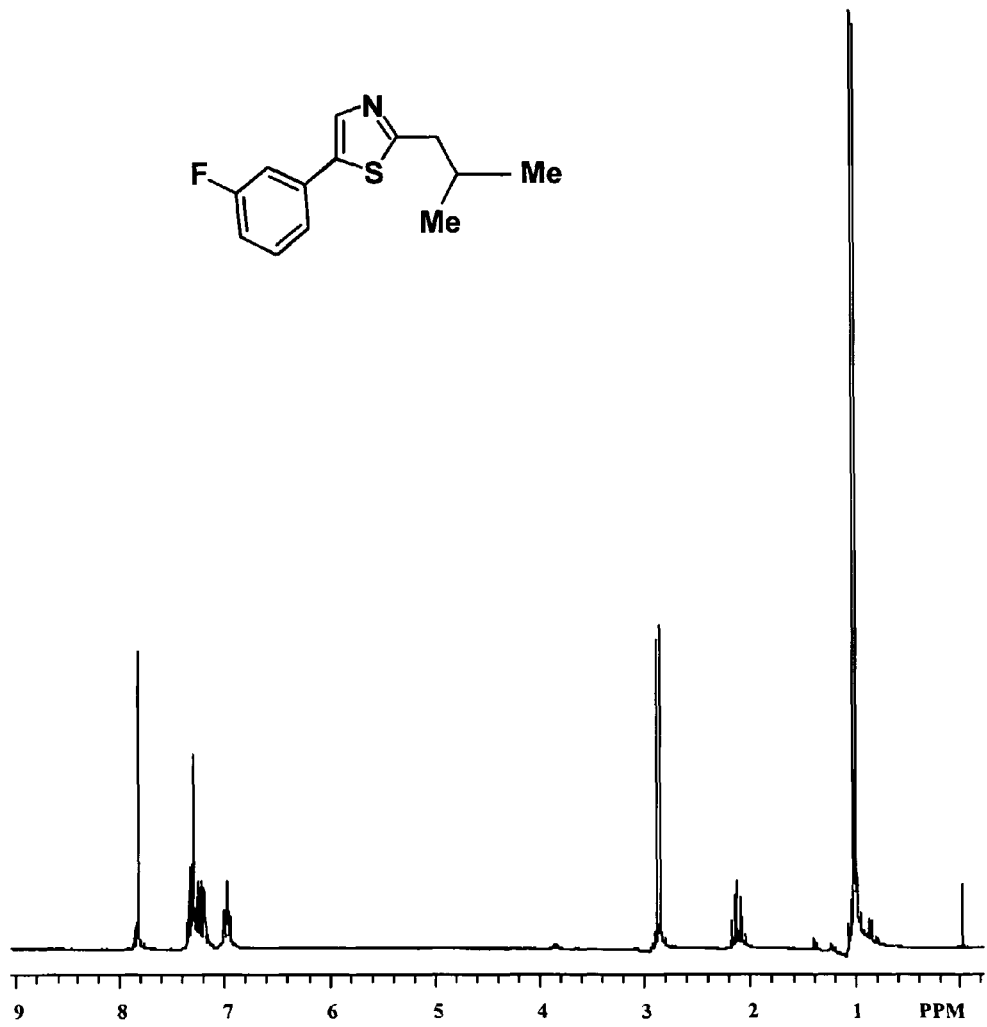
FIG. 13A depicts a $^1$H NMR spectrum of Entry 11 of Table I.
Figure 13B:
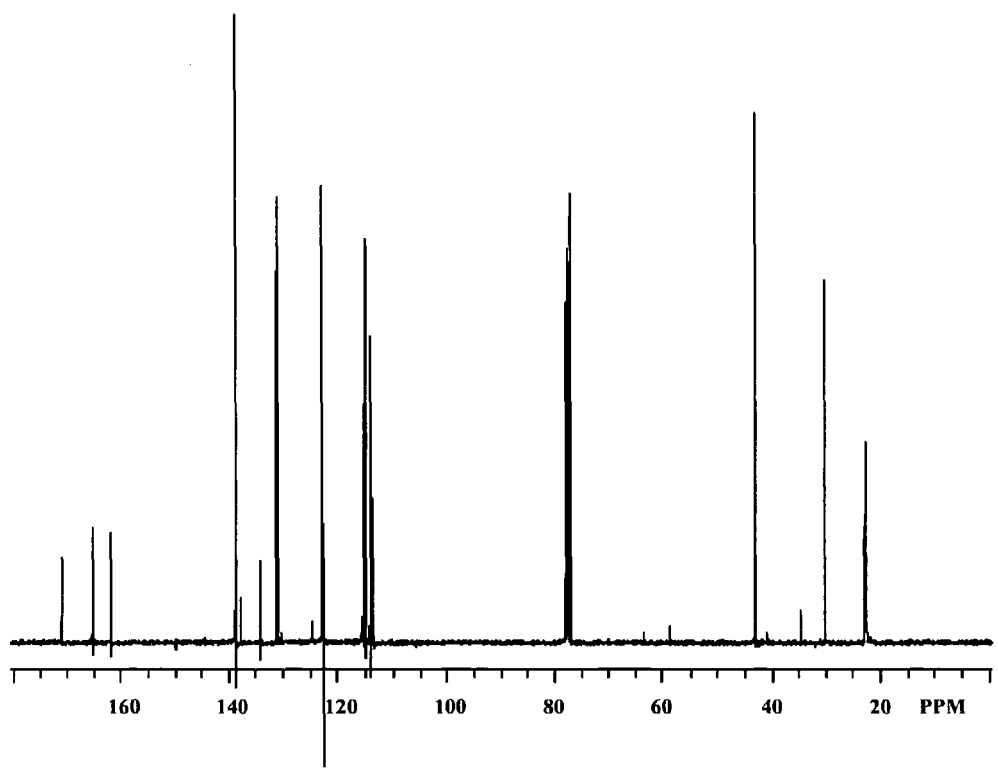
FIG. 13B depicts a $^{13}$C NMR spectrum of Entry 11 of Table I.

Palladium acetate (11.4 mg, 0.05 mmol), 2-isobutylthiazole (141 mg, 1.0 mmol), 3-fluorochlorobenzene (196 mg, 1.5 mmol), butyldi-1-adamantylphosphine (38.5 mg, 0.1 mmol), $K_3PO_4$ (425 mg, 2.0 mmol) and anhydrous NMP (4 mL). After column chromatography (3/7 ethyl acetate/hexanes) 198 mg (83%) of a tan oil was obtained, $R_f$-0.27 (1/9 ethyl acetate/hexanes). ¹H NMR (300 MHz, $CDCl_3$) δ 1.00 (d, J-6.6 Hz, 6H), 2.12 (septet, J-6.6 Hz, 1H), 2.87 (d, J-6.6 Hz, 2H), 6.95-7.01 (m, 1H), 7.19-7.37 (m, 3H), 7.82 (s, 1H). ¹³C NMR (75 MHz, $CDCl_3$) δ 22.8, 30.4, 43.1, 113.9 (d, J-22.4 Hz), 115.3 (d, J-21.5 Hz), 122.7, 131.1 (d, J-8.4 Hz), 134.3 (d, J-7.4 Hz), 137.7, 138.8, 163.6 (d, J-246.6 Hz), 170.9. FT-IR (neat, $cm^1$) u 1612, 1585. Anal calcd for $C_{13}H_{14}FNS$ (235.32 g/mol): C, 66.35; H, 6.00; N, 5.95. Found C, 66.79; H, 5.95; N, 5.77. The ¹H NMR and ¹³C NMR spectra are shown in FIGS. 13A&B, respectively.

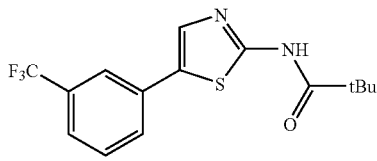

2-Pivaloylamino-5-(3-Trifluoromethylphenyl)Thiazole (Entry 12, Table 1)

Figure 14A:
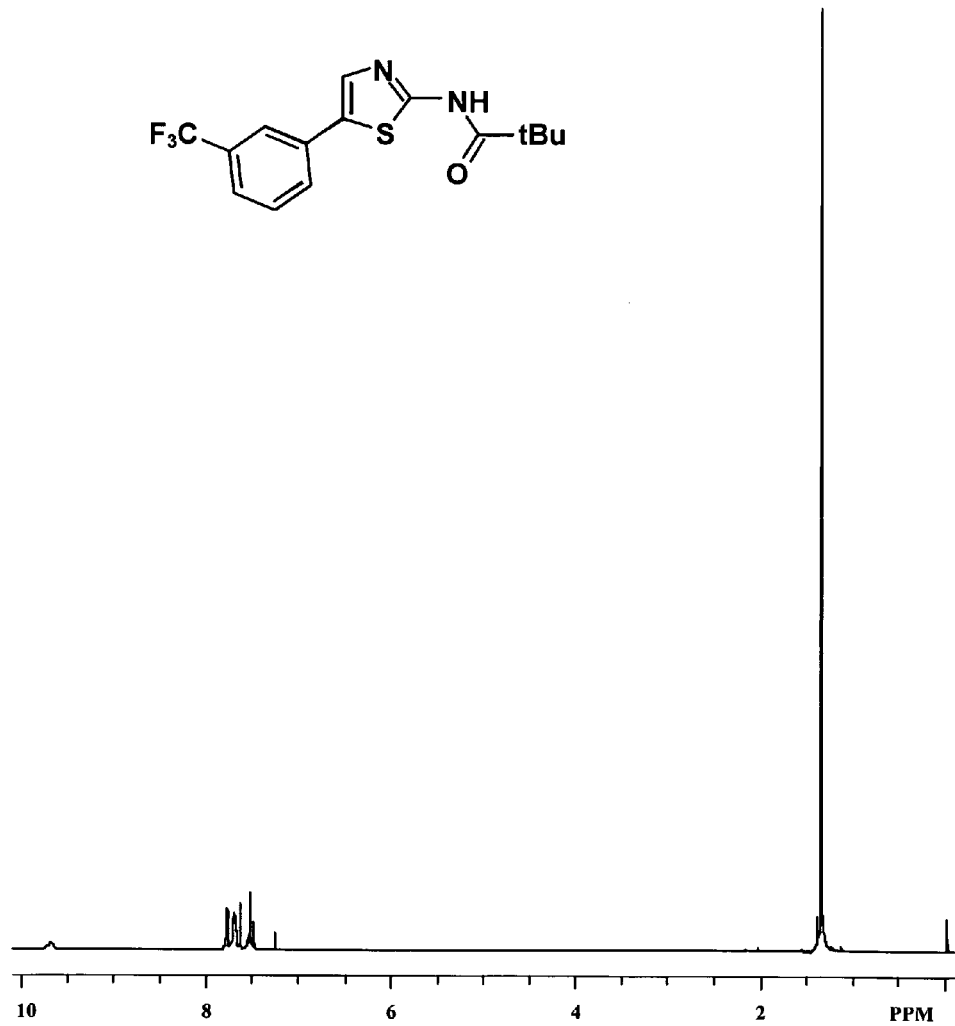
FIG. 14A depicts a $^1$H NMR spectrum of Entry 12 of Table I.
Figure 14B:
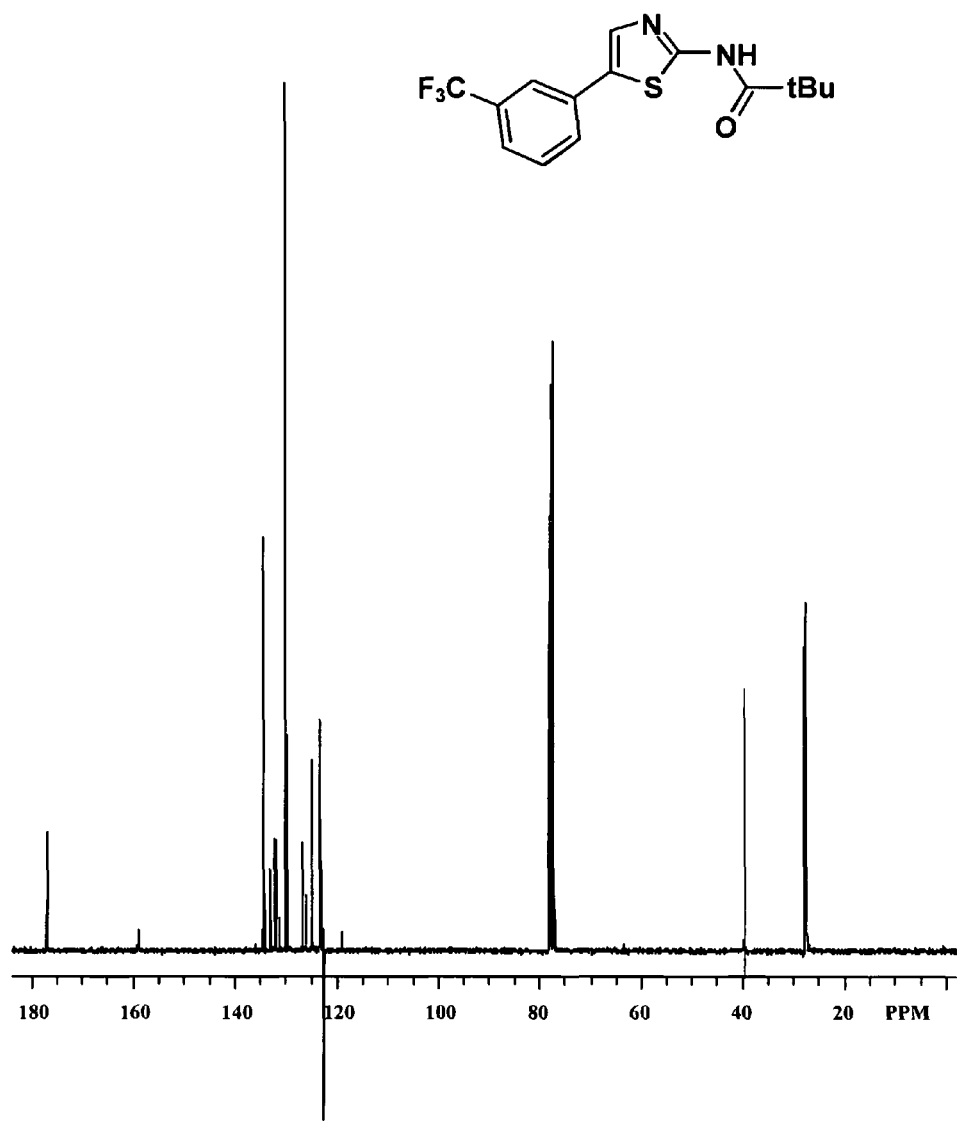
FIG. 14B depicts a $^{13}$C NMR spectrum of Entry 12 of Table I.

Palladium acetate (11.4 mg, 0.05 mmol), 2-pivaloylaminothiazole (184 mg, 1.0 mmol), 3-chlorobenzotrifluoride (271 mg, 1.5 mmol), butyldi-1-adamantylphosphine (38.5 mg, 0.1 mmol), $K_3PO_4$ (425 mg, 2.0 mmol) and anhydrous NMP (4 mL). After column chromatography (2/8 ethyl acetate/hexanes) 259 mg (79%) of white needles were obtained, mp 170-172° C. (2,2,4-trimethylpentane). $R_f$-0.91 (2/8 ethyl acetate/hexanes). ¹H NMR (300 MHz, $CDCl_3$) δ 1.36 (s, 9H), 7.47-7.77 (m, 5H), 9.69 (br, 1H). ¹³C NMR (75 MHz, $CDCl_3$) δ 27.7, 34.0, 123.2 (q, J-3.7 Hz), 124.3 (q, 277.6 Hz), 124.8 (q, J-3.9 Hz), 126.6, 129.7, 130.2, 132.1 (q, J-32.5 Hz), 133.2, 134.3, 159.0, 176.9. FT-IR (neat, $cm^1$) u 1679, 1337. Anal calcd for $C_{15}H_{15}F_3N_2OS$ (328.35 g/mol). C, 54.87; H, 4.60; N, 8.53. Found. C, 55.29; H, 4.91; N, 8.47. The in NMR and ¹³C NMR spectra are shown in FIGS. 14A&B, respectively.

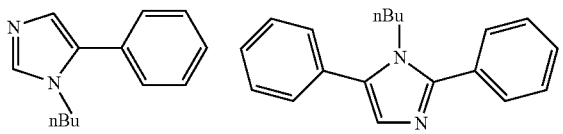

1-n-Butyl-2,5-Diphenylimidazole and 1-n-Butyl-5-Phenylimidazole (Entry 13, Table I)

Figure 15:
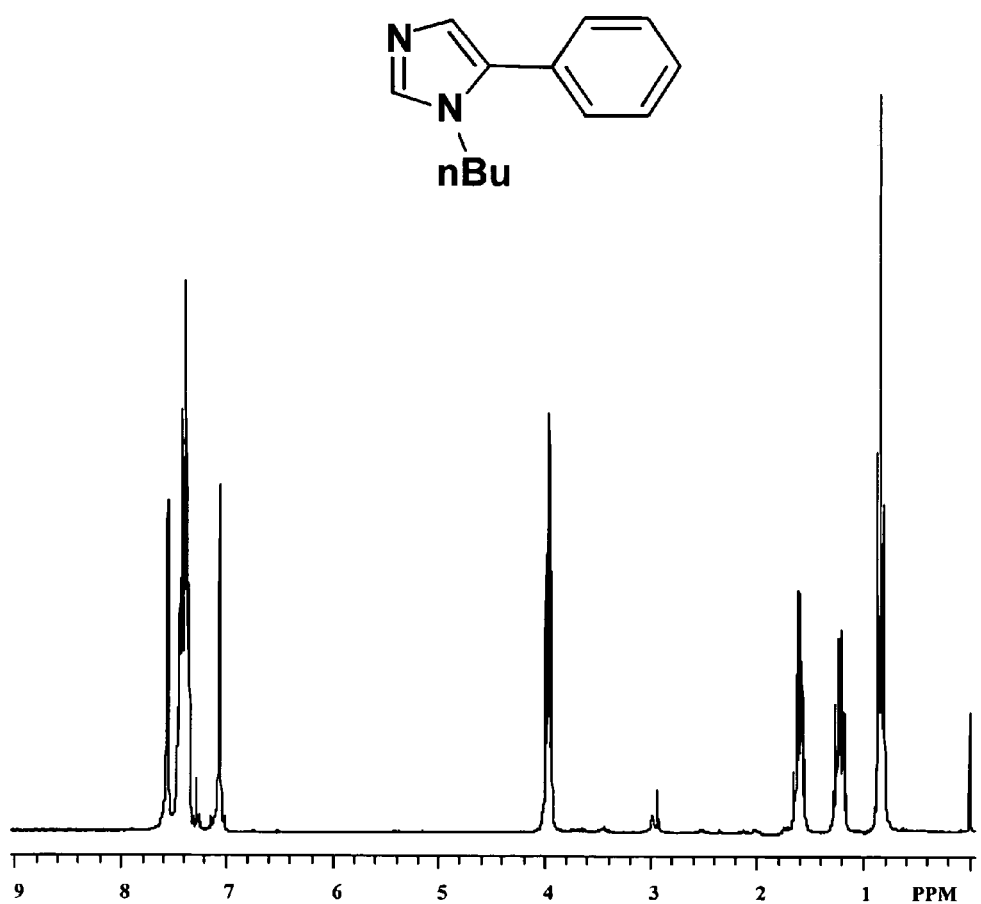
FIG. 15 depicts a $^1$H NMR spectrum of Entry 13 of Table I.
Figure 16A:
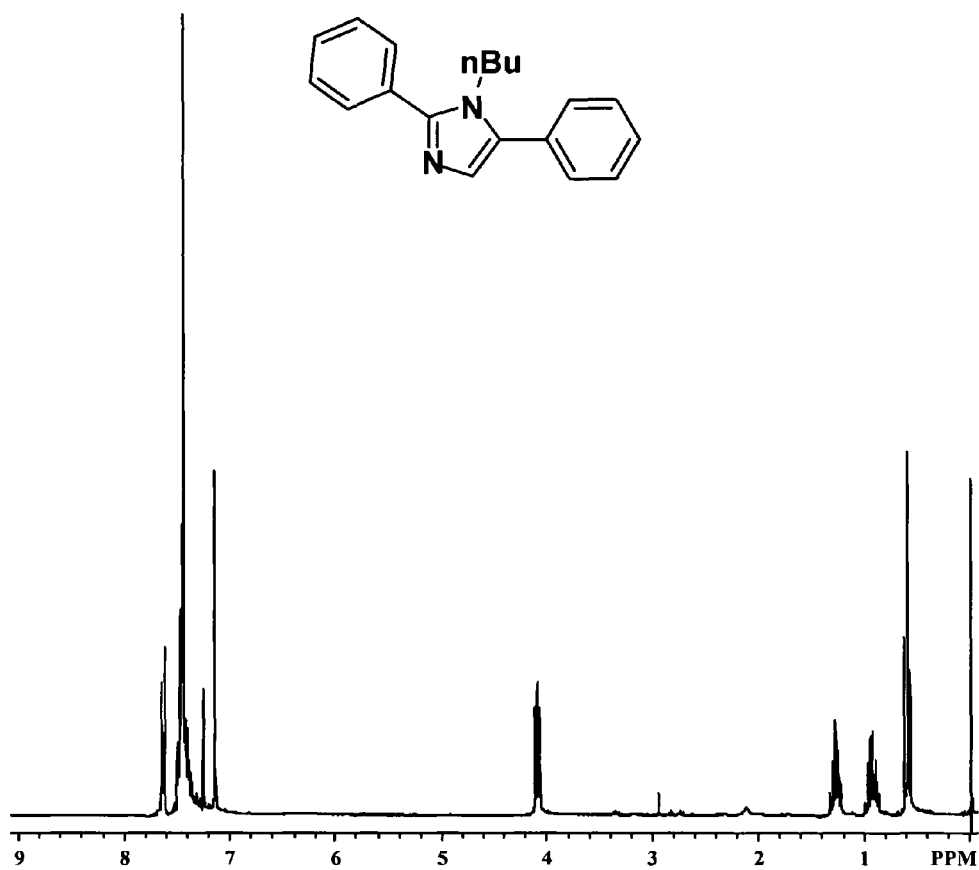
FIG. 16A depicts a $^1$H NMR spectrum of Entry 13 of Table I.
Figure 16B:
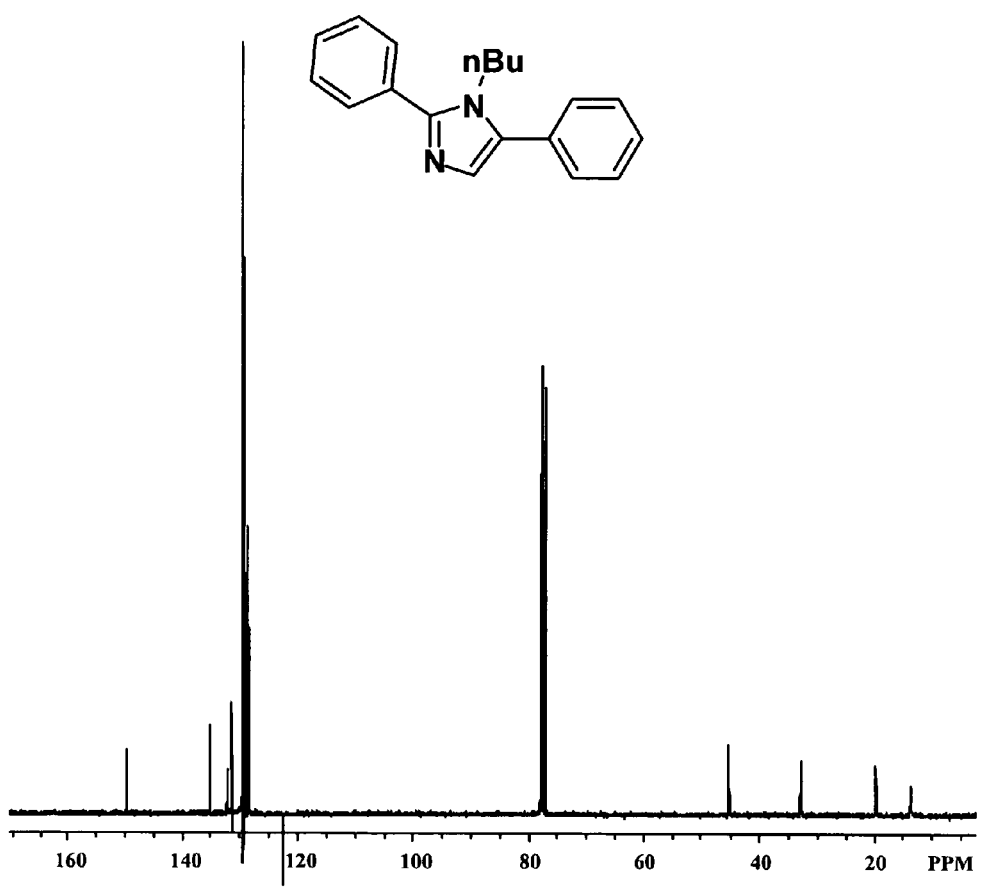
FIG. 16B depicts a $^{13}$C NMR spectrum of Entry 13 of Table I.

Palladium acetate (11.4 mg 0.05 mmol), 1-n-butylimidazole (124 mg, 1 mmol), chlorobenzene (169 mg, 1.5 mmol), butyl-di-1-adamantylphosphine (38.5 mg, 0.1 mmol), $K_3PO_4$ (425 mg, 2 mmol) and anhydrous NMP (4 mL). The purification was performed by preparative TLC (9/1 ethyl acetate/hexanes). Diphenylderivative was isolated as light tan crystals (36 mg, 13%), mp 124-126° C. (2,2,4-trimethylpentane). $R_f$-0.69 (9/1 ethyl acetate/hexanes). ¹H NMR (300 MHz, $CDCl_3$) δ 0.60 (t, J-6.9 Hz, 3H), 0.86-1.00 (m, 2H), 1.22-1.34 (m, 2H), 4.05-4.14 (m, 2H), 7.15 (s, 1H), 7.40-7.50 (m, 8H), 7.63-7.66 (m, 2H). ¹³C NMR (75 MHz, $CDCl_3$) 13.8, 19.8, 32.9, 45.3, 128.5, 128.6, 129.1, 129.2, 129.3, 129.5, 129.6, 131.4, 132.2, 135.0 149.7. FT-IR (neat, $cm^1$) u 1464. Monophenylated derivative was isolated by extraction of the appropriate band with chloroform followed by washing with 10% $NaHCO_3$ (3×1 mL) and filtration. After drying, colorless oil was obtained, 104 mg (52%). $R_f$-0.38 (9/1 ethyl acetate/hexanes). This compound is known.[11] ¹H NMR (300 MHz, $CDCl_3$) δ 0.83 (t, J-7.5 Hz, 3H), 1.14-1.32 (m, 2H), 1.53-1.68 (m, 2H), 3.90-4.04 (m, 2H), 7.06 (br s, 1H), 7.35-7.45 (m, 5H), 7.55 (br s, 1H). The ¹H NMR spectrum for the monoarylated product is shown in FIG. 15 and the ¹H NMR and ¹³C NMR spectra of the diarylated product are shown in FIGS. 16A&B, respectively.

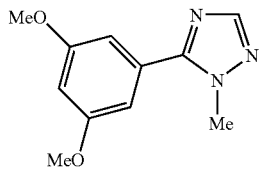

5-(3,5-Dimethoxyphenyl)-1-Methyl-1H-1,2,4-Triazole (Entry 14 Table I)

Figure 17:
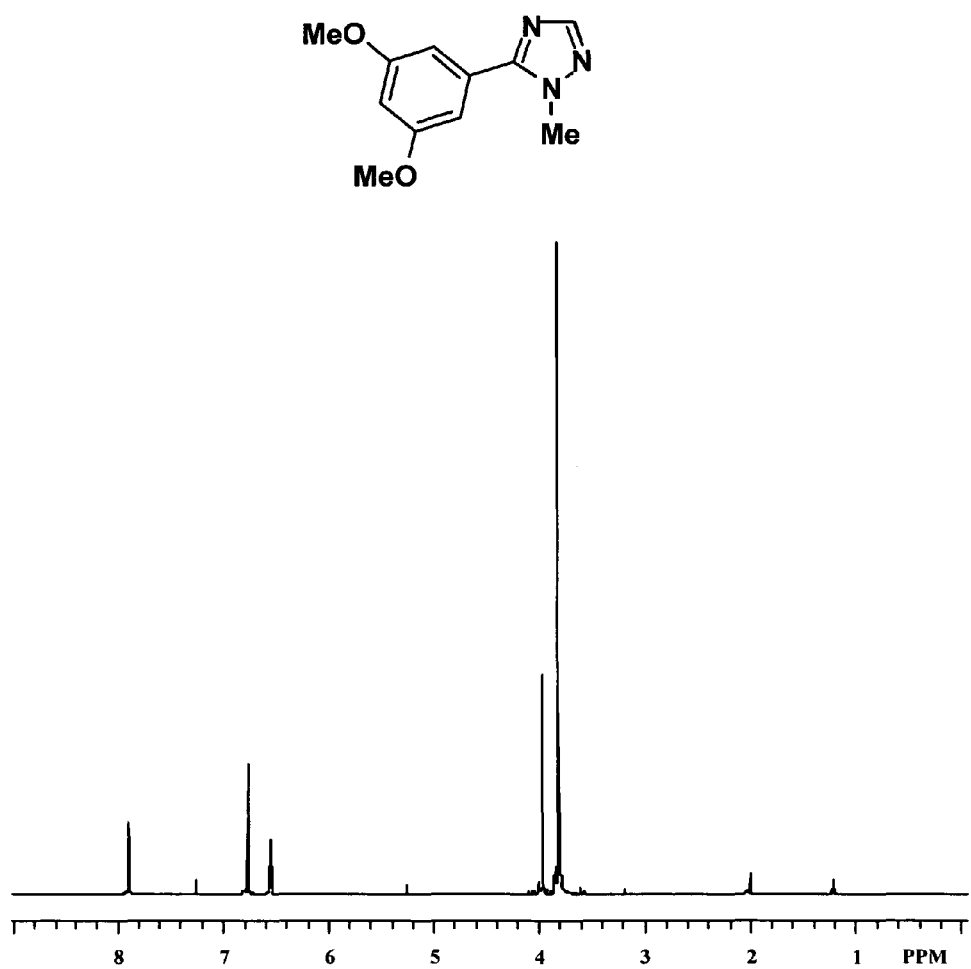
FIG. 17 depicts a $^1$H NMR spectrum of Entry 14 of Table I.

Palladium acetate (11.4 mg, 0.05 mmol), 1-methyl-1,2,4-triazole (83 mg 1.0 mmol), 5-chloro-1,3-dimethoxybenzene (259 mg, 1.5 mmol), butyldi-1-adamantylphosphine (38.5 mg, 0.1 mmol), $K_3PO_4$ (425 mg, 2.0 mmol) and anhydrous NMP (4 mL). After column chromatography (1/1 ethyl acetate/hexanes) 167 mg (76%) of light tan crystals were obtained. This compound is known.[12] ¹H NMR (300 MHz, $CDCl_3$) δ 3.81 (s, 6H), 3.97 (s, 3H), 6.55 (t, J-2.1 Hz, 1H), 6.76 (d, J-2.1 Hz, 2H), 7.90 (s, 1H). The ¹H NMR spectrum is shown in FIG. 17.

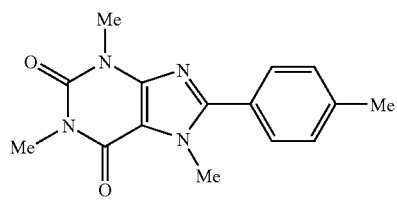

8-[4-Methylphenyl]-3,7-Dihydro-1,3,7-Trimethyl-1H-Purine-2,6-dione (Entry 15, Table I)

Figure 18A:
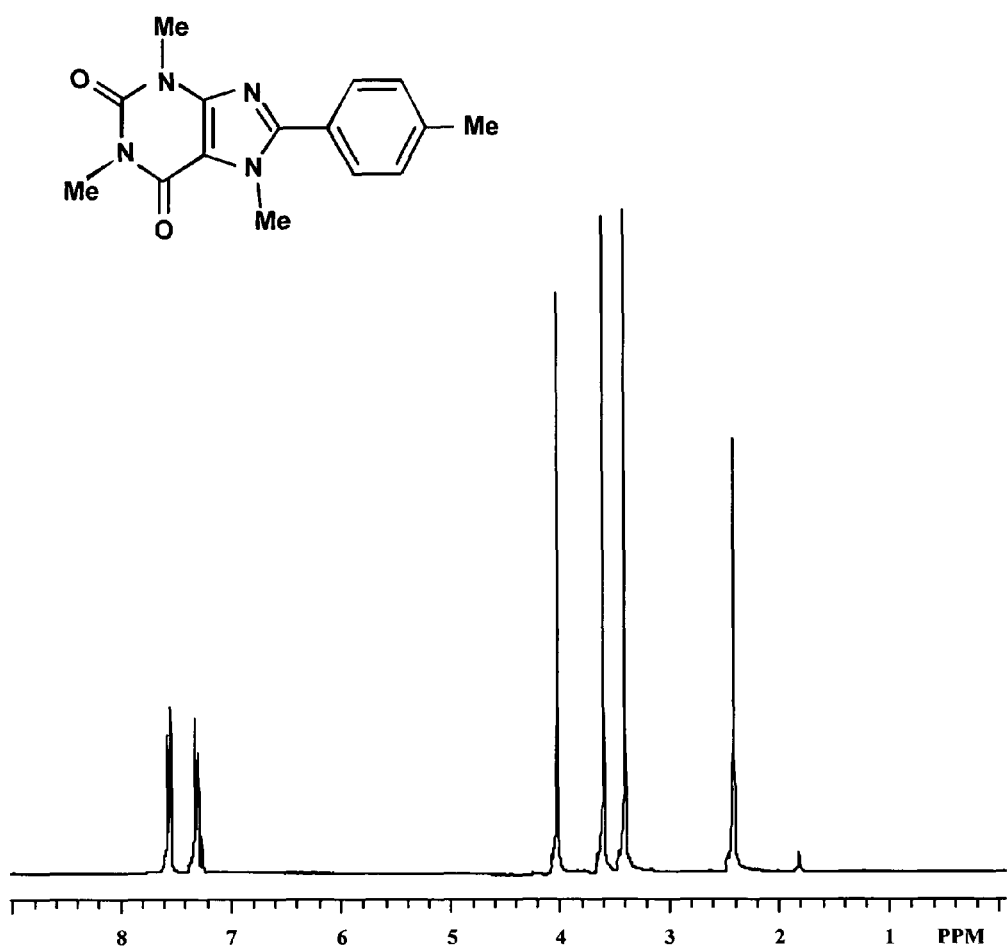
FIG. 18A depicts a $^1$H NMR spectrum of Entry 15 of Table I.
Figure 18B:
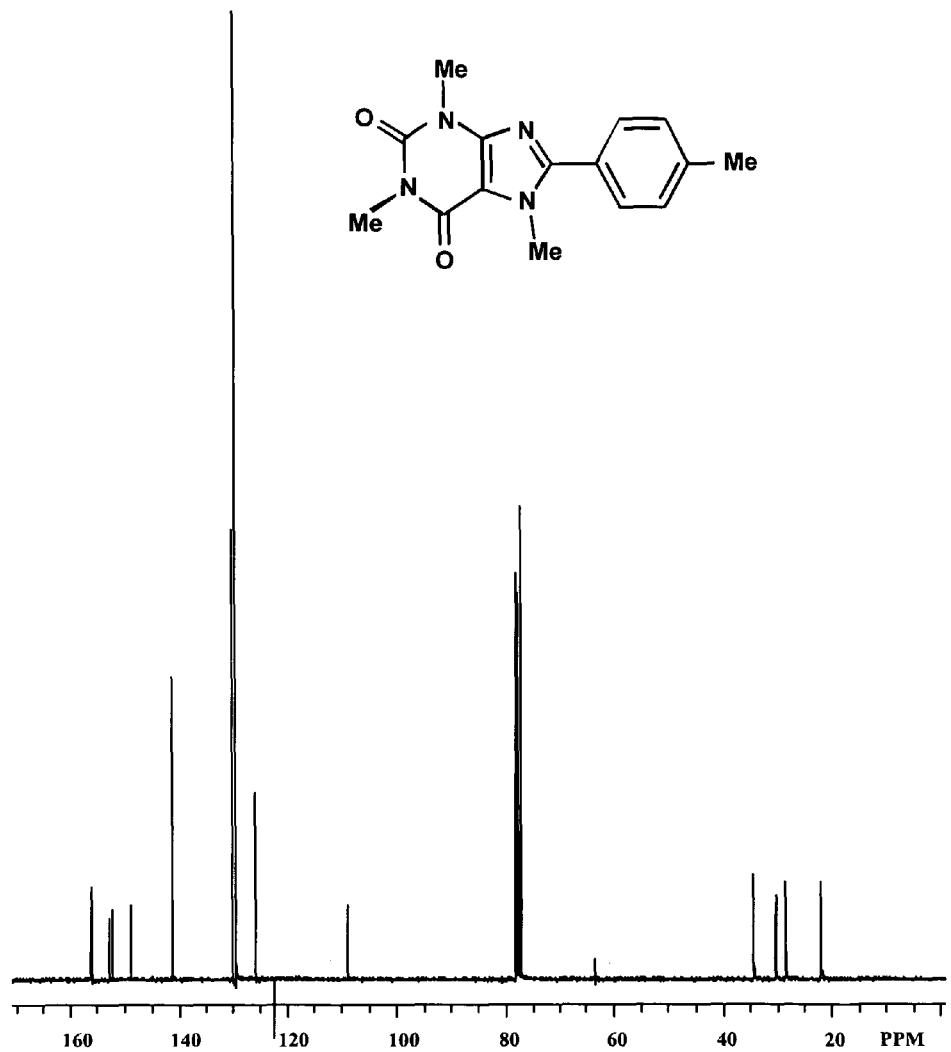
FIG. 18B depicts a $^{13}$C NMR spectrum of Entry 15 of Table I.

Palladium acetate (11.4 mg, 0.05 mmol), caffeine (194 mg, 1.0 mmol), 4-chlorotoluene (190 mg, 1.5 mmol), butyldi-1-adamantylphosphine (38.5 mg, 0.1 mmol), $K_3PO_4$ (425 mg, 2.0 mmol) and anhydrous NMP (4 mL). After column chromatography (7/3 ethyl acetate/hexanes) 244 mg (86%) of a white solid was obtained, mp 193-194° C. (acetone). $R_f$-0.57 (8/2 ethyl acetate/hexanes). $^1$H NMR (300 MHz, CDCl$_3$) δ 2.41 (s, 3H), 3.40 (s, 3H), 3.60 (s, 3H), 4.02 (s, 3H), 7.30 (d, J-8.0 Hz, 2H), 7.56 (d, J-8.0 Hz, 2H). $^{13}$C NMR (75 MHz, CDCl$_3$) δ 22.0, 28.5 30.3, 34.4, 108.9, 122.5, 129.6, 130.1, 141.2, 148.8, 152.3, 152.8, 156.1. FT-IR (neat, cm$^1$) u 1692, 1651. Anal calcd for C$_{15}$H$_{16}$N$_4$O$_2$ (284.31 g/mol): C, 63.37; H, 5.67; N, 19.71. Found. C, 63.58; H, 5.67; N, 19.72. The $^1$H NMR and $^{13}$C NMR spectra are shown in FIGS. 18A&B, respectively.

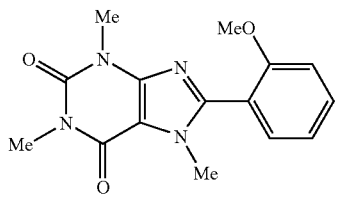

8-[2-Methoxyphenyl]-3,7-Dihydro-1,3,7-Trimethyl-1H-Purine-2,6-dione Entry 16, Table I)

Figure 19A:
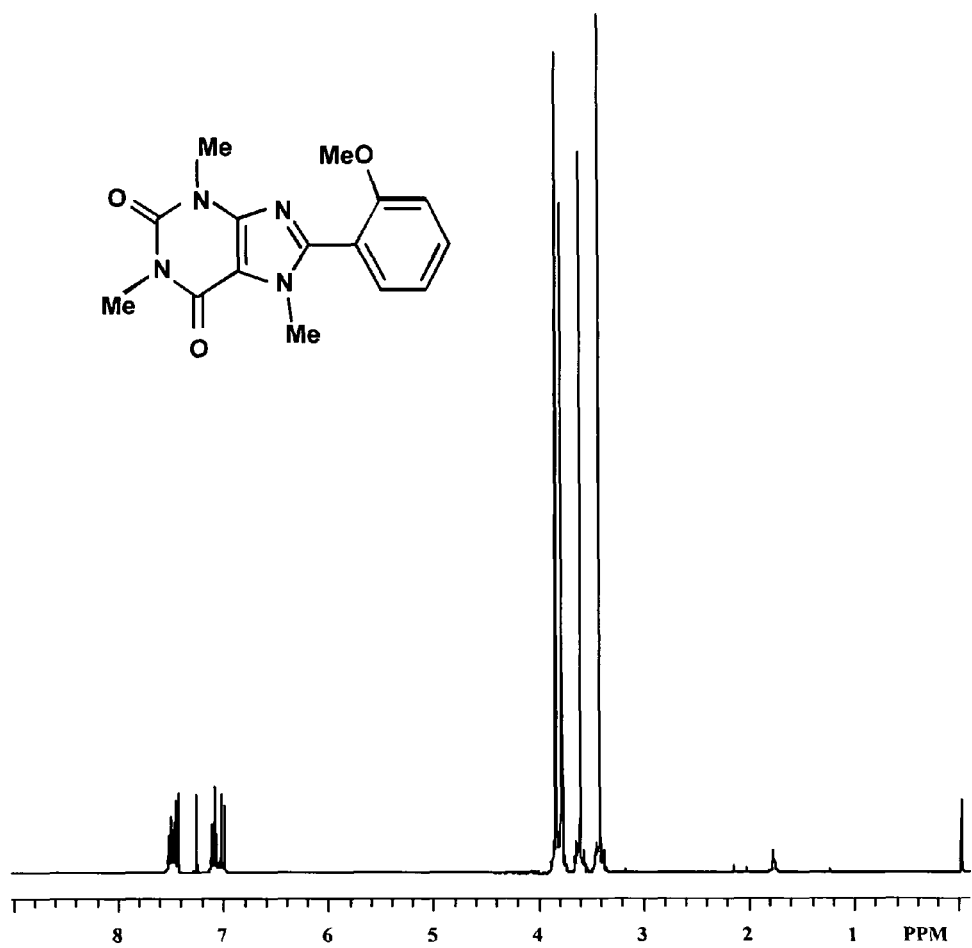
FIG. 19A depicts a $^1$H NMR spectrum of Entry 16 of Table I.
Figure 19B:
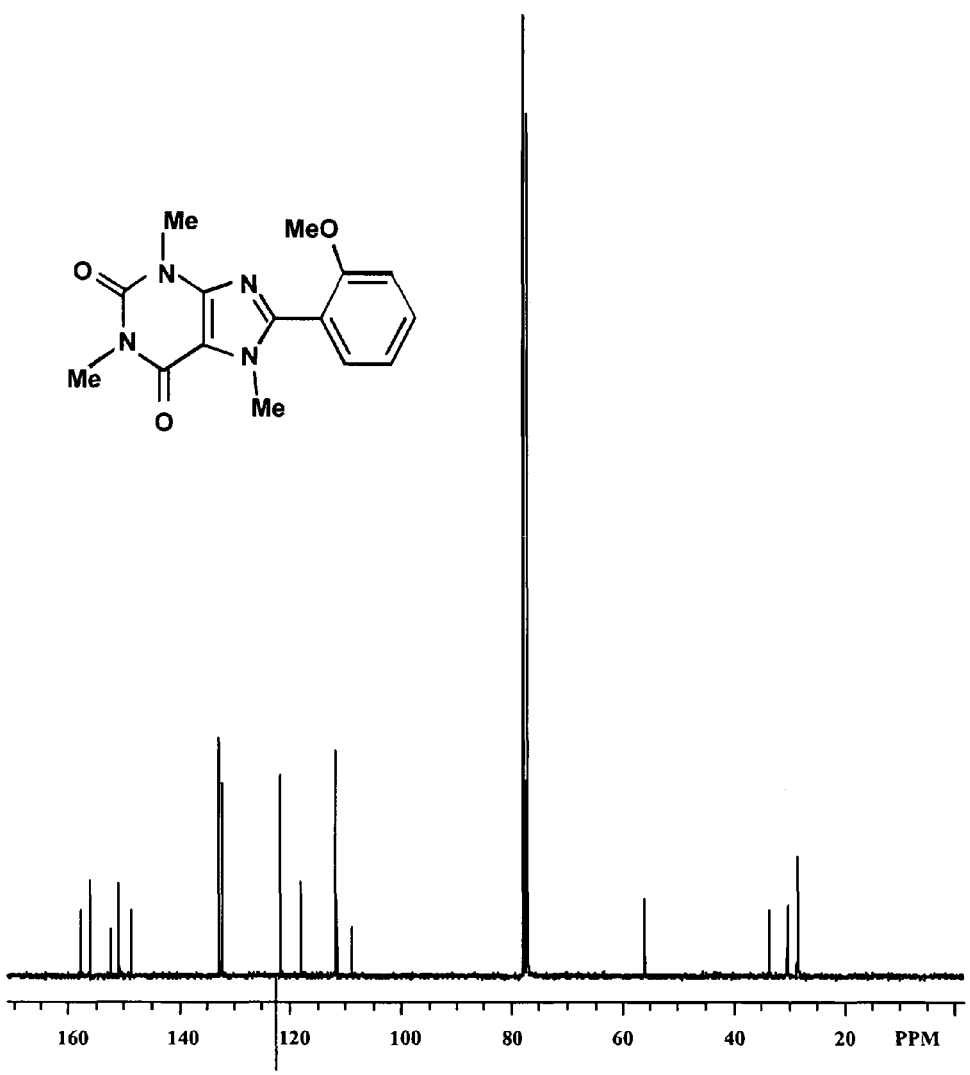
FIG. 19B depicts a $^{13}$C NMR spectrum of Entry 16 of Table I.

Palladium acetate (11.4 mg, 0.05 mmol), caffeine (194 mg, 1.0 mmol), 2-chloroanisole (450 mg, 1.5 mmol), butyldi-1-adamantylphosphine (38.5 mg, 0.1 mmol), K$_3$PO$_4$ (425 mg, 2.0 mmol) and anhydrous NMP (4 mL). After column chromatography (7/3 ethyl acetate/hexanes) 213 mg (71%) of a white solid was obtained, mp 236-237° C. (acetone). $R_f$-0.62 (65/35 ethyl acetate/hexanes). $^1$H NMR (300 MHz, CDCl$_3$) δ 3.46 (s, 3H), 3.64 (s, 3H), 3.82 (g, 3H), 3.87 (5, 3H), 7.04 (d, J-8.4 Hz, 1H), 7.1 (t, J-7.0 Hz, 1H), 7.47-7.55 (m, 2H). $^{13}$C NMR (75 MHz, CDCl$_3$) δ 28.5, 30.3, 33.6, 56.1, 108.8, 111.7, 118.1, 121.7, 132.5, 132.8, 148.7, 150.9, 152.3, 156.1, 157.9. FT-IR (neat, cm$^1$) u 1704, 1668. Anal calcd for C$_{15}$H$_{16}$N$_4$O$_3$ (300.31 g/mol): C, 59.99; H, 5.37; N, 18.66. Found. C, 60.02; H, 5.42; N, 18.61. The $^1$H NMR and $^{13}$C NMR spectra are shown in FIGS. 19A&B, respectively.

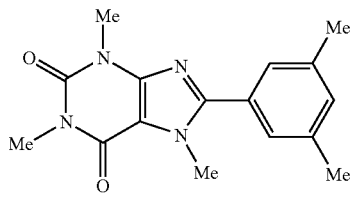

8-[3,5-Dimethylphenyl]-3,7-Dihydro-1,3,7-Trimethyl-1H-Purine-2,6-dione (Entry 17, Table I)

Figure 20A:
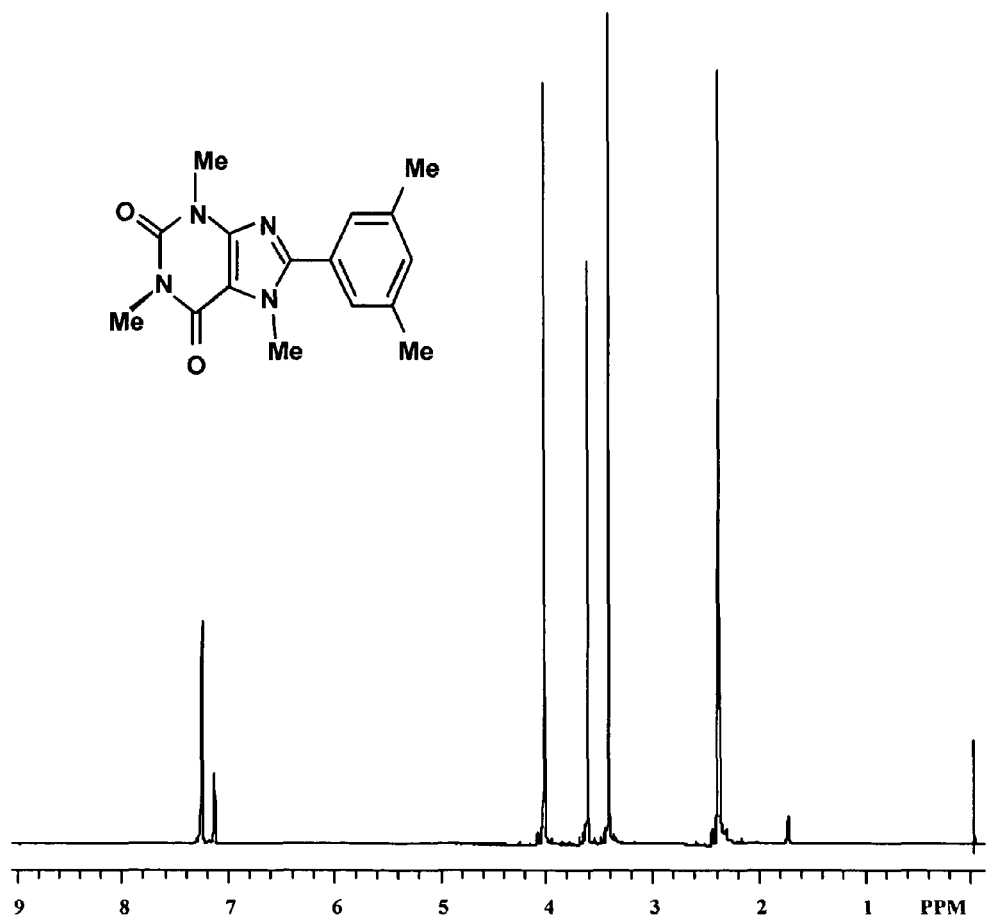
FIG. 20A depicts a $^1$H NMR spectrum of Entry 17 of Table I.
Figure 20B:
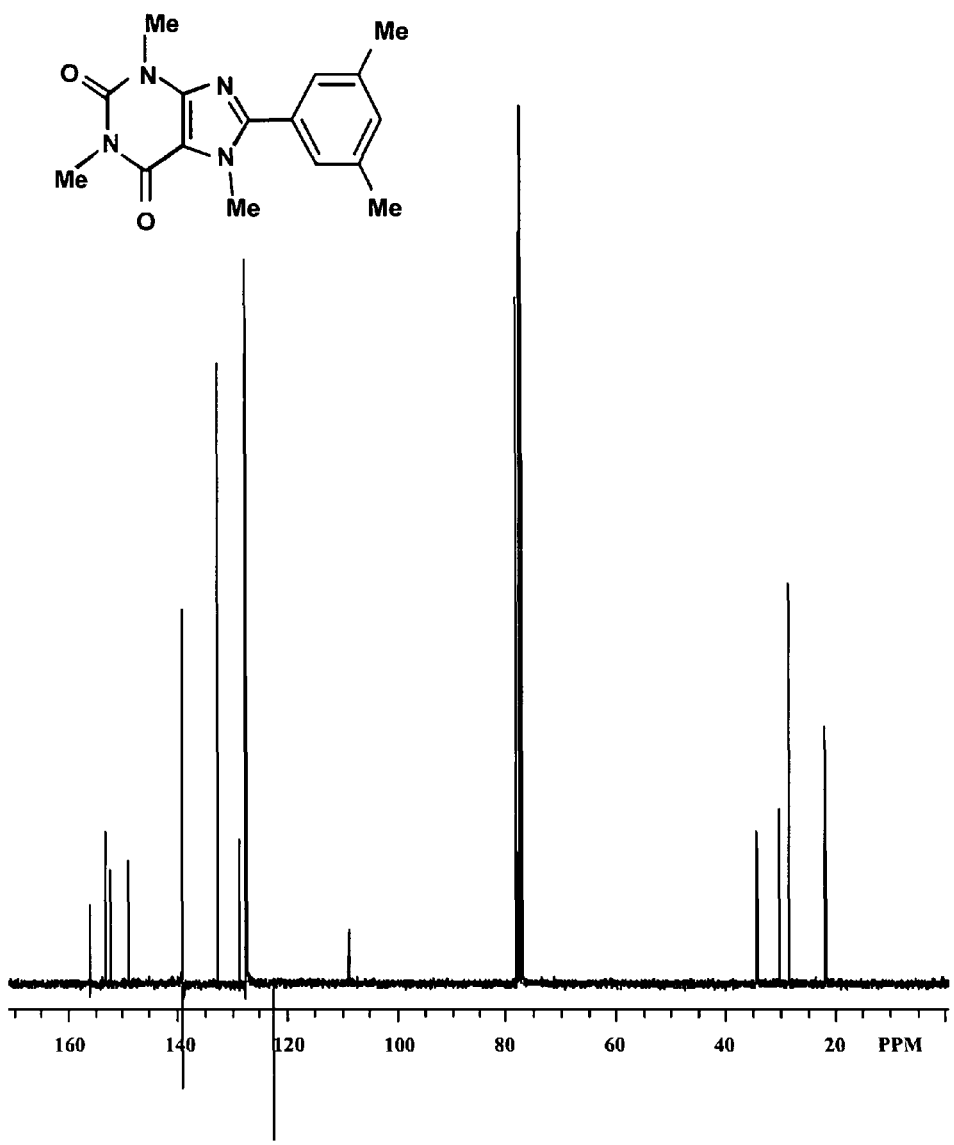
FIG. 20B depicts a $^{13}$C NMR spectrum of Entry 17 of Table I.

Palladium acetate (11.4 mg, 0.05 mmol), caffeine (194 mg, 1.0 mmol), 5-chloro-m-xylene (211 mg, 1.5 mmol), butyldi-1-adamantylphosphine (38.5 mg, 0.1 mmol), K$_3$PO$_4$ (425.0 mg, 2.0 mmol), and anhydrous NMP (4.0 mL). After column chromatography (7/3 ethyl acetate/hexanes) 230 mg (77%) of a white solid was obtained, mp 210-211° C. (acetone). $R_f$-0.65 (7/3 ethyl acetate/hexanes). $^1$H NMR (300 MHz, CDCl$_3$) δ 2.38 (s, 6H), 3.42 (s, 3H), 3.61 (s, 3H), 4.02 (s, 3H), 7.13 (s, 1H), 7.25 (s, 2H). $^{13}$C NMR (75 MHz, CDCl$_3$) δ 21.9, 28.5, 30.3, 34.4, 108.9, 127.4, 128.7, 132.6, 139.2, 148.8, 152.3, 153.1, 156.1. FT-IR (neat, cm$^1$) u 1693, 1657. Anal calcd for C$_{16}$H$_{18}$N$_4$O$_2$ (298.34 g/mol): C, 64.41; H, 6.08; N, 18.78. Found. C, 64.41; H, 6.13; N, 18.91. The $^1$H NMR and $^{13}$C NMR spectra are shown in FIGS. 20A&B, respectively.

B. Optimization of Conditions

General Procedure

Outside the glovebox a 2-dram vial equipped with a magnetic stir bar was charged with Pd(OAc)$_2$ (5 mol %), 1-n-butylimidazole (0.5 mmol) and chlorobenzene (3 mmol). The vial was flushed with argon, capped and placed inside a glovebox. To this mixture was added ligand (10 mol % with respect to imidazole), base (2 mmol), MS 3 Å (155 mg and solvent. The sealed vial was taken out of the glove box, stirred at room temperature for 15 min and placed in a preheated oil bath (125° C.) for 16-17 h. After cooling the reaction mixture to room temperature, hexadecane internal standard was added (~50 µL). An aliquot of the mixture was diluted with ethyl acetate (1 mL) and used in determination of conversion by GC. The response factor was determined by a separate injection of a known mixture of starting material and internal standard.

TABLE IV

Evaluation of Phosphine Ligands[a]

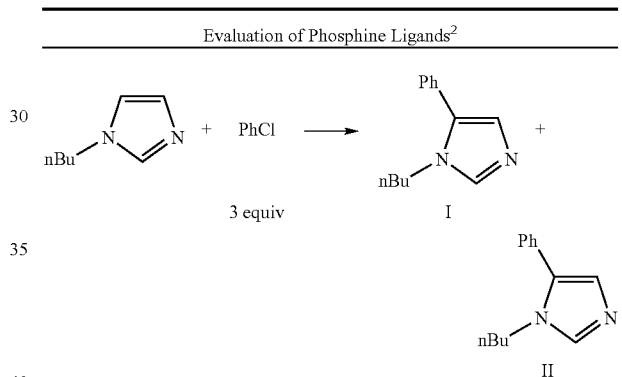

| Entry | Ligand, 10 mol % | % I | % II |
|---|---|---|---|
| A1 | nBuAd$_2$P | 40 | 12 |
| A2 | tBu$_2$bP-P[b] | 20 | 6 |
| A3 | tBuCy$_2$P | 45 | 16 |
| A4 | IPr-HC[c] (5 mol %) + KtBuO (10 mol %) | 12 | 4 |
| A5 | Ad$_2$POH | 10 | 3 |

[a]Conditions: 5 mol % Pd(OAc)$_2$, 2 equiv Cs$_2$CO$_3$, 155 mg MS 3Å, 2.5 ml dry DMF, stir for 15 min at RT then for 16 h at 125
[a]C. Conversions were determined by GC using hexadecane as an internal standard.
[b]2-(di-t-Butylphosphino)biphenyl.
[c]1,3-Bis-(2,6-i-propylphenyl)-4,5-dihydroimidazolium chloride.

TABLE V

Evaluation of Base[a]

| Entry | Base, 2 equiv | % I | % II |
|---|---|---|---|
| B1 | CsOAc | 40 | 5 |
| B2 | CsF | 48 | 5 |
| B3 | K$_3$PO$_4$ | 51 | 7 |
| B4 | K$_2$CO$_3$ | 41 | 7 |
| B5 | Cs$_2$CO$_3$ | 45 | 16 |

[a]Conditions: 5 mol % Pd(OAc)$_2$, 10 mol % t-BuCy$_2$P, 155 mg MS 3 Å, 2.5 ml dry DMF, stir for 15 min at RT, then for 16 h at 125° C. Conversions were determined by GC using hexadecane as an internal standard.

TABLE VI

Evaluation of Pd Source[a]

| Entry | Pd source, 5 mol % | % I | % II |
|---|---|---|---|
| C1 | Pd$_2$dba$_2$-CHCl$_3$ | 8 | 1 |
| C2 | Pd/C 10% | 2 | 0 |
| C3 | Pd(OCOCF$_3$)$_2$ | 1 | 0 |
| C4 | PdCl$_2$ | 11 | 1 |
| C5 | Pd(OAc)$_2$ | 51 | 7 |

[a]Conditions: 10 mol % t-BuCy$_2$P, 2 equiv K$_3$PO$_4$, 155 mg MS 3 Å, 2.5 ml dry DMF, stir for 15 min at RT then for 16 h at 125° C. Conversions were determined by GC using hexadecane as internal standard.

TABLE VII

Evaluation of Solvent[a]

| Entry | Solvent, 2.5 mL | % I | % II |
|---|---|---|---|
| D1 | Toluene | 13 | 3 |
| D2 | DMSO | 8 | 1 |
| D3 | NMP | 65 | 9 |
| D4 | tBuOH | 26 | 6 |
| D5 | DMF | 51 | 7 |

[a]Conditions: 5 mol % Pd(OAc)$_2$, 10 mol % t-BuCy$_2$P, 2 equiv K$_3$PO$_4$, 155 mg MS 3 Å, stir for 15 min at RT, then for 16 h at 125° C. Conversions were determined by GC using hexadecane as internal standard.

TABLE VIII

Selection of Final Conditions[a]

| Entry | Comparison at 3.5 mol % Pd(OAc)$_2$ | % I | % II |
|---|---|---|---|
| E1 | t-BuCy$_2$P, MS 3 Å, NMP | 32 | 3 |
| E2 | t-BuCy$_2$P, NMP | 34 | 4 |
| E3 | t-BuCy$_2$P, DMA | 47 | 9 |
| E4 | n-BuAd$_2$P, DMA | 54 | 16 |
| E5 | n-BuAd$_2$P, NMP | 52 | 11 |
| E6 | t-Bu$_2$MeP, DMA | 19 | 5 |

[a]Conditions: 3.5 mol % Pd(OAc)$_2$, 2 equiv K$_3$PO$_4$, stir for 15 min at RT the for 17 h at 125° C. Conversions were determined by GC using hexadecane as internal standard.

C. Comparison of the Reactivity of Ph-X with Benzothiazole

TABLE IX

Comparison of the Yields with Different Ph-X[a]

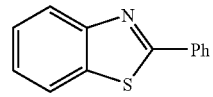

| Ph-X | % product |
|---|---|
| Ph-Cl | 27 |
| Ph-Br | 21 |
| Ph-I | 13 |
| Ph-OTf | 39 |

[a]Conditions: 1 equiv benzothiazole, 10 equiv ArX 5 mol % Pd(OAc)$_2$, 2 equiv K$_3$PO$_4$, stir for 15 min RT, then 1 h 125° C. Product is 2-phenylbenzothiazole. Yields were determined by GC using hexadecane as an internal standard. Average of two runs.

D. Determination of Kinetic Isotope Effects (KIE)

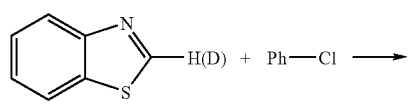

Outside the glovebox a 2-dram vial equipped with a magnetic stir bar was charged with Pd(OAc)$_2$ (5 mol %), benzothiazole (2-H or 2-D) (0.5 mmol) and chlorobenzene (5 mmol). The vial was flushed with argon, capped and placed inside a glovebox. To this mixture was added butyldi-1-adamantylphosphine (10 mol %), K$_3$PO$_4$ (2 mmol) and anhydrous NMP (2 mL). The sealed vial was taken out of the glovebox, stirred at room temperature for 15 min and placed in a preheated oil bath (125° C.) for the designated time (1, 2, 3, or 4 hours). After cooling the reaction mixture (room temperature), a weighed amount of hexadecane internal standard was added (~50 µl). An aliquot of the reaction mixture was diluted with ethyl acetate (1 mL) and used in the determination of conversion by GC. The log (SMi/SMf) versus time was plotted (SM$_i$=mmol starting material introduced into reaction; SM$_f$=mmol starting material left unreacted after time t).

TABLE X

Reaction of 2-H-Benzothiazole with PhCl versus Time (hours)
Benzothiazole (2-H)

| t, hour | SM$_i$ | SM$_f$ | log (SM$_i$/SM$_f$) |
|---|---|---|---|
| 0 | 0.500 | 0.50 | 0.000 |
| 1 | 0.506 | 0.30 | 0.232 |
| 2 | 0.503 | 0.23 | 0.349 |
| 3 | 0.517 | 0.12 | 0.634 |
| 4 | 0.503 | 0.08 | 0.817 |

Referring now to FIG. 1, a graph of the reaction of 2-H-benzothiazole with PhCl versus time (h) is shown.

TABLE XI

Reaction of 2-D-Benzothiazole with PhCl versus Time (h)
Benzothiazole (2-D)

| t, hour | SM$_i$ | SM$_f$ | log (SM$_i$/SM$_f$) |
|---|---|---|---|
| 0 | 0.500 | 0.500 | 0.000 |
| 1 | 0.506 | 0.330 | 0.188 |
| 2 | 0.502 | 0.270 | 0.274 |
| 3 | 0.504 | 0.150 | 0.537 |
| 4 | 0.504 | 0.130 | 0.593 |

Figure 2:
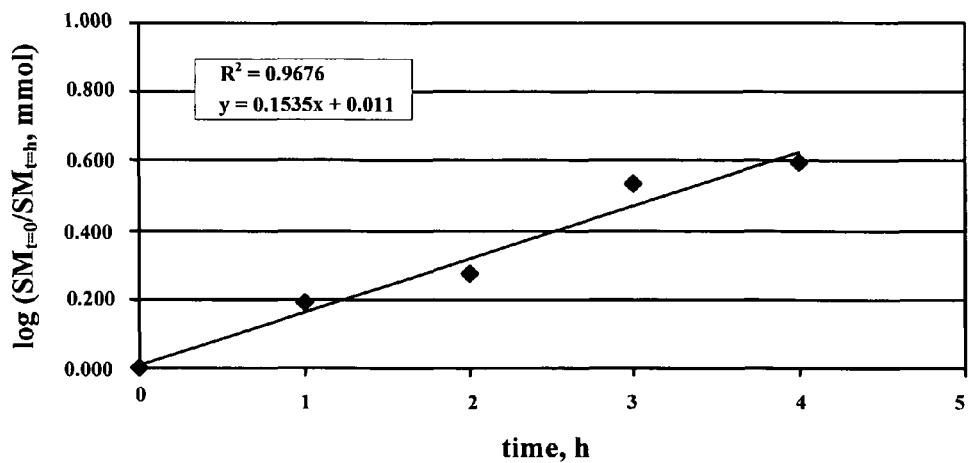
FIG. 2 depicts a graph of the reaction of 2-D-benzothiazole with PhCl versus time (h).

Referring now to FIG. 2, a graph of the reaction of 2-D-benzothiazole with PhCl versus time (h). From the date in Tables X and XI and graphed in FIGS. 1 and 2 yield a calculated kinetic isotope of k$_H$/k$_D$=0.2036/0.1535=1.33.

REFERENCES CITED IN EXPERIMENTAL SECTION I

1. Smith, G. G.; Jones, D. A.; Brown, D. F. *J. Org. Chem* 1963, 28, 403.
2. Schiavi, B.; Ahond, A.; Al-Mourabit, A; Poupat, C.; Chiaroni, A.; Gaspard, C.; Potier, P. *Tetrahedron* 2002, 58, 4201.
3. Chikashita, H.; Komazawa, S.; Ishimoto, N.; Inoue, K.; Itoh, K. *Bull. Chem. Soc. Jpn.* 1989, 62, 1215.
4. Commercially available from Oakwood Chemicals, CAS No. 886502-83-6

5. Pivsa-Art, S.; Satoh, T.; Kawamura, Y.; Miura, M.; Nomura, M. *Bull. Chem. Soc. Jpn.* 1998, 71, 467.
6. Labadie, S. S. *Synth. Commun.* 1994, 24, 709.
7. Dao, L. H.; Maleki, M.; Hopkinson, A. C.; Lee-Ruff, E. *J. Am. Chem. Soc.* 1986, 108, 5237
8. Bayh, O.; Awad, H.; Mongin, F.; Hoarau, C.; Bischoff, L.; Trecourt, F.; Queguiner, G.; Marsais, F.; Blanco, F.; Abarca, B.; Ballesteros, R. *J. Org. Chem.* 2005, 70, 5190.
9. Rips, R.; Lachaize, M.; Albert, O.; Dupont, M. *Chimica Therapetica* 1971, 6, 126.
10. Laskar, I. R.; Chen, T.-M. *Chem. Mater.* 2004, 16, 111.
11. Kashima, C.; Harada, Y.; Hosomi, A. *Heterocycles* 1993, 35, 433.
12 Y.; Lang, S. A.; Lovell, M. F.; Perkinson, N. A. *J. Org. Chem.* 1979, 44, 4160.

Experimental Section II

Two Methods for Direct Ortho-Arylation of Benzoic Acids

General Considerations

Reactions were performed in 2-dram vials with PTFE caps. Flash chromatography was performed on 60 Å silica gel (Sorbent Technologies). Purification by preparative HPLC was performed on a Shimadzu Prominence LC (LC-20AB) equipped with a SPD-20A UV-Vis detector and a Varian Dynamax (250 mm×21.4 mm; Microsorb 100 Si packing) column. All preparative HPLC runs were performed using 2% acetic acid in hexanes as an eluent. GC analyses were performed on a Shimadzu CG-2010 chromatograph equipped with a Restek column (Rtx®-5, 15 m, 0.25 mm ID). The $^1$H, $^{13}$C and $^{19}$F NMR spectra were recorded on a GE QE-300 spectrometer using residual solvent peak (for $^1$H and $^{13}$C-NMR) and $C_6F_6$ ($^{19}$F) as reference. Melting points were measured on a Mel-Temp apparatus and are uncorrected. Elemental analyses were performed by Atlantic Microlab Inc. of Norcross, Ga. IR spectra were obtained using ThermoNicolet Avatar 370 FT-IR instrument.

Materials

Palladium acetate was obtained from J&J Materials and was used as received. Molecular sieves 3 Å (Aldrich) were flame dried under reduced pressure and stored under argon. Powdered $Cs_2CO_3$ (Strem), anhydrous DMF (Fluka or Aldrich) and butyldi-1-adamantylphosphine (Strem) were stored under argon. The following starting materials were obtained from commercial sources and were used without further purification: 4-(trifluoromethyl)benzoic acid, 3-fluorobenzoic acid, 3-(trifluoromethyl)benzoic acid, 4-chlorobenzotrifluoride, 4-chloroiodobenzene, 3-iodotoluene, 3,5-dichloroiodobenzene, 1-chloro-3-fluorobenzene, biphenyl-3-carboxylic acid and bis-3,5-(trifluoromethyl iodobenzene (Oakwood Products); mono-methyl terephthalate, 5-iodo-m-xylene, 2-biphenylcarboxylic acid, and 3-chlorotoluene (Acros); (trimethylsilyl)diazomethane (2.0 M in hexanes), lithium wire in mineral oil, deuterium oxide and 3,4-dimethylbenzoic acid (Aldrich); 2-methylbenzoic acid and 4-methylchlorobenzene (Matheson); 3-nitrobenzoic acid, mono-methyl isophthalate, 2-bromotoluene, 1-iodo-4-isopropylbenzene, and 3,4-dimethoxybenzoic acid (Alfa Aesar); 3-methylbenzoic acid, 2-naphthoic acid, and 3-bromobenzoic acid (Eastman) 3-Isopropoxybenzoic acid is known.[1a] Silver acetate was prepared as described before.1b General Procedure for Coupling of Iodoarenes with Benzoic Acids Without special precautions, a 2-dram vial equipped with a magnetic stir bar was charged with $Pd(OAc)_2$ (5 mol %), silver acetate (1.3 equiv), $ArCO_2H$ (1 equiv), iodoarene (3 equiv) and acetic acid (200 μL per mmol $ArCO_2H$). The sealed vial was placed in a preheated oil bath (100-130° C.) and heated until all benzoic acid starting material had been consumed as determined by TLC or GC (4.5 to 7 h). The reaction mixture was allowed to cool to room temperature, diluted with dichloromethane (2 mL) and filtered through a pad of Celite®. The reaction vessel and Celite® pad were rinsed with dichloromethane (2×1 mL). The filtrate was concentrated under reduced pressure and the residue suspended in 5% aqueous KOH. The mixture was extracted with dichloromethane (3×10 mL), the aqueous layer was acidified with concentrated HC to pH-2 followed by extraction with dichloromethane (3×10 mL). After filtering through a pad of Celite® the dichloromethane layer was concentrated to a volume of about 2 mL. The mixture was adsorbed on silica gel and was subjected to flash chromatography (hexanes then dichloromethane-ethyl acetate 95:5). After the removal of the solvent and trituration with hexanes the residue was dried under reduced pressure (50° C.) to give the product.

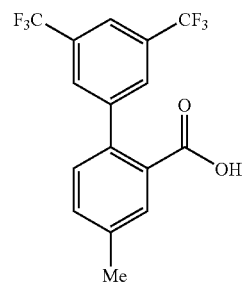

2-(3,5-Bis(trifluoromethyl)phenyl)-5-Methylbenzoic Acid (Entry 1, Table II)

Figure 24B:
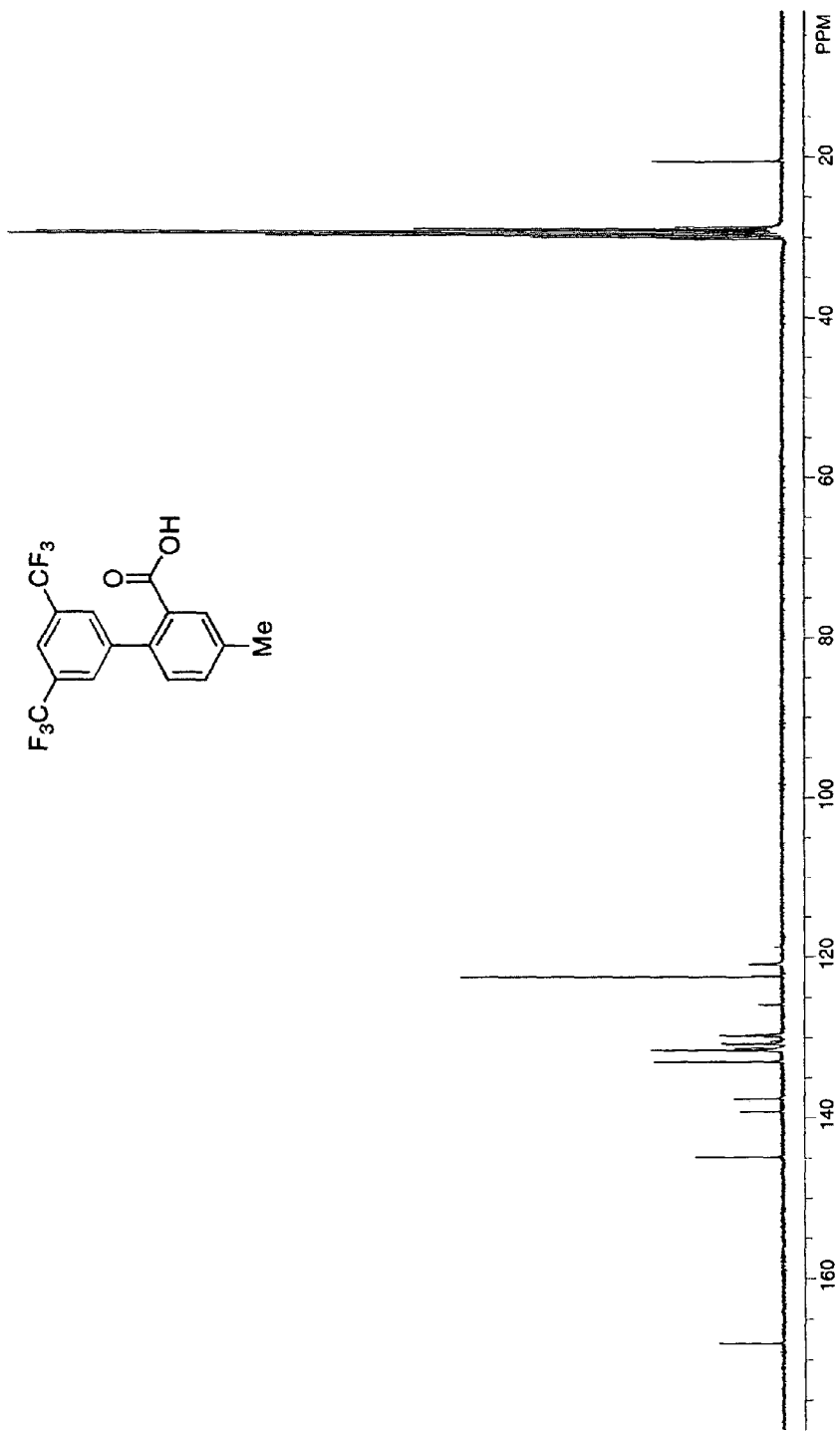
FIG. 24B depicts a $^{13}$C NMR spectrum of Entry 1 of Table II.

Palladium acetate (11.4 mg, 0.05 mmol), AgOAc (217 mg, 1.3 mmol), 3-methylbenzoic acid (136 mg, 1.0 mmol, 3,5-bis (trifluoromethyl)iodobenzene (1.02 g, 3.0 mmol and acetic acid (200 μL) were combined and heated at 120° C. for 4.5 h. After purification white solid was obtained, 207 mg (59%), mp 217-219° C. (isooctane). $R_f$-0.60 (1/9 ethyl acetate-dichloromethane). $^1$H NMR (300 MHz, acetone-$d_6$): δ 2.46 (s, 3H), 7.38-7.51 (m, 2H), 7.87 (s, 1H), 7.94 (s, 2H), 8.00 (s, 1H), 11.3 (brs, 1H). $^{13}$C NMR (75 MHz, acetone-$d_6$) 320.6, 120.9 (br s), 124.2 (q, J-271.1 Hz), 129.7 (br s), 130.8, 131.1 (q, J-33.3 Hz), 131.5, 131.7, 133.1, 137.6, 139.3, 144.9, 168.0. FT-IR (neat, $cm^1$) υ 1689, 1290, 1121. Anal. calcd for $C_{16}H_{10}F_6O_2$ (348.2 g/mol) C, 55.18; H, 2.89. Found: C) 55.07; H, 2.81. The $^1$H NMR and $^{13}$C NMR spectra are shown in FIGS. 24A&B, respectively.

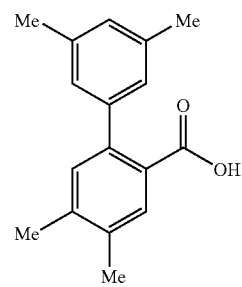

2-(3,5-Dimethylphenyl)-4,5-Dimethylbenzoic Add (Entry 2, Table II)

Figure 25A:
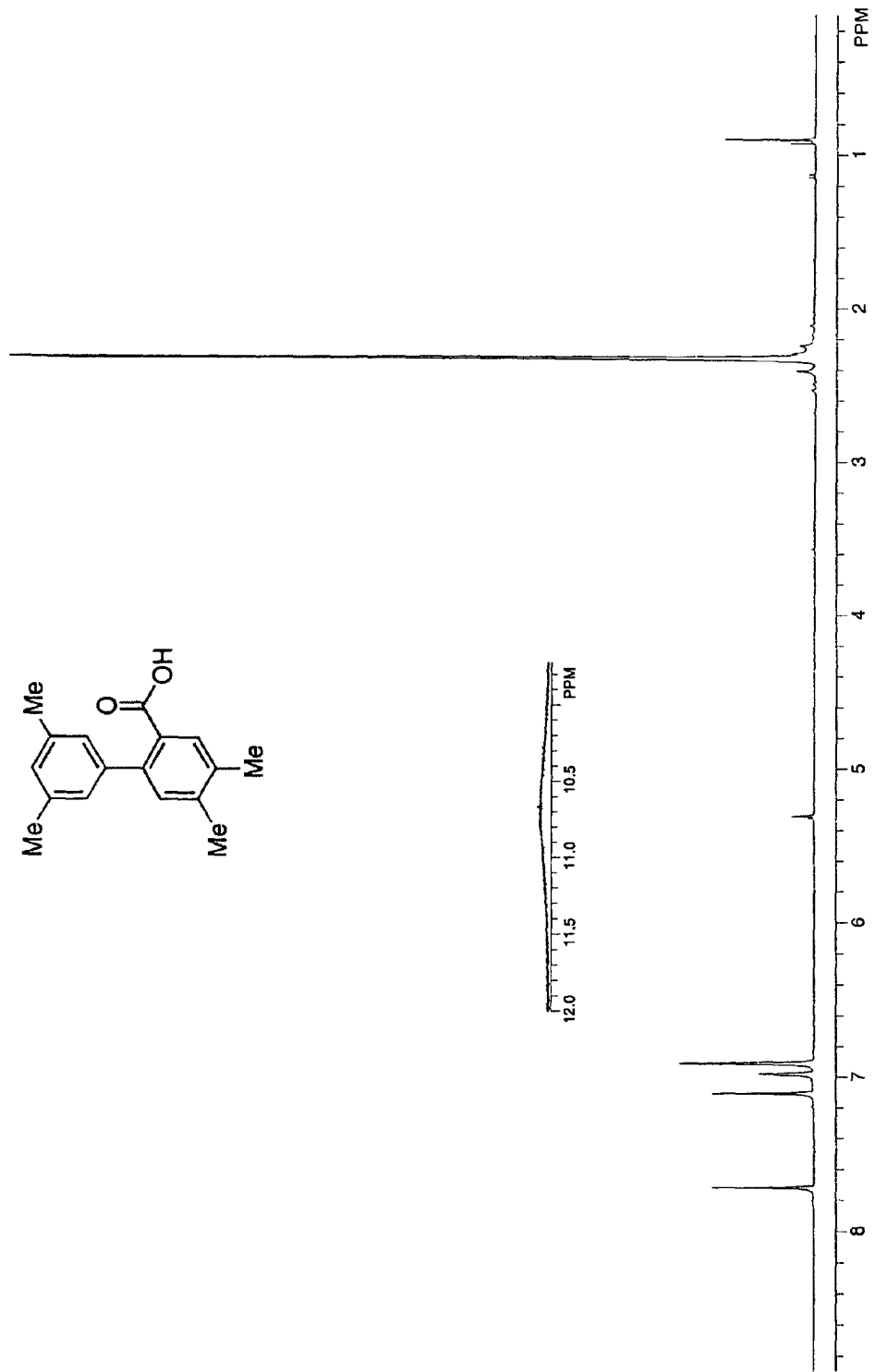
FIG. 25A depicts a $^1$H NMR spectrum of Entry 2 of Table II.
Figure 27A:
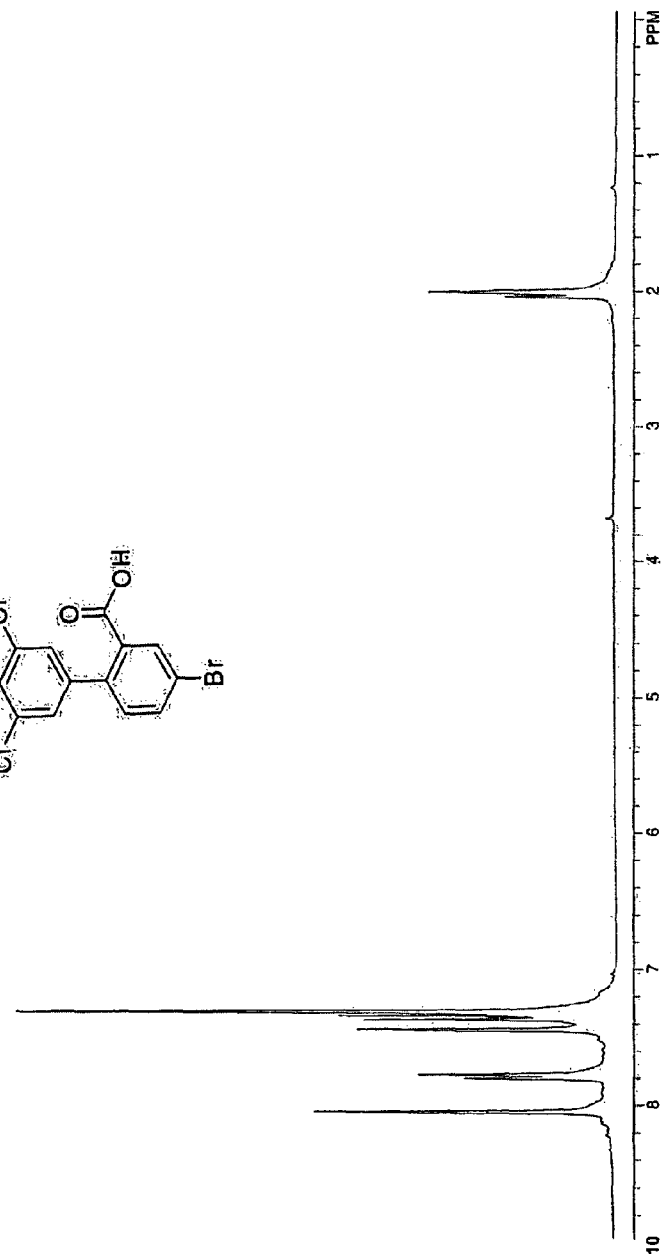
FIG. 27A depicts a $^1$H NMR spectrum of Entry 4 of Table II.

Palladium acetate (11.4 mg 0.05 mmol), AgOAc (217 mg, 1.3 mmol), 3,4-dimethylbenzoic acid (150 mg, 1.0 mmol), 3,5-dimethyliodobenzene (696 mg, 3.0 mmol) and acetic acid (200 mL) were combined and heated at 110° C. for 5 h. After purification light tan solid was obtained, 136 mg (53%), mp 189-192° C. (isooctane). $R_f$-0.60 (1/9 ethyl acetate-dichloromethane). $^1$H NMR (300 MHz, CD$_2$Cl$_2$): δ 2.34 (s, 12H), 6.93 (s, 2H), 7.01 (s, 1H), 7.12 (s, 1H), 7.73 (s, 1H), 10.7 (br s, 1H). $^{13}$C NMR (75 MHz, CDCl$_3$) δ 19.7, 20.3, 21.9, 126.9, 129.3, 132.4, 133.1, 136.0, 137.9, 141.6, 141.8, 141.9, 173.9. Signal for one aromatic carbon could not be located. FT-IR (neat, cm$^1$) υ 1695, 1667, 1287. Anal calcd for C$_{17}$H$_{18}$O$_2$ (254.32 g/mol): C, 80.28; H, 7.13. Found: C, 79.44; H, 7.12. The $^1$H NMR and $^{13}$C NMR spectra are shown in FIGS. 25A&B, respectively.

dichloroiodobenzene (819 mg, 3.0 mmol) and acetic acid (200 μL) were combined and heated at 120° C. for 5.5 h. After purification light tan solid was obtained, 183 mg (53%), mp 182-186° C. (isooctane). $R_f$-0.38 (1/9 ethyl acetate-dichloromethane). $^1$H NMR (300 MHz, acetone-d$_6$) δ 7.32 (br s, 2H), 7.36 (d, J-8.4 Hz, 1H), 7.44 (br s, 1H), 7.79 (d, J-8.4 Hz, 1H), 8.05 (br s, 1H). Carboxylate proton signal was not observed. $^{13}$C NMR (75 MHz, acetone-d$_6$) δ 122.2, 127.6, 127.7, 133.2, 133.3, 134.6, 135.0, 139.4, 144.5, 166.7. A signal for one aromatic carbon could not be located. FT-IR (neat, cm$^1$) υ 1699, 1299, 857. Anal. calcd for C$_{13}$H$_7$BrCl$_2$O$_2$ (346.00 g/mol): C, 45.13; H, 2.04. Found: C, 45.17; H, 2.04. The $^1$H NMR and $^{13}$C NMR spectra are shown in FIGS. 27A&B, respectively.

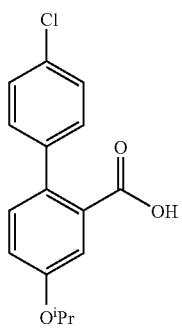

2-(4-Chlorophenyl)-4-Isopropoxybenzoic Add (Entry 3, Table II)

Figure 26A:
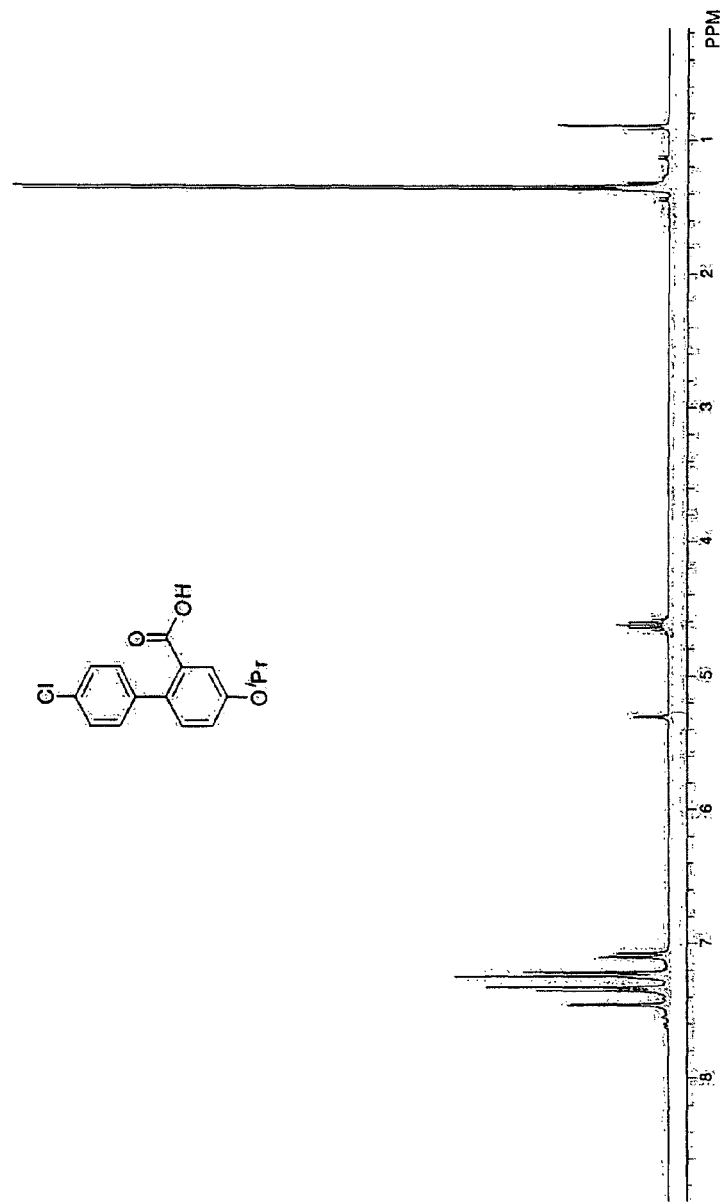
FIG. 26A depicts a $^1$H NMR spectrum of Entry 3 of Table II.

Palladium acetate (11.4 ng 0.05 mmol), AgOAc (217 mg, 1.3 mmol), 3-isopropoxybenzoic acid (180 mg, 1.0 mmol), 4-chloroiodobenzene (715.5 mg, 3.0 mmol) and acetic acid (200 μL) were combined and heated at 100° C. for 5.5 h. After purification light yellow solid was obtained, 200 mg (69%), mp 144-147° C. (isooctane). $R_f$-0.46 (1/9 ethyl acetate-dichloromethane). $^1$H NMR (300 MHz, CD$_2$Cl$_2$): δ 1.37 (d, J-6.0 Hz, 6H), 4.64 (sept, J-6.0 Hz, 1H), 7.09 (dd, J-8.0 Hz, 3.0 Hz, 1H), 7.22-7.26 (m, 3H), 7.32-7.36 (m, 2H), 7.46 (d, J-3.0 Hz, 1H), 10.2 (br s, 1H). $^{13}$C NMR (75 MHz, acetone-d$_6$) δ 21.3, 69.9, 116.7, 118.3, 127.8, 130.2, 131.9, 132.1, 132.3, 133.0, 140.1, 157.2, 168.2. FT-IR (neat, cm$^1$) υ 1690, 1278. Anal calcd for C$_{16}$H$_{15}$ClO$_3$ (290.74 g/mol): C, 66.10; H, 5.20. Found: C, 65.91; H, 5.11. The H NMR and $^{13}$C NMR spectra are shown in FIGS. 26A&B, respectively.

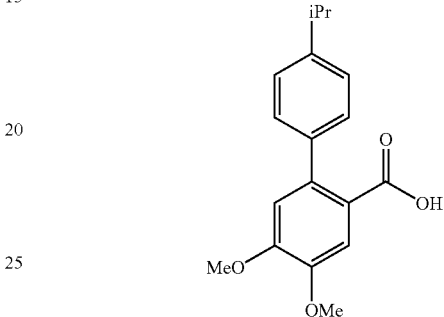

2-(4-Isopropylphenyl)-3,4-Dimethoxybenzoic Add (Entry 5, Table II)

Figure 28A:
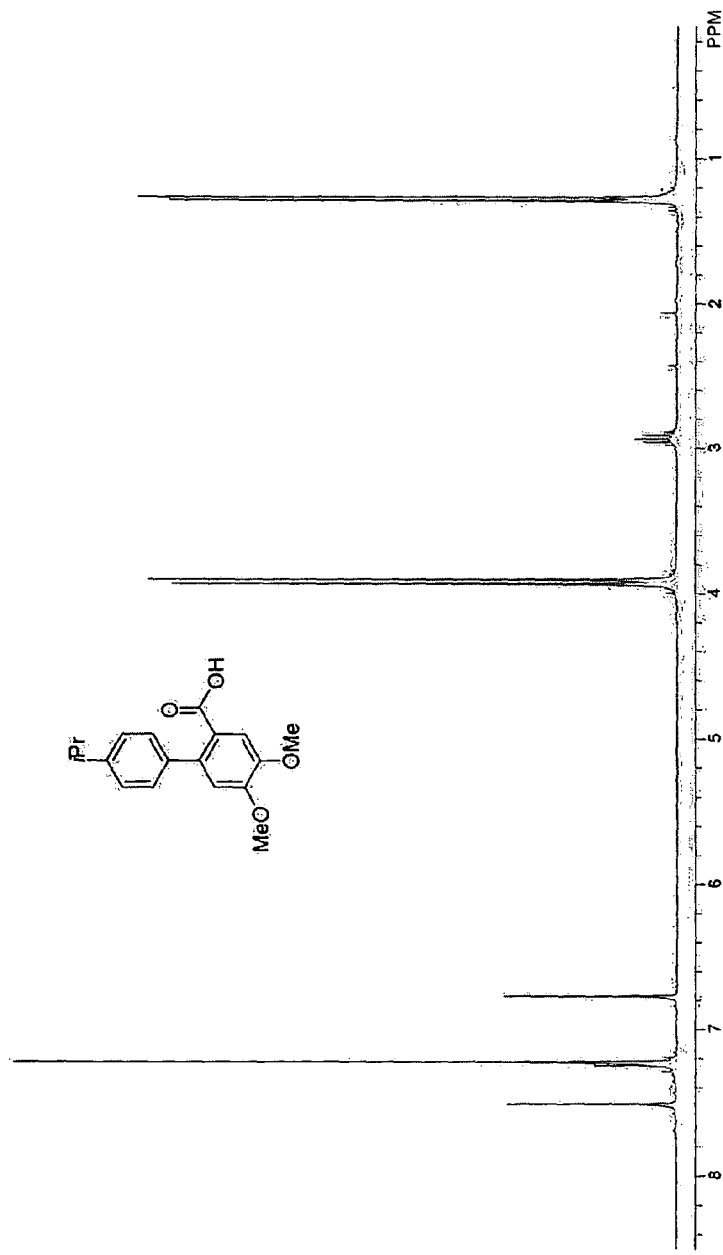
FIG. 28A depicts a $^1$H NMR spectrum of Entry 5 of Table II.
Figure 28B:
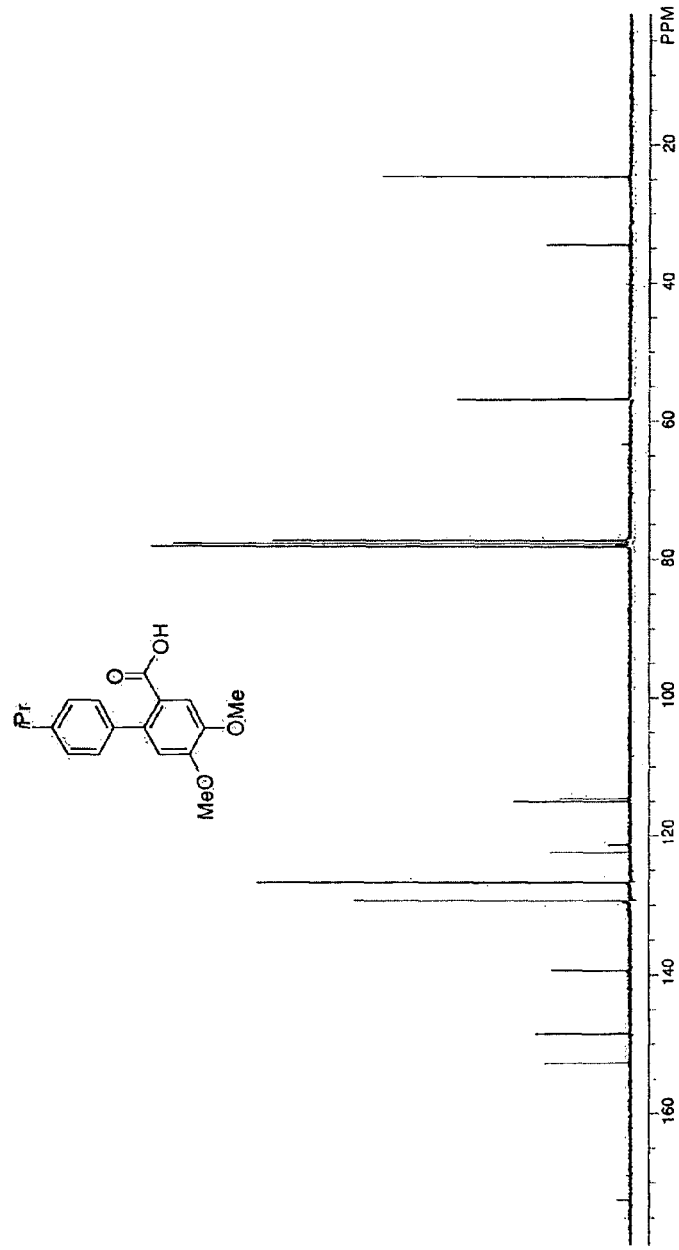
FIG. 28B depicts a $^{13}$C NMR spectrum of Entry 5 of Table II.

Palladium acetate (11.4 mg 0.05 mmol), AgOAc (217 mg, 1.3 mmol), 3,4-dimethoxybenzoic acid (182 mg, 1.0 mmol), 1-iodo-4-isopropylbenzene (738 mg, 3.0 mmol) and acetic acid (200 μL) were combined and heated at 130° C. for 7 h. After column chromatography and preparative HPLC 165 mg (55%) of a white solid was obtained, mp 125-127° C. (isooctane). $R_f$-0.52 (1:9 ethyl acetate-dichloromethane). $^1$H NMR (300 MHz, CDCl$_3$): δ 1.28 (d, J-6.6 Hz, 6H), 2.94 (septet, J-6.6 Hz, 1H), 3.90 (s, 3H), 3.93 (s, 3H), 6.77 (s, 1H), 7.23 (s, 4H), 7.51 (s, 1H). Carboxylate proton signal was not observed. $^{13}$C NMR (75 MHz, CDCl$_3$) δ 24.7, 34.6, 56.8, 56.9, 114.6, 115.1, 121.4, 126.8, 129.4, 139.3, 139.5, 148.5, 148.6, 152.7, 172.5. FT-IR (neat, cm$^1$) υ 1686, 1283, 1208. The $^1$H NMR and $^{13}$C NMR spectra are shown in FIGS. 28A&B, respectively.

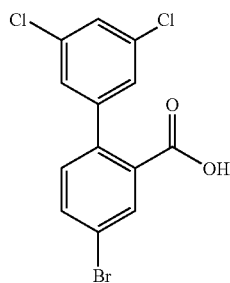

2-(3,5-Dichlorophenyl)-4-Bromobenzoic Acid (Entry 4, Table II)

Palladium acetate (11.4 mg 0.05 mmol), AgOAc (217 mg 1.3 mmol), 3-bromobenzoic acid (201 mg, 1.0 mmol), 3,5-

3-(3-Methyl)-2-Naphthoic Add (Entry 6, Table I)

Palladium acetate (11.4 mg, 0.05 mmol), AgOAc (217 mg, 1.3 mmol), 2-naphthoic acid (172 mg, 1.0 mmol), 3-iodotoluene (654 mg, 3.0 mmol) and acetic acid (200 μL) were combined and heated at 130° C. for 6 h. After column chromatography and preparative HPLC 176 mg (67%) of a light yellow solid was obtained, mp 182-184° C. (acetone). $R_f$-0.64

Figure 29A:
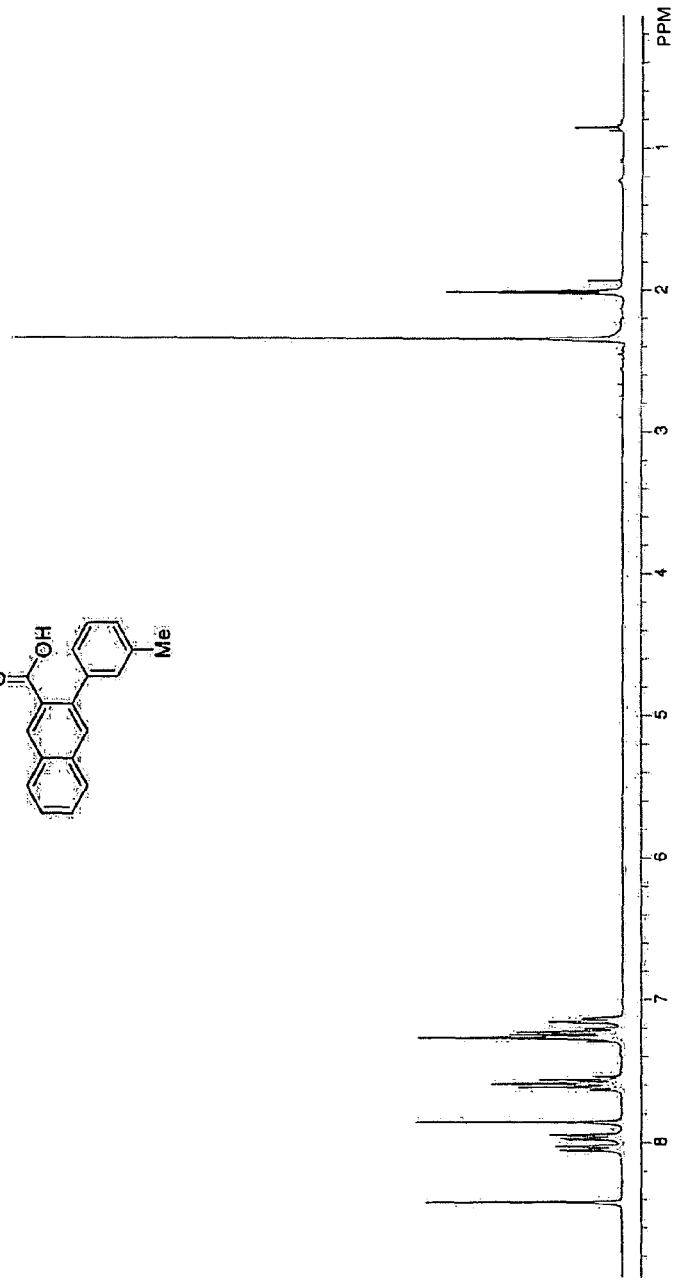
FIG. 29A depicts a $^1$H NMR spectrum of Entry 6 of Table II.
Figure 29B:
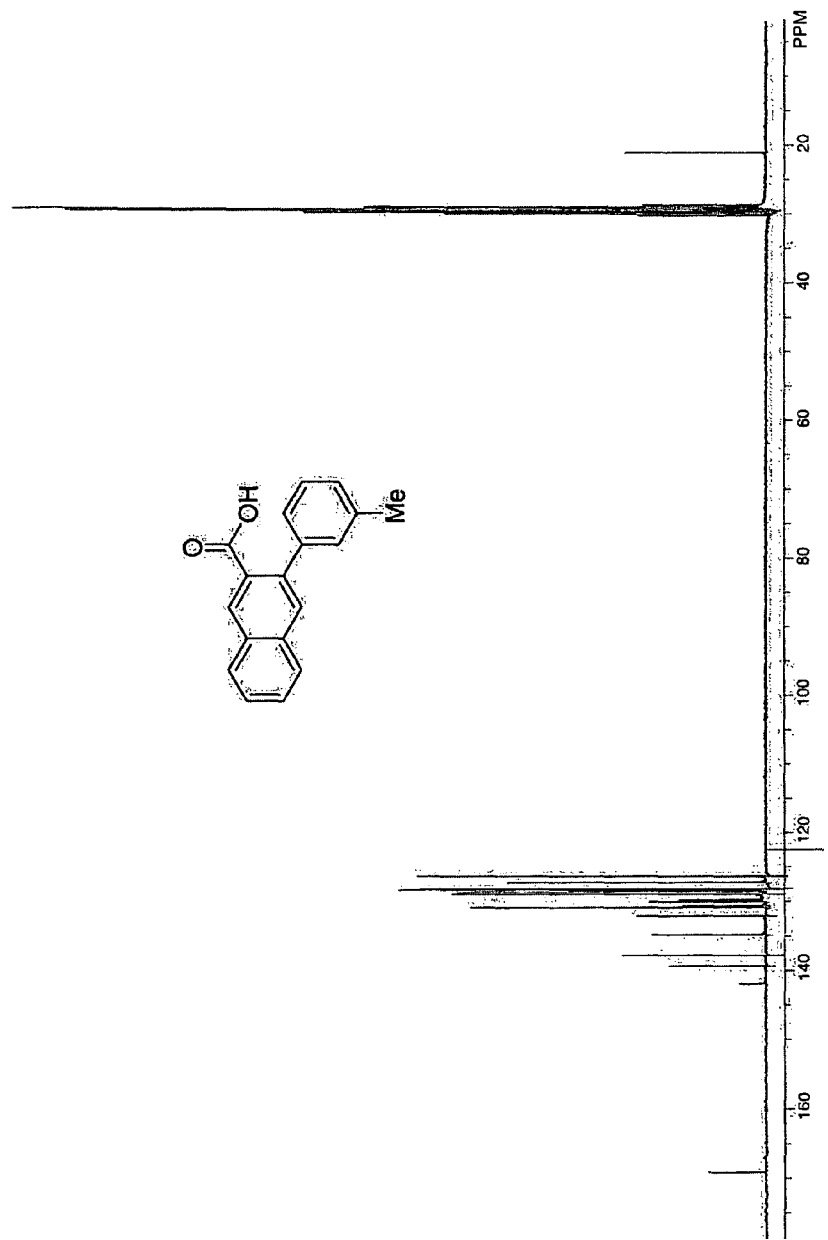
FIG. 29B depicts a $^{13}$C NMR spectrum of Entry 6 of Table II.

(1:9 ethyl acetate-dichloromethane). $^1$H NMR (300 MHz, acetone-d$_6$) δ 2.37 (s, 3H), 7.13-7.18 (m, 1H), 7.19-7.30 (m, 3H), 7.54-7.64 (m, 2H), 7.86 (s, 1H), 7.95-7.98 (m, 1H), 8.02-8.06 (m, 1H), 8.42 (s, 1H). Carboxylate proton signal was not observed. $^{13}$C NMR (75 MHz, acetone-d$_6$) δ 21.3, 126.5, 127.4, 128.3, 128.4, 128.5, 128.8, 129.1, 129.9, 130.2, 130.8, 131.0, 132.3, 135.0, 138.0, 139.5, 142.2, 169.0. FT-IR (neat, cm$^1$) υ 1675, 1297. The $^1$H NMR and $^{13}$C NMR spectra are shown in FIGS. 29A&B, respectively.

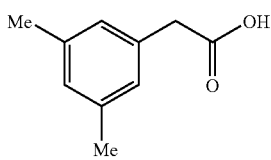

3,5-Dimethylphenyl Acetic Acid (Entry 7, Table II)

Figure 30:
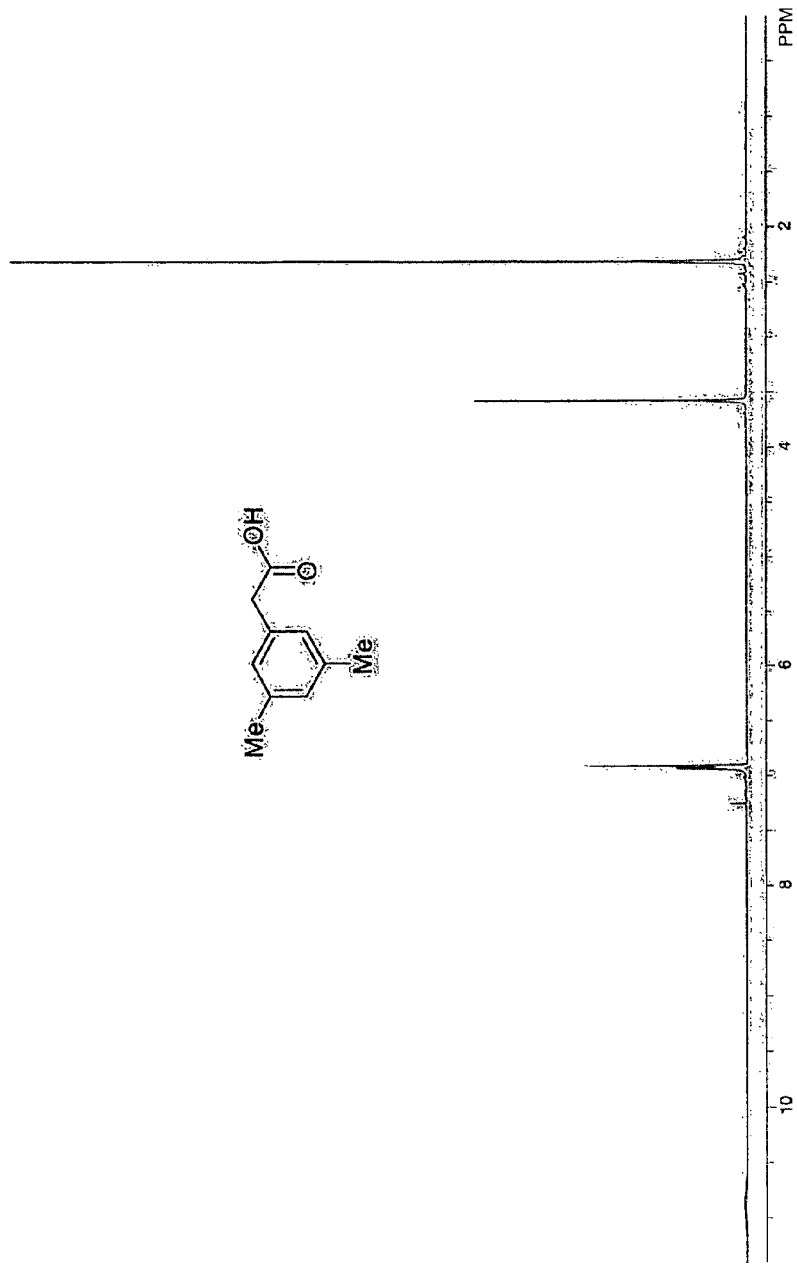
FIG. 30 depicts a $^1$H NMR spectrum of Entry 7 of Table II.

Palladium acetate (11.4 mg, 0.05 mmol), AgOAc (217 mg, 1.3 mmol), 5-iodo-m-xylene (696, 3.0 mmol) and acetic acid (200 μL) were combined and heated at 130° C. for 7 h. After column chromatography and preparative HPLC 112 mg (52% based on AgOAc) of a white solid was obtained, $^1$H NMR (300 MHz, CHCl$_3$): δ 2.31 (s, 6H), 3.57 (s, 2H), 6.91 (s, 2H), 6.93 (s, 1H), 10.87 (br s, 1H). This compound is known.[2] The $^1$H NMR spectrum is shown in FIG. 30.

General Procedure for Coupling of Chloroarenes with Benzoic Acids

Outside the glovebox a 2-dram vial equipped with a magnetic stir bar was charged with Pd(OAc)$_2$ (5 mol %), ArCO$_2$H (0.5 mmol) and chloroarene (3-5 equiv). The vial was flushed with argon, capped and placed inside a glovebox. To this mixture was added butyldi-1-adamantylphosphine (10 ml %), Cs$_2$CO$_3$ (2.2 equiv), molecular sieves 3 Å (155 mg) and anhydrous DMF (2.5 mL). The sealed vial was taken out of the glovebox, stirred at room temperature for 2 h and placed in a preheated oil bath (145° C.) for 24 h. The reaction mixture was allowed to cool to room temperature and quenched with 15% aqueous HCl (4 mL). Resulting suspension was extracted with ethyl acetate (3×3 mL) and the organic layer filtered through a pad of Celite®. The filtrate was concentrated under vacuum to a volume of about 2 mL. The mixture was adsorbed on silica gel and subjected to flash chromatography (hexanes then dichloromethane-ethyl acetate 95:5). The DCM-EtOAc fraction was concentrated, the residue triturated with distilled water (3×2 mL) and dried under reduced pressure. The residue, after trituration with hexanes (2×2 mL) and/or purification by preparative HPLC and drying under reduced pressure (50° C.) yielded the product.

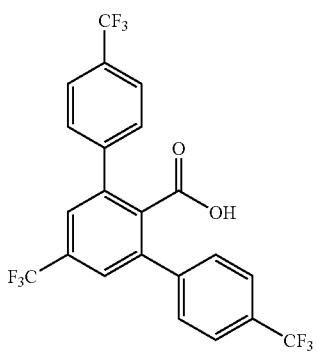

2,6-Bis(4-Trifluomethylphenyl)-4-Trifluoromethyl-benzoic Acid (Entry 1, Table III)

Figure 31A:
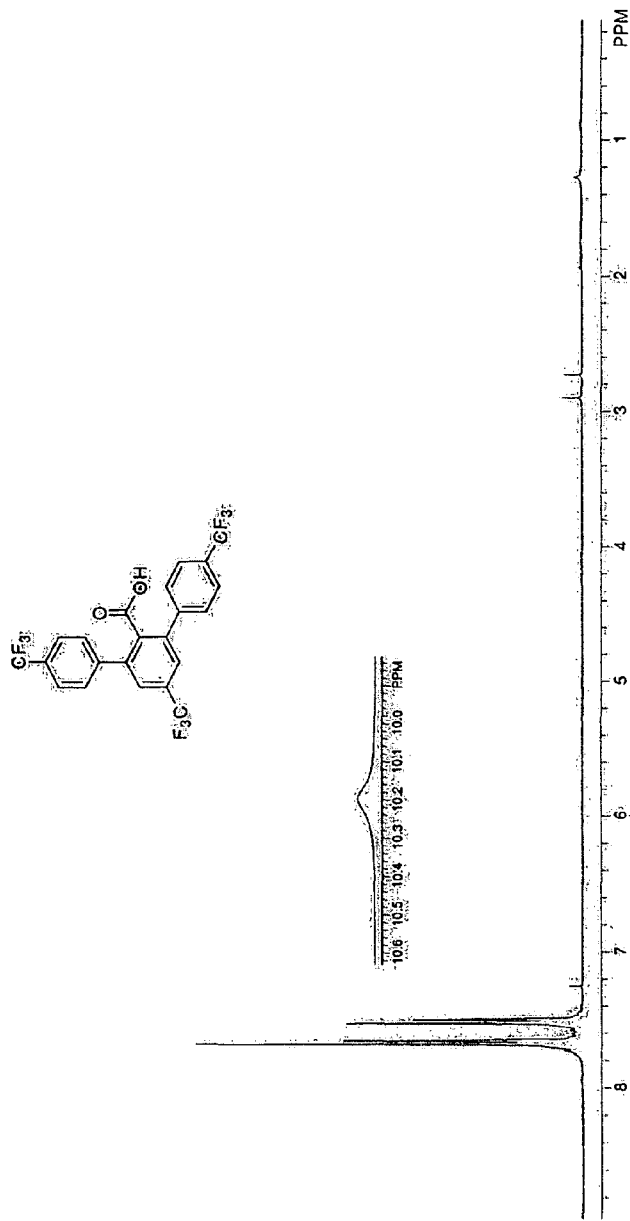
FIG. 31A depicts a $^1$H NMR spectrum of Entry 1 of Table III.
Figure 31B:
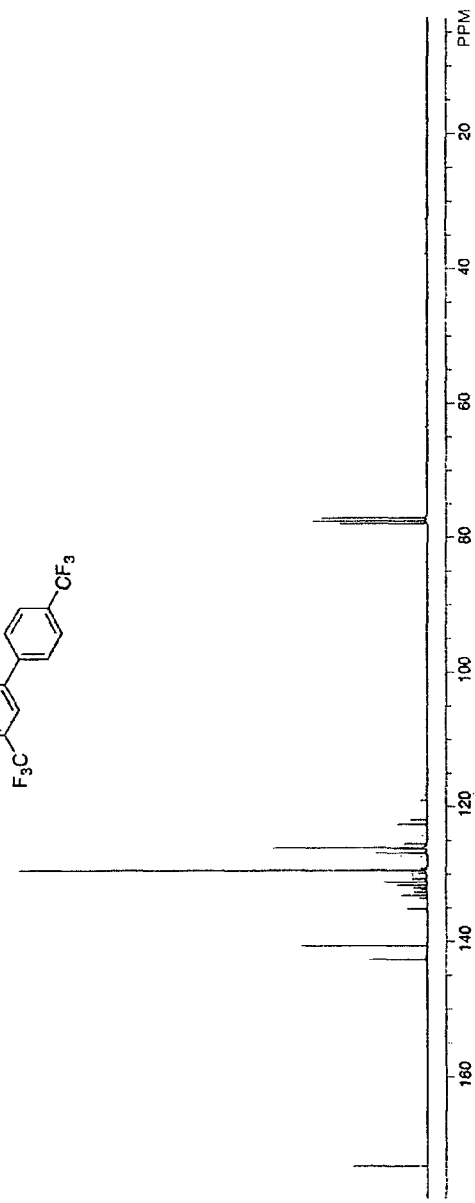
FIG. 31B depicts a $^{13}$C NMR spectrum of Entry 1 of Table III

Palladium acetate (5.6 mg, 0.025 mmol), 4-(trifluoromethyl)benzoic acid (95 mg, 0.5 mmol), 4-chlorobenzotrifluoride (271.5 mg, 1.5 mmol), butyldi-1-adamantylphosphine (19.2 mg, 0.05 mmol), Cs$_2$CO$_3$ (358 mg, 1.1 mmol), molecular sieves 3 Å (155 mg) and anhydrous DMF (2.5 mL). After column chromatography 180 mg (75%) of a white solid was obtained, mp 135-136° C. (isooctane). R$_f$-0.66 (1/9 ethyl acetate-dichloromethane). $^1$H NMR (300 MHz, CDCl$_3$) δ 7.50-7.53 (m, 4H), 7.65-7.68 (m, 6H), 10.2 (br s, 1H). $^{13}$C NMR (75 MHz, CDCl$_3$) δ 123.7 (q, J-273.0 Hz), 124.5 (q, J-271.7 Hz), 126.0 (q, J-3.5 Hz), 126.8 (q, J-3.7 Hz), 129.4, 131.4 (q, J-33.3 Hz), 132.9 (q, J-34.0 Hz), 135.1, 140.6, 142.6, 173.1. FT-IR (neat cm$^1$) υ 1171, 1324, 1133. Anal. calcd for C$_{22}$H$_{11}$F$_9$O$_2$ (478.31 g/mol): C, 55.24; H, 2.32. Found; C, 55.21; H, 2.43. The $^1$H NMR and $^{13}$C NMR spectra are shown in FIGS. 31A&B, respectively.

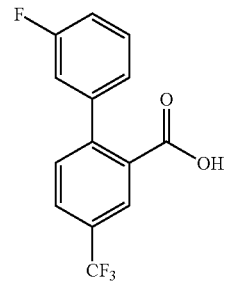

2-(3-Fluorophenyl)-5-(Trifluoromethyl)Benzoic Acid Entry 2, Table III)

Figure 32A:
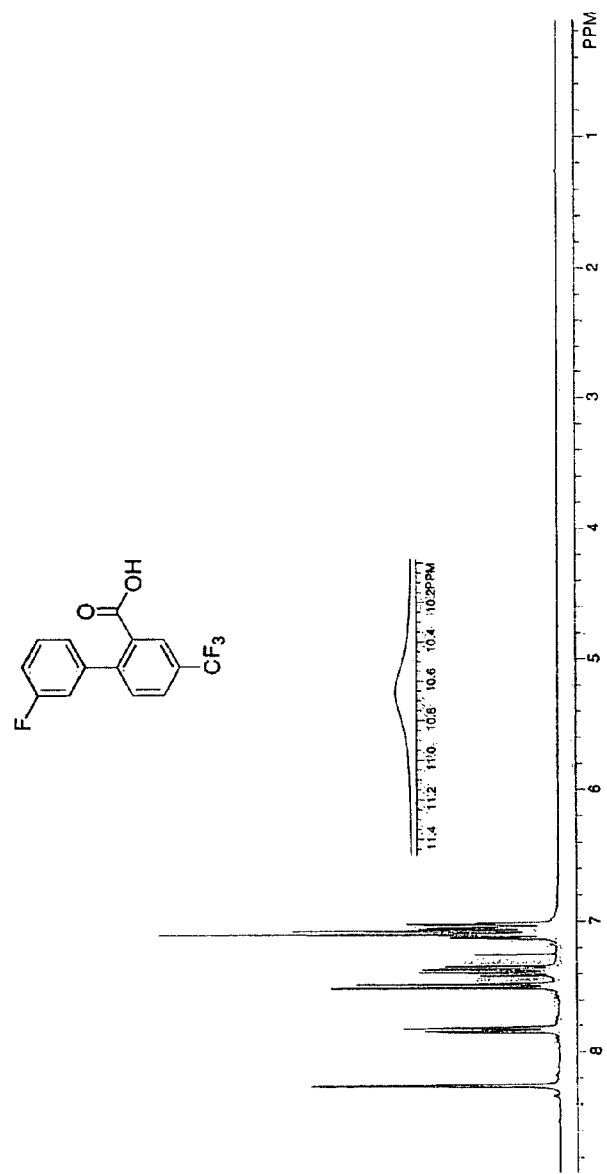
FIG. 32A depicts a $^1$H NMR spectrum of Entry 2 of Table III.
Figure 32B:
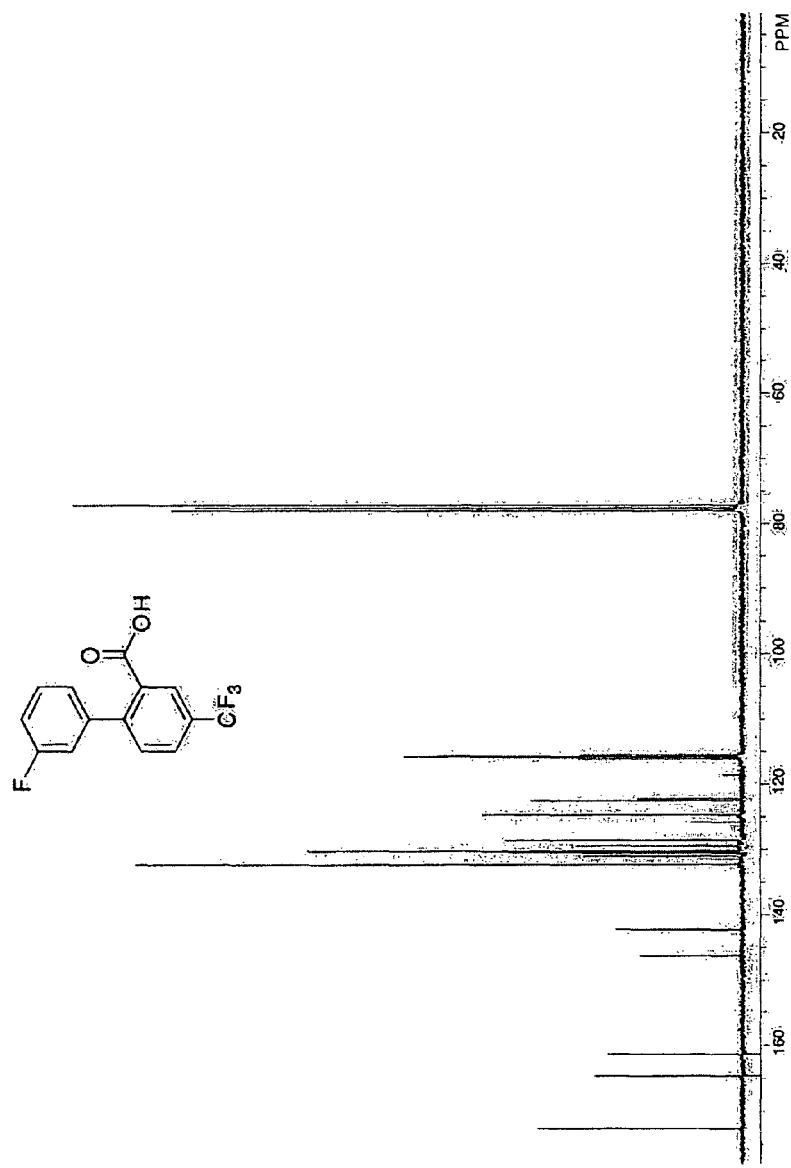
FIG. 32B depicts a $^{13}$C NMR spectrum of Entry 2 of Table III

Palladium acetate (5.6 mg, 0.025 mmol), 3-(trifluoromethyl)benzoic acid (95 mg, 0.5 mmol), 1-chloro-3-fluorobenzene (131 mg, 1.0 mmol), butyldi-1-adamantylphosphine (19.2 mg, 0.05 mmol), CS$_2$CO$_3$ (358 mg, 1.1 mmol), molecular sieves 3 Å (155 mg) and anhydrous DMF (2.5 mL). After column chromatography and preparative HPLC 102 mg (72%) of a white solid was obtained, mp 107-110° C. (isooctane). R$_f$-0.36 (1/9 ethyl acetate-dichlororrmethane). $^1$H NMR (300 MHz, CDCl$_3$) δ7.01-7.13 (m, 3H), 7.25-7.41 (m, 1H), 7.46-1.50 (m, 1H), 7.80-7.85 (m, 1H), 8.25 (s, 1H), 10.7 (br s, 1H). $^{13}$C NMR (75 MHz, CDCl$_3$; C—F coupling constants assigned where possible; list of signals where assignment not possible) δ 115.4, 115.7, 115.8, 116.1, 124.6, 124.7, 128.5 (q, J-3.6 Hz), 129.4 (q, J-3.6 Hz), 130.2, 130.3, 130.4, 130.8 (q, J-33.5 Hz), 132.3, 142.3, 142.2, 145.2, 163.0 (d, J-246.6 Hz), 172.6. FT-IR (neat, cm$^1$) υ 1689, 1287, 1130. Anal. calcd for C$_{14}$H$_8$F$_4$O$_2$ (284.21 g/mol): C, 59.16, H, 2.84. Found: C, 59.33; H, 2.79. The $^1$H NMR and $^{13}$C NMR spectra are shown in FIGS. 32A&B, respectively.

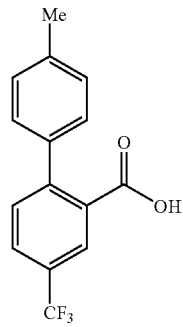

2-(4-Methylphenyl)-5-(trifluoromethyl)benzoic Acid (Entry 3, Table III)

Figure 33A:
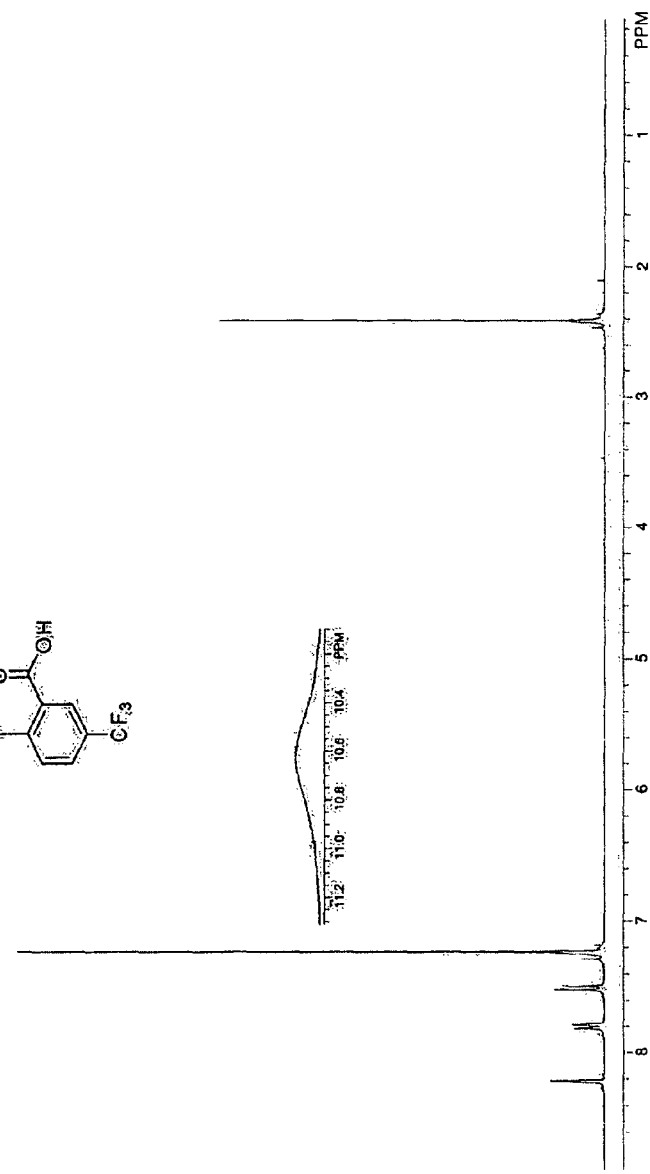
FIG. 33A depicts a $^1$H NMR spectrum of Entry 3 of Table III.
Figure 33B:
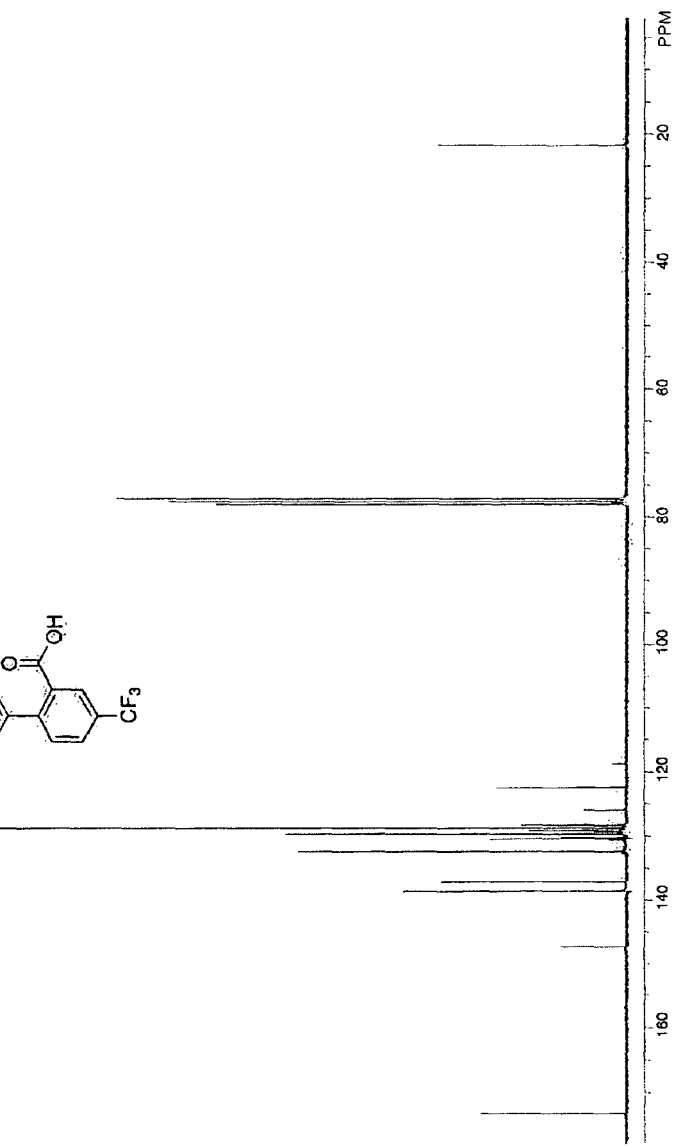
FIG. 33B depicts a $^{13}$C NMR spectrum of Entry 3 of Table III

Palladium acetate (5.6 mg 0.025 mmol) (5.6 mg 0.025 mmol), 3-(trifluoromethyl)benzoic acid (95 mg, 0.5 mmol), 4-chlorotoluene (127 mg, 1.0 mmol), butyldi-1-adamantylphosphine (19.2 mg, 0.05 mmol), $Cs_2CO_3$ (358 mg, 1.1 mmol), molecular sieves 3 Å (155 mg) and anhydrous DMF (2.5 mL). After column chromatography and preparative HPLC 116 mg (83%) of a white solid was obtained, mp 128-129° C. (isooctane). $R_f$-0.54 (19 ethyl acetate-dichloromethane). $^1$H NMR (300 MHz, $CDCl_3$) δ2.40 (s, 3H), 7.22 (s, 4H), 7.48-7.51 (m, 1H), 7.76-7.81 (m, 1H), 8.20 (br s, 1H), 10.6 (br s, 1H). $^{13}$C NMR (75 MHz, $CDCl_3$) δ21.8, 124.2 (q, J-271.9 Hz), 128.3 (9, J-2.9 Hz), 128.8, 129.2 (q, J-3.4 Hz), 129.6, 130.0 (q, J-33.5 Hz), 130.4, 132.4, 137.2, 138.6, 147.4, 173.3. FT-IR (neat, $cm^1$) υ 1699, 1281, 1124. Anal. calcd for $C_{15}H_{11}F_3O_2$ (280.24 g/mol): C, 64.29H, 3.96. Found: C, 64.57; H, 3.90. The $^1$H NMR and $^1$C NMR spectra are shown in FIGS. 33A&B, respectively.

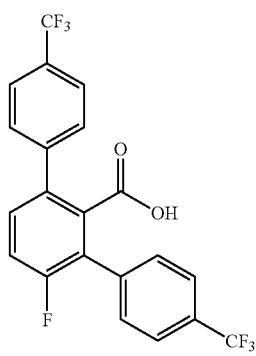

2,6-Bis(4-trifluomethylphenyl)-3-fluorobenzoic Acid (Entry 4, Table III)

Figure 34B:
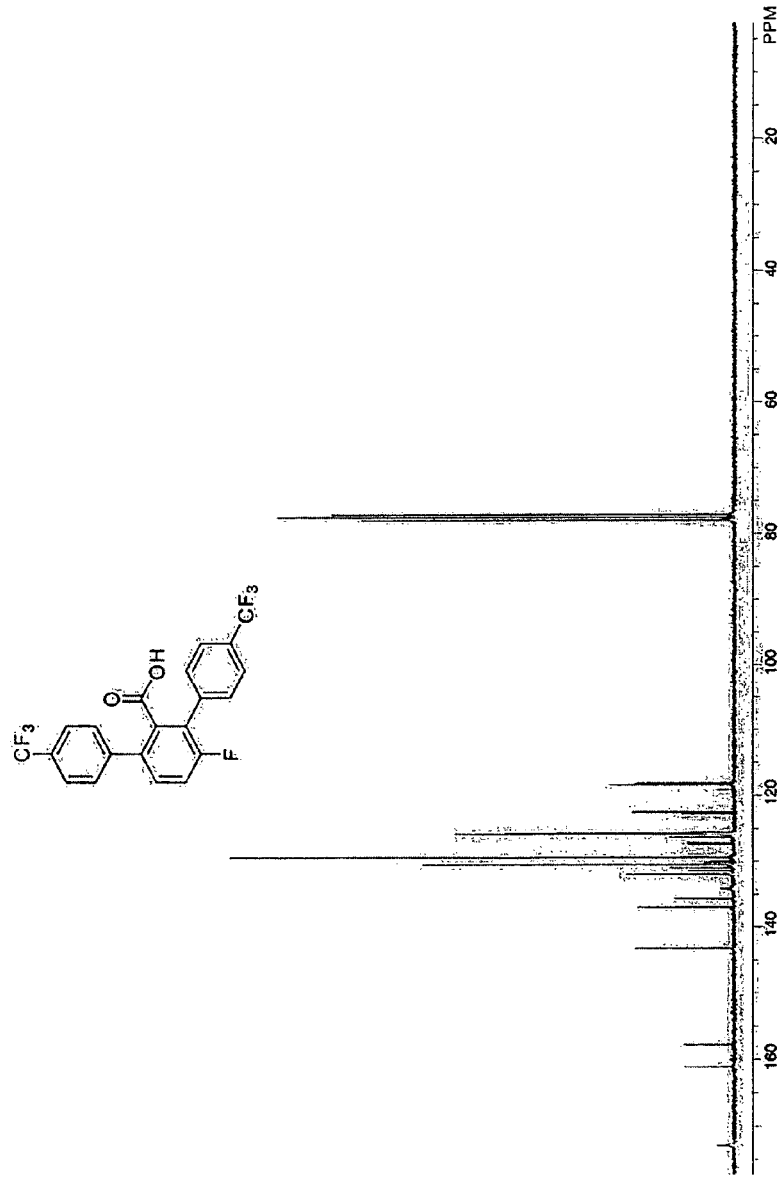
FIG. 34B depicts a $^{13}$C NMR spectrum of Entry 4 of Table III

Palladium acetate (5.6 mg, 0.025 mmol), 3-fluorobenzoic acid (70 mg, 0.5 mmol), 4-chlorobenzotrifluoride (271.5 mg, 1.5 mmol), butyldi-1-adamantylphosphine (19.2 mg, 0.05 mmol), $Cs_2CO_3$ (358 mg, 1.1 mmol), molecular sieves 3 Å (155 mg) and anhydrous DMF (2.5 mL). After column chromatography 195 mg (91%) of a white solid was obtained, mp 163-164° C. (isooctane). $R_f$-0.70 (1/9 ethyl acetate-dichloromethane). $^1$H NMR (300 MHz, $CDCl_3$) δ 7.30-7.41 (m, 2H), 7.43-7.47 (m, 4H), 7.61-7.66 (m, 4H), 9.9 (br s, 1H). $^{13}$C NMR (75 MHz, $CDCl_3$; C—F coupling constants assigned where possible; list of signals where assignment not possible) δ 118.4, 118.0, 124.5 (q, J-272.0), 124.6 (q, J-273.0 Hz), 125.7 (q, J-3.7 Hz), 125.9 (q, J-3.7 Hz), 127.4, 127.2, 129.4, 130.5, 130.8 (q, J-31.1 Hz), 131.2 (q, J-33.3 Hz), 132.0, 131.9, 134.1 (br s), 135.7, 135.6, 137.0, 143.2, 159.4 (d, J-250.4 Hz), 172.8. FT-IR (neat $cm^1$) υ 1704, 1324, 1127. Anal. calcd for $C_{21}H_{11}F_7O_2$ (428.30 g/mol): C, 58.89; H, 2.59. Found: C, 58.79; H, 2.56. The H NMR and $^{13}$C NMR spectra are shown in FIGS. 34A&B, respectively.

A sample of the acid (10 mg) was suspended in triethylamine (1 mL). The mixture was heated until it became homogeneous. After cooling to room temperature colorless crystals suitable for X-ray structure determination were formed.

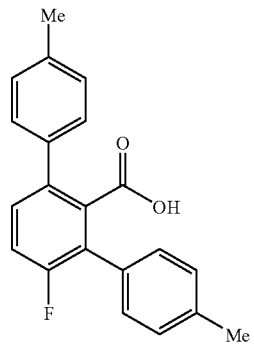

3-Fluoro-2,6-bis(4-methylphenyl)benzoic Acid (Entry 5, Table III)

Palladium acetate (5.6 mg, 0.025 mmol), 3-fluorobenzoic acid (95 mg, 0.5 mmol), 4-chlorotoluene (254 mg, 2 mmol), butyldi-1-adamantylphosphine (19.2 mg, 0.05 mmol), $Cs_2CO_3$ (358 mg, 1.1 mmol), molecular sieves 3 Å (155 mg) and anhydrous DMF (2.5 mL). After flash chromatography and preparative HPLC 109 mg (68%) of a white solid was obtained, mp 167-168° C. (isooctane). $R_f$-0.76 (1/9 ethyl acetate-dichloromethane). $^1$H NMR (300 MHz, $CDCl_3$) δ 2.40 (br s, 6H), 7.15-7.34 (m, 10H). Carboxylate proton signal was not observed. $^{13}$C NMR (75 MHz, $CDCl_3$, C—F coupling constants assigned where possible; list of signals where assignment not possible) δ 21.7, 21.8, 117.3, 117.6, 128.1, 128.4, 128.9, 129.4, 129.6, 130.0, 130.6, 131.0, 131.1, 134.4, 134.5, 136.6, 136.7, 137.2, 138.0, 138.5, 159.3 (d, J-246.1 Hz), 172.7. FT-IR (neat, $cm^1$) υ 1701, 1469, 1287. Anal. calcd for $C_{21}H_{12}FO_2$ (320.36 g/mol): C, 78.73; H, 5.35. Found: C, 78.38; H, 5.44. The $^1$H NMR and $^{13}$C NMR spectra are shown in FIGS. 35A&B, respectively.

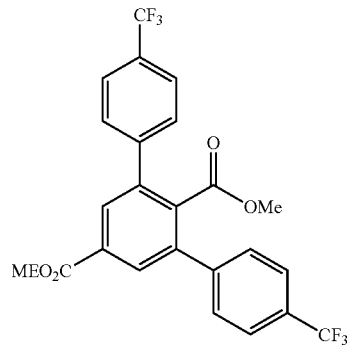

Dimethyl 2,6-bis(4-trifluomethylphenyl)-1,4-benzenedicarboxylate (Entry 6, Table III)

Figure 36A:
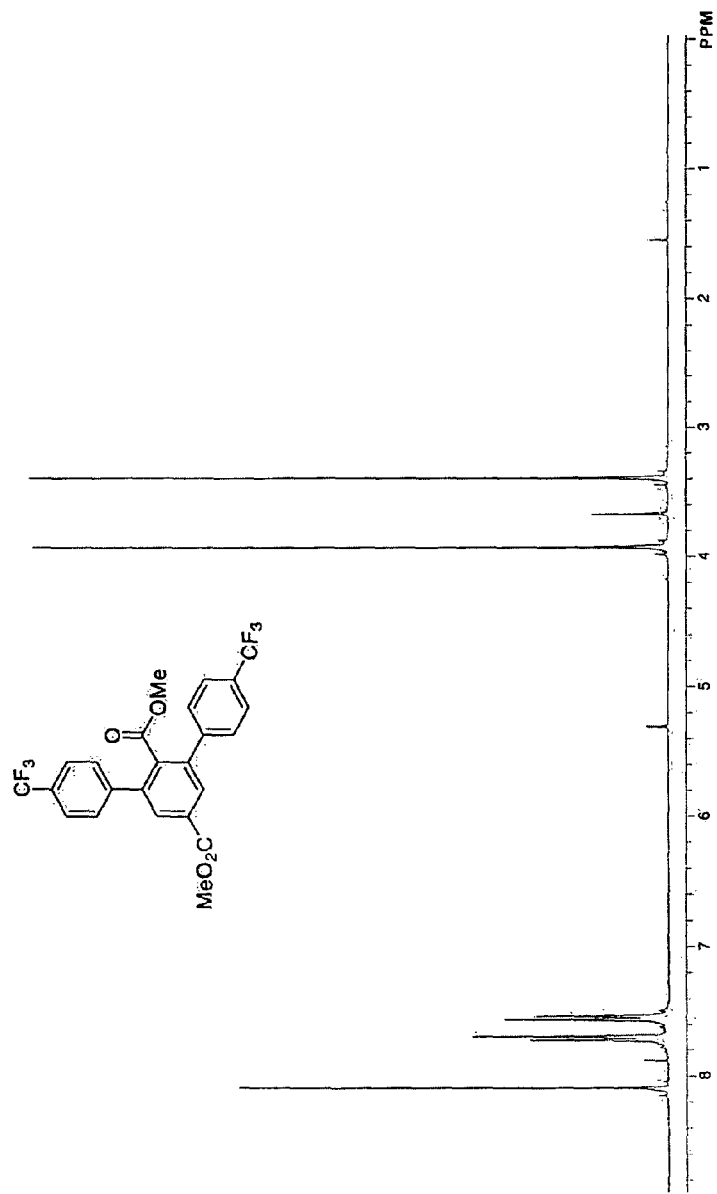
FIG. 36A depicts a $^1$H NMR spectrum of Entry 6 of Table III.
Figure 36B:
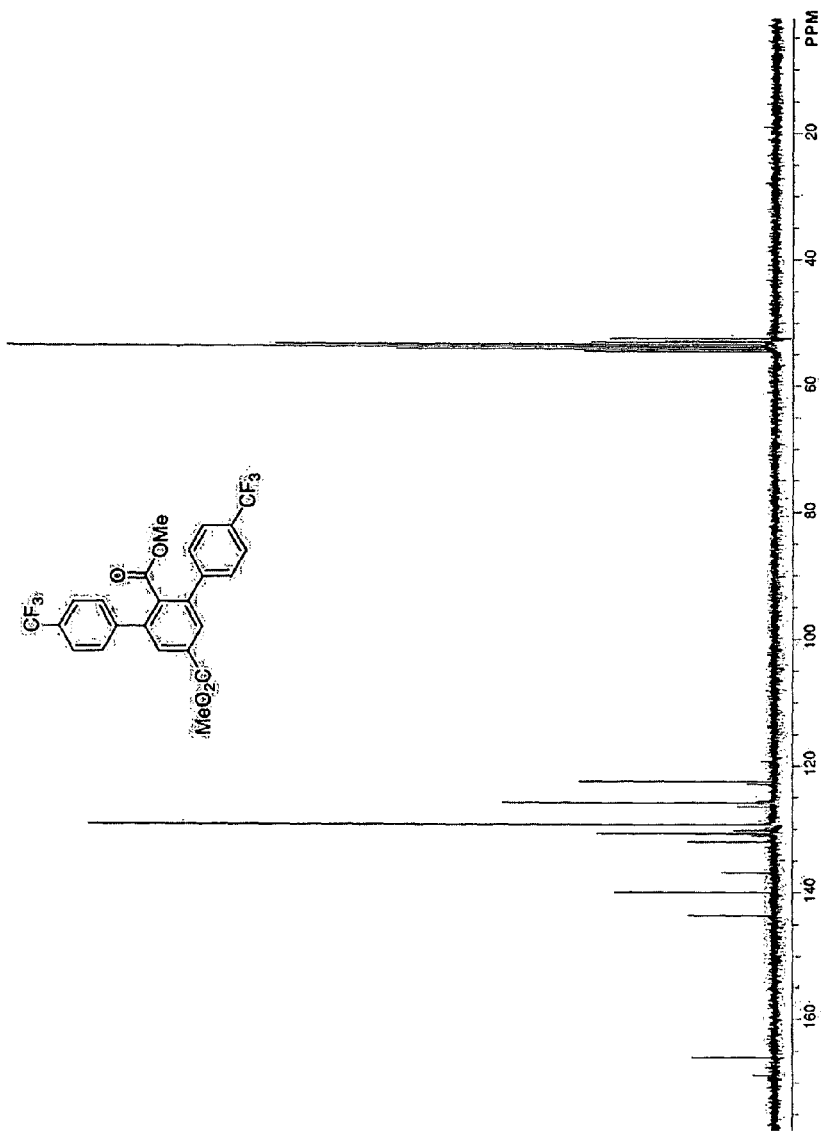
FIG. 36B depicts a $^{13}$C NMR spectrum of Entry 6 of Table III

Palladium acetate (5.6 mg, 0.025 mmol), monomethyl terephthalate (90 mg, 0.5 mmol), 4-chlorobenzo-trifluoride (271.5 mg, 1.5 mmol), butyldi-1-adamantylphosphine (19.2 mg, 0.05 mmol), $Cs_2CO_3$ (358 mg, 1.1 mmol), molecular sieves 3 Å (155 mg) and anhydrous DMF (2.5 mL). After the reaction and workup the residue was dissolved in methanol (10 nL) and cooled to 0° C. (Trimethylsilyl)diazomethane in hexanes (5.0 mL of a 2.0M solution, 1 mmol) was added dropwise, the cooling bath was removed and the mixture stirred for 5 h. The solvent was removed under reduced pressure. Purification by flash chromatography (hexanes then dichloromethane-ethylacetate 95:5) afforded 190 mg (79%) of a white solid, mp 158-160° C. (isooctane). $R_f$-0.36 (1/9 ethyl acetate-hexanes). $^1$H NMR (300 MHz, CD$_2$Cl$_2$) δ3.41 (s, 3H), 3.94 (s, 3H), 7.55-7.57 (m, 4H), 7.71-7.74 (m, 4H), 8.11 (s, 2H). $^{13}$C NMR (75 MHz, CD$_2$Cl$_2$) δ52.7, 53.1, 124.7 (q, J-272.95 Hz), 125.9 (q, J-3.9 Hz), 129.4, 130.5 (q, J-32.1 Hz), 130.8, 132.1, 136.9, 140.0, 143.6, 166.1, 168.9. FT-IR (neat, cm$^1$) υ 1731, 1326, 1120. Anal. calcd for C$_{24}$H$_{16}$F$_6$O$_4$, (482.37 g/mol): C, 59.76; H, 3.34. Found: C, 59.62; H, 3.29. The $^1$H NMR and $^{13}$C NMR spectra are shown in FIGS. 36A&B, respectively.

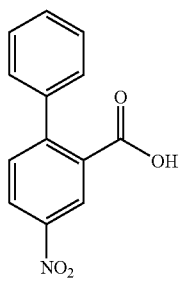

2-Phenyl-3-nitrobenzoic Acid (Entry 7, Table III)

Palladium acetate (5.6 mg, 0.025 mmol), 3-nitrobenzoic acid (84 mg, 0.5 mmol) and 4-chlorobenzene (283 mg, 2.5 mmol), butyldi-1-adamantylphosphine (19.2 mg, 0.05 mmol, Cs$_2$CO$_3$ (358 mg, 1.1 mmol), molecular sieves 3 Å (155 mg) and anhydrous DMF (2.5 mL). After flash chromatography and preparative HPLC 79 mg (65%) of a white solid was obtained. Analytical data are consistent with that of previously reported data.$^3$ $^1$H NMR (300 MHz, CDCl$_3$) δ 7.32-7.37 (m, 2H), 7.42-7.46 (m, 3H), 7.57 (d, J-8.4 Hz, 1H), 8.40 (dd, J-8.4 Hz, 2.1 Hz, 1H), 8.80 (d, J-2.1 Hz, 1H). Carboxylate proton signal was not observed. The $^1$H NMR spectrum is shown in FIG. 37.

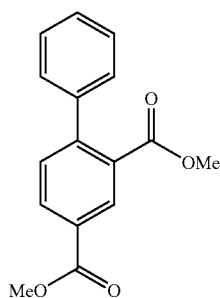

Dimethyl 4-phenylisophthalate (Entry 8, Table III)

Figure 38:
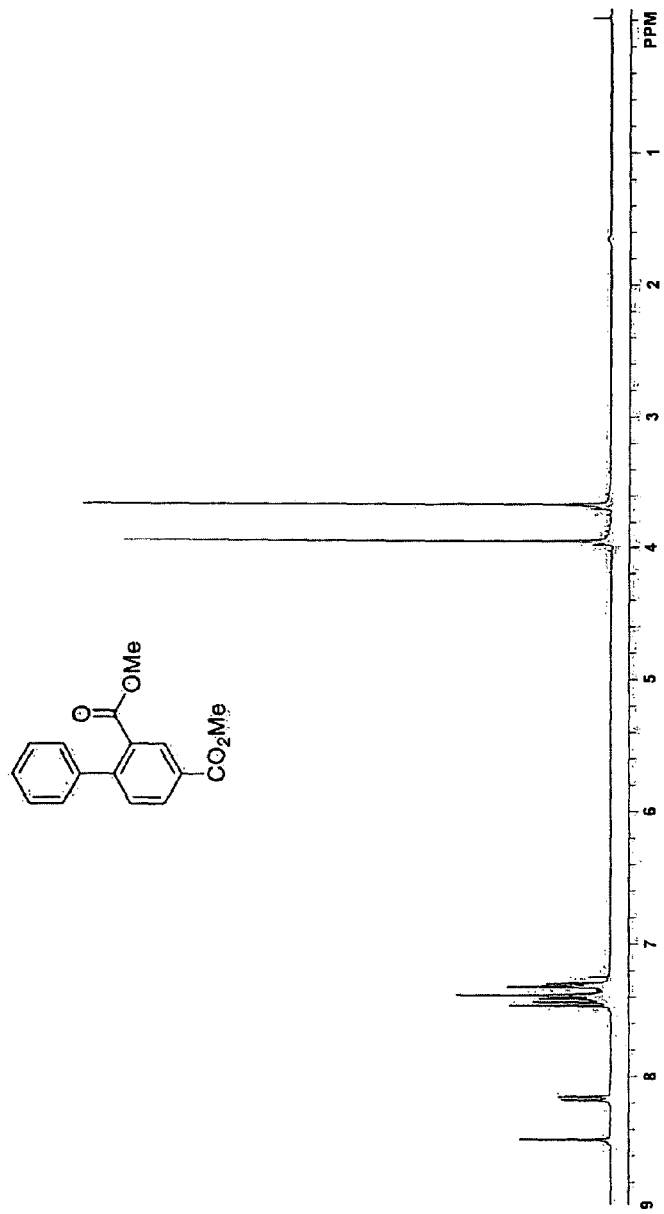
FIG. 38 depicts a $^1$H NMR spectrum of Entry 8 of Table III.

Palladium acetate (5.6 mg, 0.025 mmol), mono-methyl isophthalate (90 mg, 0.5 mmol) and chlorobenzene (283 mg, 2.5 mmol), butyldi-1-adamantylphosphine (19.2 mg, 0.05 mmol), Cs$_2$CO$_3$ (358 mg, 1.1 mmol), molecular sieves 3 Å (155 mg) and anhydrous DMF (2.5 mL). After the reaction and workup the residue was dissolved in methanol (10 mL) and cooled to 0° C. (Trimethylsilyl)diazomethane in hexanes (5.0 ml of a 2.0M solution, 1 mmol) was added dropwise, the cooling bath was removed and the mixture stirred for 5 h. The solvent was removed under reduced pressure. Purification by preparative HPLC afforded 101 mg (75%) of a colorless oil. Analytical data are consistent with that of previously reported data.$^4$ $^1$H NMR (300 MHz, CDCl$_3$) δ 3.67 (s, 3H), 3.95 (s, 3H), 7.30-7.47 (m, 6H), 8.15-8.18 (m, 1H), 8.5 (br s, 1H). The $^1$H NMR spectrum is shown in FIG. 38.

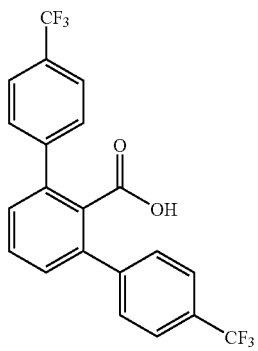

2,6-Bis(4-trifluoromethylphenyl)benzoic Acid (Entry 9, Table III)

Figure 39B:
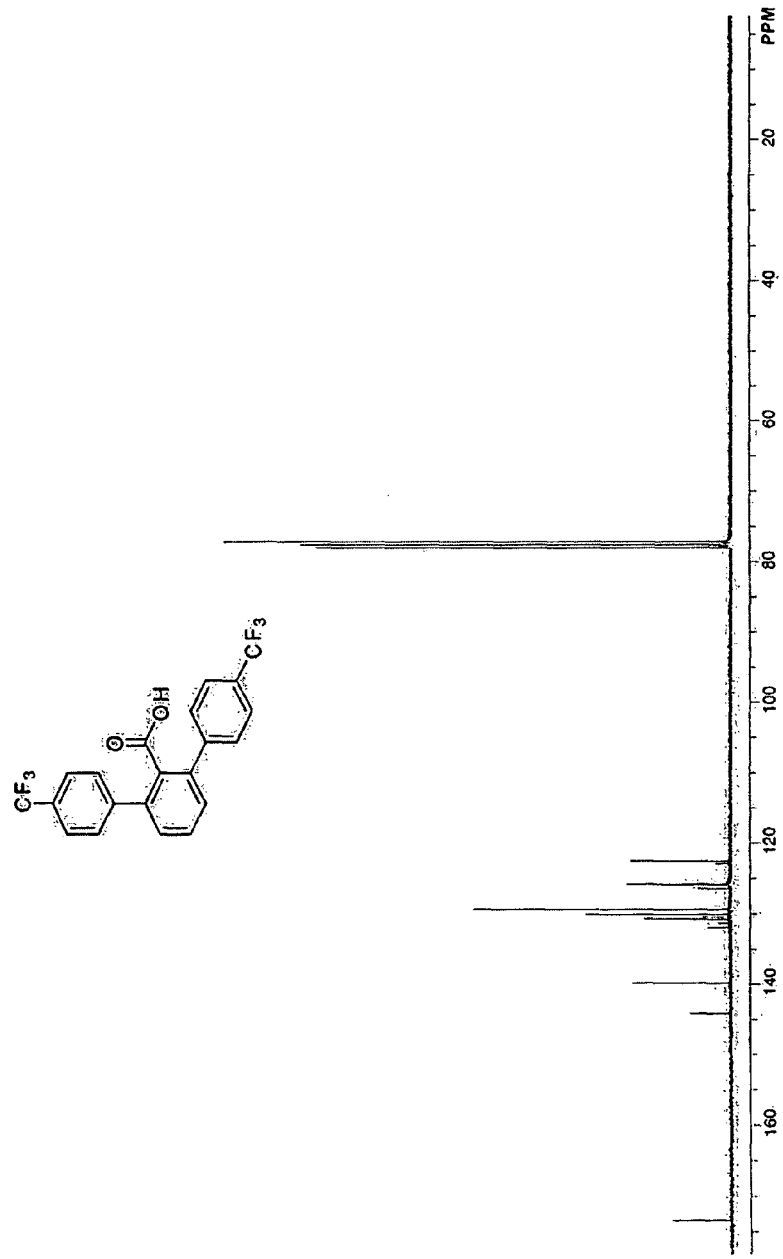
FIG. 39B depicts a $^{13}$C NMR spectrum of Entry 9 of Table III

Palladium acetate (5.6 mg, 0.025 mmol), benzoic acid (61 mg, 0.5 mmol) and 4-chlorobenzotrifluoride (271.5 mg 1.5 mmol), butyldi-1-adamantylphosphine (19.2 mg, 0.05 mmol), Cs$_2$CO$_3$ (358 mg, 1.1 mmol), molecular sieves 3 Å (155 mg) and anhydrous DMF (2.5 mL). After column chromatography 168 mg (82% v) of a white solid was obtained, nip 158-159° C. (isooctane). $R_f$-0.80 (1/9 ethyl acetate-dichloromethane). $^1$H NMR (300 MHz, CDCl$_3$) δ 7.38-7.40 (m, 2H), 7.48-7.50 (m, 4H), 7.55-7.58 (m, 1H), 7.61-7.64 (m, 4H). Carboxylate proton signal was not observed. $^{13}$C NMR (75 MHz, CDCl$_3$) 5124.1 (q, J-271.5 Hz), 125.3 (q, J-2.8 Hz), 128.8, 129.5, 130.1 (q, J-32.1 Hz), 130.1, 131.9, 139.2, 143.6, 172.8. FT-IR (neat, cm$^1$) υ 1702, 1325, 1127. Anal. calcd for C$_{21}$H$_{12}$F$_6$O$_2$ (410.31 g/mol): C, 61.47; H, 2.95. Found: C, 61.41, H, 2.98. The $^1$H NMR and $^{13}$C NMR spectra are shown in FIGS. 39A&B, respectively.

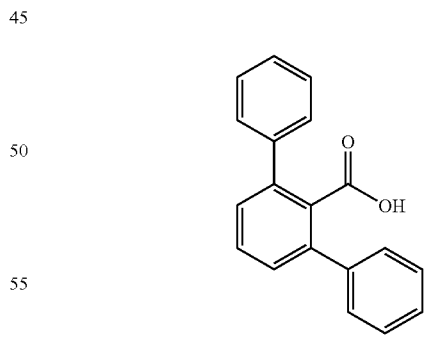

2,6-Diphenylbenzoic Acid (Entry 10, Table III)

Figure 43:
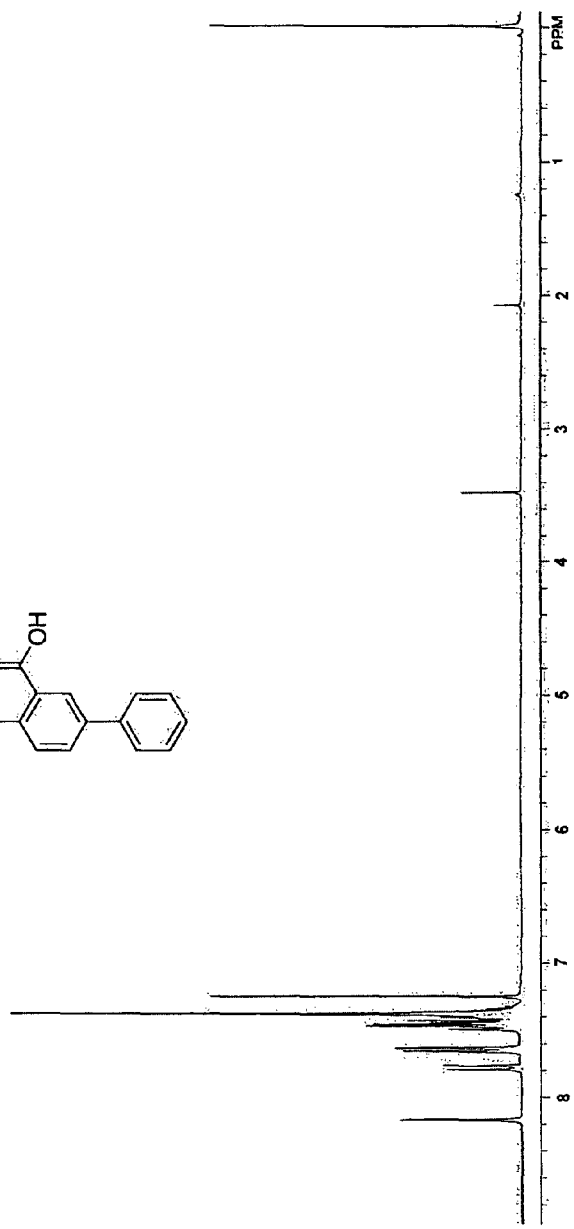
FIG. 43 depicts a $^1$H NMR spectrum of Entry 12 of Table III.

Palladium acetate (5.6 mg, 0.025 mmol), benzoic acid (61 mg, 0.5 mmol) and 4-chlorobenzene (283 mg, 2.5 mmol), butyldi-1-adamantylphosphine (19.2 mg, 0.05 mmol), Cam, (358 mg, 1.1 mmol), molecular sieves 3 Å (155 mg) and anhydrous DMF (2.5 mL). After flash chromatography and preparative HPLC 10 mg (10%) of 2-phenylbenzoic acid and 97 mg (71%) of 2,6-diphenylbenzoic acid was obtained. Analytical data are consistent with that of previously reported data.[5] $^1$H NMR (300 MHz, CDCl$_3$) δ 7.31-7.43 (m, 7H), 7.53-7.61 (m, 1H), 7.91-7.97 (m, 1H), 10.7 (br s, 1H). $^1$H NMR (300 MHz, CDCl$_3$) δ 7.35-7.41 (m, 12H), 7.48-7.53 (m, 1H). Carboxylate proton signal was not observed. The $^1$H NMR spectrum is shown in FIG. 40.

tography and preparative HPLC 97 mg (71%) of a white solid was obtained. Analytical data are consistent with that of previously reported data.[6] $^1$H NMR (300 MHz, CDCl[3]) δ 7.36-7.50 (m, 10H), 7.63-7.66 (m, 2H), 7.75-7.78 (m, 1H), 8.15-8.18 (m, 1H). Carboxylate proton signal was not observed. The $^1$H NMR spectrum is shown in FIG. 43.

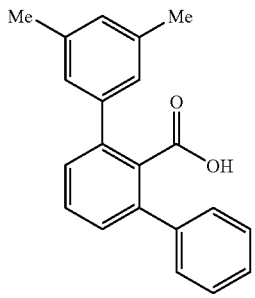

2-(3,5-Dimethylphenyl)-6-phenylbenzoic Acid
(Entry 11, Table III)

Figure 41:
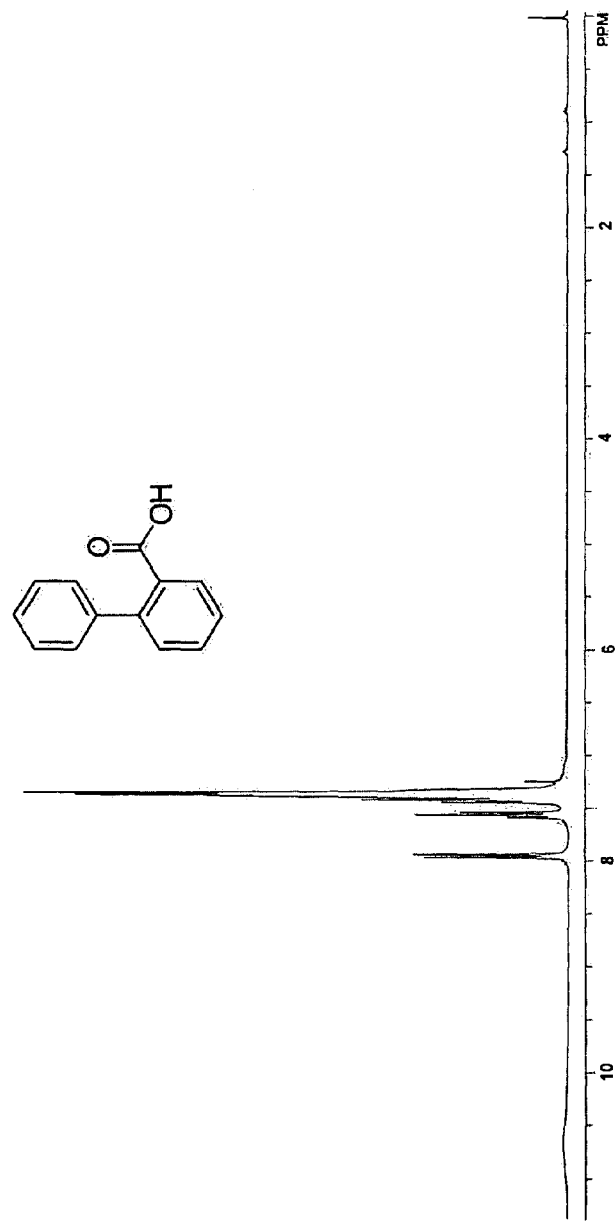
FIG. 41 depicts a $^1$H NMR spectrum of Entry 11 of Table III.
Figure 42A:
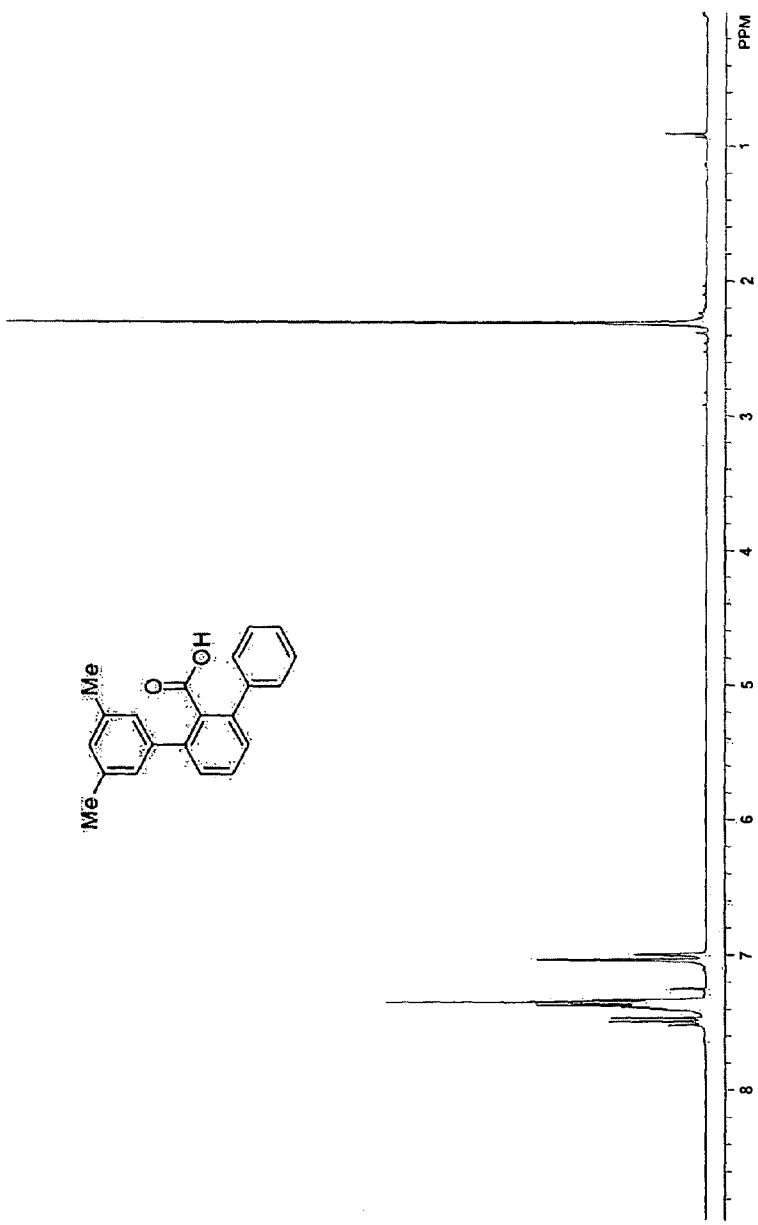
FIG. 42A depicts a $^1$H NMR spectrum of Entry 11 of Table III.
Figure 42B:
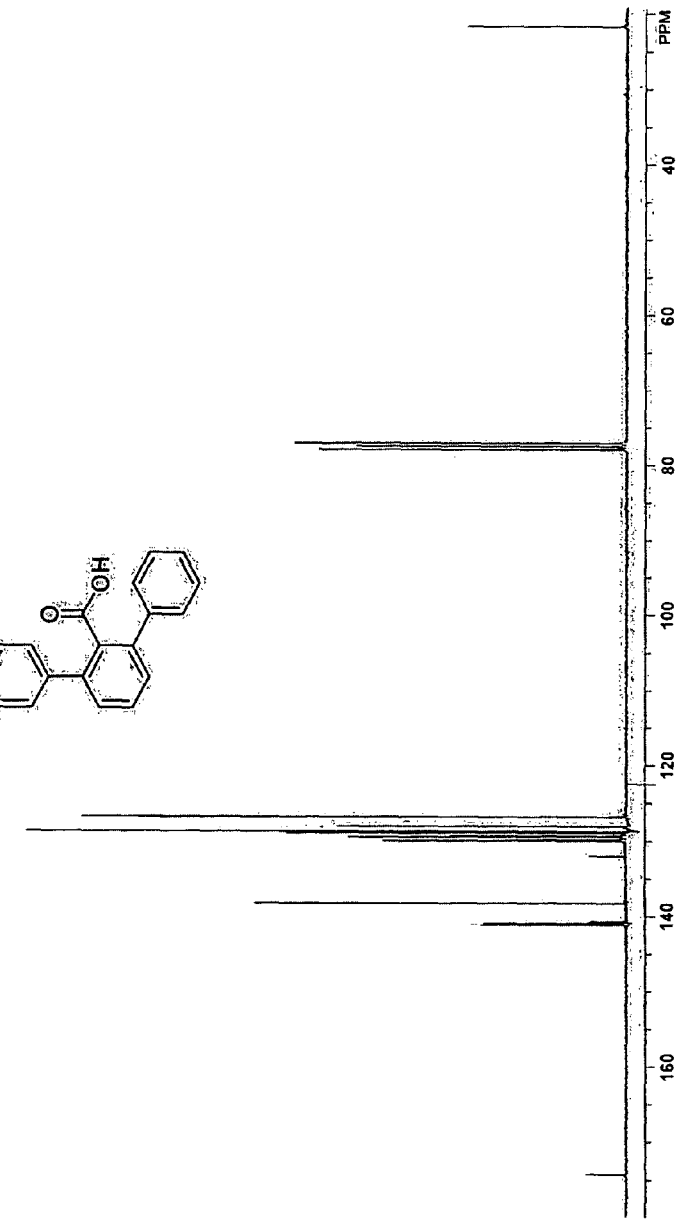
FIG. 42B depicts a $^{13}$C NMR spectrum of Entry 11 of Table III.

Palladium acetate (5.6 mg, 0.025 mmol), 2-phenylbenzoic acid (99 mg, 0.5 mmol) and 3,5-dimethylchlorobenzene (211 mg, 1.5 mmol), butyldi-1-adamantylphosphine (19.2 mg, 0.05 mmol), Cs$_2$CO$_3$ (358 mg, 1.1 mmol), molecular sieves 3 Å (155 mg and anhydrous DMF (2.5 mL). After flash chromatography and preparative HPLC 101 mg (67%) of a white solid was obtained, mp 198-200° C. (isooctane). R$_f$-0.79 (1/9 ethyl acetate-dichloromethane). $^1$H NMR (300 MHz, CDCl$_3$) δ 2.30 (s, 6H), 7.00 (s, 1H), 7.03 (s, 2H), 7.33-7.38 (m, 7H), 7.46-7.52 (m, 1H), 9.6 (br s, 1H). [1]C NMR (75 MHz, CDCl$_3$) δ 21.7, 122.5, 126.9, 128.1, 128.8, 129.0, 129.3, 129.5, 129.8, 130.0, 132.0, 138.3, 140.7, 141.0, 141.2, 174.2. FT-IR (neat, cm$^1$) υ 1688, 1295. Anal. calcd for C$_{21}$H$_{18}$O$_2$ (302.37 g/mol): C, 83.42; H, 6.00. Found: C, 83.13; H, 6.05. The $^1$H NMR spectrum of 2-phenylbenzoic acid is shown in FIG. 41. The $^1$H NMR and $^{13}$C NMR spectra of the product are shown in FIGS. 42A&E, respectively.

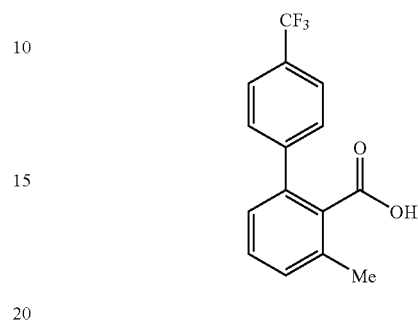

2-Methyl-6-(4-trifluomethylphenyl)benzoic Acid
(Entry 13, Table III)

Figure 44A:
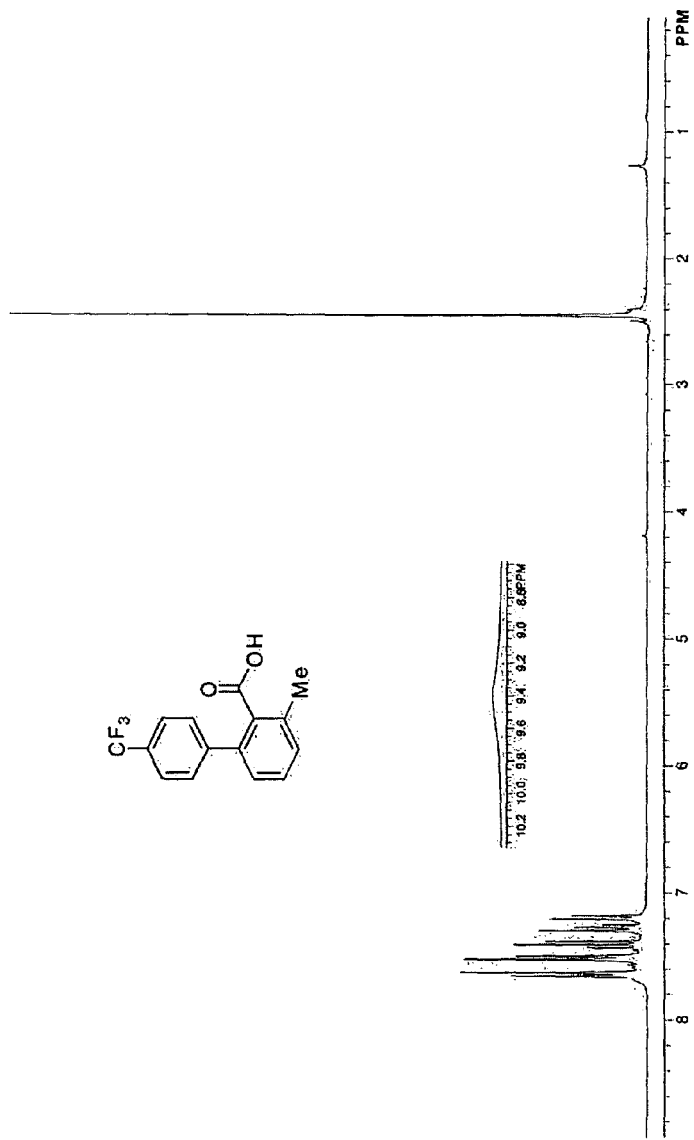
FIG. 44A depicts a $^1$H NMR spectrum of Entry 13 of Table III.

Palladium acetate (5.6 mg, 0.025 mmol), 2-methylbenzoic acid (68 mg, 0.5 mmol), 4-chlorobenzotrifluoride (181 mg, 1.0 mmol), butyldi-1-adamantylphosphine (19.2 mg, 0.05 mmol), Cs$_2$CO$_3$ (358 mg, 1.1 mmol), molecular sieves 3 Å (155 mg) and anhydrous DMF (2.5 mL). After column chromatography 101 mg (72%) of a white solid was obtained, mp 120-122° C. (isooctane). R$_f$-0.56 (1/9 ethyl acetate-dichloromethane). $^1$H NMR (300 MHz, CDCl$_3$) δ2.44 (s, 3H), 7.17-7.20 (m, 1H), 7.25-7.29 (m, 1H), 7.35-7.41 (m, 1H), 7.47-7.51 (m, 2H), 7.60-7.65 (m, 2H), 9.4 (br s, 1H). $^{13}$C NMR (75 MHz, CDCl$_3$) δ20.4, 124.7 (q, J-271.7 Hz), 125.8 (q, J-4.0 Hz), 127.9, 129.3, 130.3 (q, J-31.5 Hz), 130.55, 130.58, 132.4, 136.4, 139.4, 144.8, 175.5. FT-IR (neat cm$^1$) 1697, 1326, 1119. Anal. calcd for C$_{15}$H$_{11}$F$_3$O$_2$ (280.24 g/mol): C, 64.29; H, 3.96. Found: C, 63.69; H, 3.84. The $^1$H NMR and $^{13}$C NMR spectra are shown in FIGS. 44A&B, respectively.

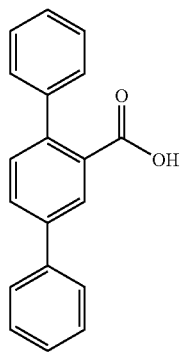

2,5-Diphenylbenzoic Acid (Entry 12, Table III)

Palladium acetate (5.6 mg, 0.025 mmol), 3-phenylbenzoic acid (99 mg, 0.5 mmol) and 4-chlorobenzene (169 mg, 1.5 mmol), butyldi-1-adamantylphosphine (19.2 mg, 0.05 mmol), Cs2CO3 (358 mg, 1.1 mmol), molecular sieves 3 Å (155 mg) and anhydrous DMF (2.5 mL). After flash chroma-

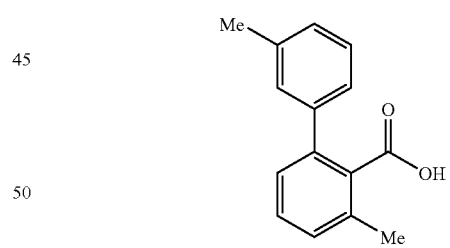

2-Methyl-6-(3-methylphenyl)benzoic Acid (Entry 14, Table III)

Figure 45A:
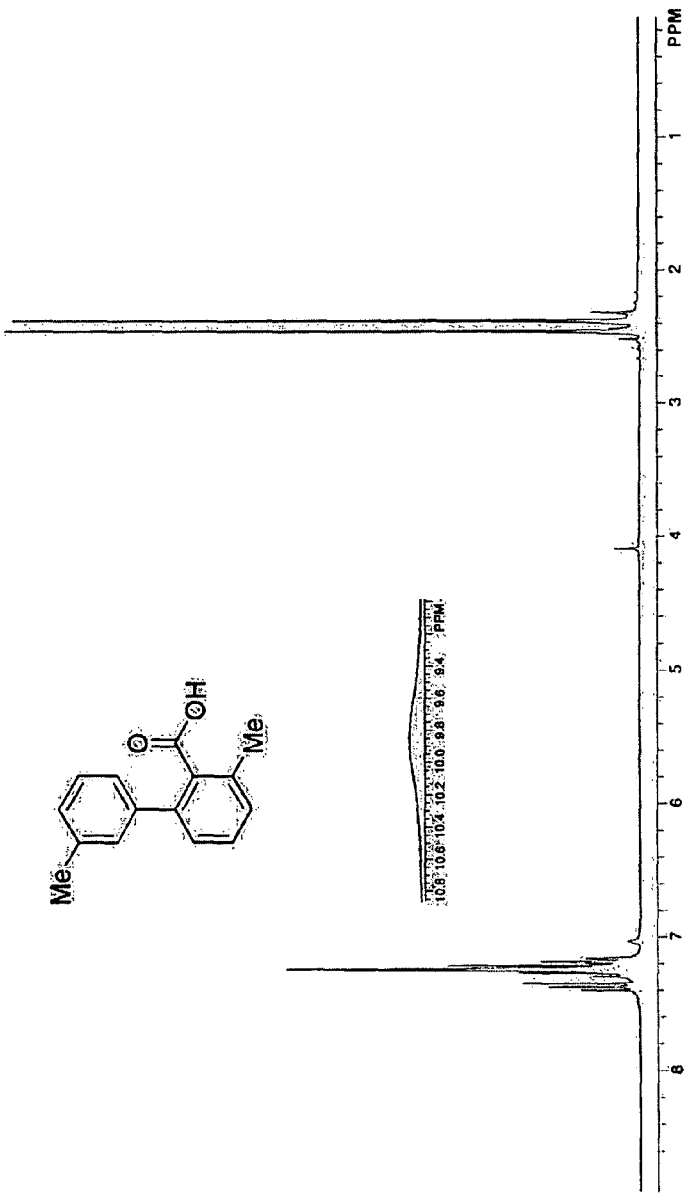
FIG. 45A depicts a $^1$H NMR spectrum of Entry 14 of Table III.

Palladium acetate (5.6 mg, 0.025 mmol), 2-methylbenzoic acid (68 mg, 0.5 mmol), 3-chlorotoluene (127 mg, 1.0 mmol), butyldi-1-adamantylphosphine (19.2 mg, 0.05 mmol), Cs$_2$CO$_3$ (358 mg 1.1 mmol), molecular sieves 3 Å (155 mg) and anhydrous DMF (2.5 mL). After column chromatography and preparative HPLC 103 mg (91%) of a white solid was obtained, mp 88-89° C. (isooctane). R$_f$-0.22 (1/9 ethyl acetate-hexanes). $^1$H NMR (300 MHz, CDCl$_3$) δ2.36 (s, 3H), 2.44 (s, 3H), 7.17-7.25 (m, 6H), 7.33-7.36 (m, 1H), 9.8 (br s, 1H). $^{13}$C NMR (75 MHz, CDCl$_3$) δ20.5, 22.0, 125.9, 128.0, 128.8, 128.9, 129.7, 130.2, 132.6, 135.9, 138.6, 140.8, 141.1, 176.0. A signal for one aromatic carbon could not be located. FT-IR (neat, cm$^1$) υ 1688, 1282. Anal. calcd for $C_{15}H_{14}O_2$ (226.27 g/mol): C, 79.62; H, 6.24. Found: C, 79.91; H, 6.23. The $^1$H NMR and 13C NMR spectra are shown in FIGS. 45A&B, respectively.

A. Procedure for the Screening of Phosphine Ligands

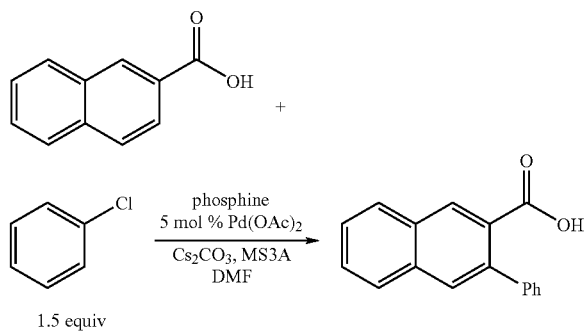

A 2-dram vial equipped with a magnetic stir bar was charged with Pd(OAc)$_2$ (5.6 mg, 0.025 mmol), 2-naphthoic acid (86 mg; 0.5 mmol) and chlorobenzene (85 mg; 0.75 mmol). The vial was flushed with argon, capped and placed inside a glovebox. To the above mixture was added a phosphine ligand (10 mol %), Cs$_2$CO$_3$ (358 mg; 1.1 mmol), molecular sieves 3 Å (155 mg) and anhydrous DMF (2.5 mL). The sealed vial was taken out of the glovebox, stirred at room temperature for 2 h and placed in a pre-heated oil bath (145° C.) for 24 h. The reaction mixture was allowed to cool to room temperature and quenched with 15% aqueous HCl (4 mL). Hexadecane internal standard (0.1 mL) was added. Resulting suspension was extracted with ethyl acetate (3×3 mL) and the organic layer was filtered through a pad of Celite®. An aliquot of the solution was treated with excess (trimethylsilyl)diazomethane (2.0 M in hexanes, until yellow color persisted) and analyzed by GC. Response factors were obtained by separate injection of a known mixture of internal standard, methyl ester of 2-naphthoic acid and methyl ester of 3-phenyl-2-naphthoic acid.

TABLE XII

Evaluation of Phosphine Ligands (L)

| Entry | 10 mol % L and 5 mol % Pd | % Yield by GC$^a$ |
|---|---|---|
| A1 | Cy$_3$P and Pd$_2$(dba)$_3$CHCl$_3$ | 3 |
| A2 | (tBu$_3$P)$_2$Pd | 2 |
| A3 | Cy$_3$P and Pd(OAc)$_2$ | 46 |
| A4 | tBu$_2$MeP-HBF$_4$ and Pd(OAc)$_2$ | 58 |
| A5 | nOctyl$_3$P and Pd(OAc)$_2$ | 7 |

TABLE XII-continued

Evaluation of Phosphine Ligands (L)

| Entry | 10 mol % L and 5 mol % Pd | % Yield by GC$^a$ |
|---|---|---|
| A6 | Ph$_3$P and Pd(OAc)$_2$ | 1 |
| A7 | tBu(Cy)$_2$P and Pd(OAc)$_2$ | 57 |
| A8 | nBu(Ad)$_2$P and Pd(OAc)$_2$ | 65 |
| A9 | p-Tol$_3$P and Pd(OAc)$_2$ | 2 |
| A10 | DPPP and Pd(OAc)$_2$ | 7 |
| A11 | none | <1 |

$^a$Determined using hexadecane as internal standard.

B. Procedure for the Screening of Reagent Quality

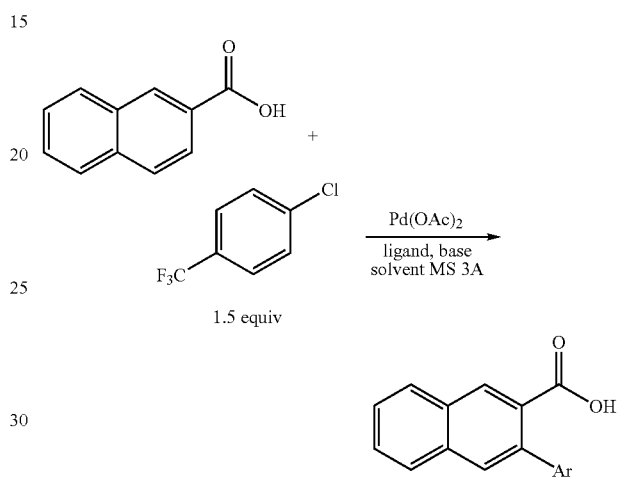

A 2-dram vial equipped with a magnetic stir bar was charged with Pd(OAc)$_2$ (5.6 mg, 0.025 mmol), 2-naphthoic acid (86 mg, 0.5 mmol) and 4-chlorobenzotrifluoride (136 mg, 0.75 mmol). The vial was flushed with argon, capped and placed inside the glovebox. Depending on the experiment, to each vial was added a combination of these: ligand (10 mol %), Cs$_2$CO$_3$ (2.2 equiv), molecular sieves 3 Å (155 mg) and DMF (2.5 mL) (see Table S2 for exact conditions). The sealed vial was taken out of the glovebox, stirred at room temperature for 2 h and placed in a pre-heated oil bath (145° C.) for 24 h. The reaction mixture was allowed to cool to room temperature, quenched with 15% aqueous HCl (4 mL) and hexadecane (0.1 mL) was added as internal standard. Resulting suspension was extracted with ethyl acetate (3×3 mL) and the organic layer filtered through a pad of Celite®. An aliquot was treated with excess (trimethylsilyl)diazomethane (2.0 M in hexanes; until yellow color persisted) and analyzed by GC. Response factors were obtained by separate injection of a known mixture of internal standard, and methyl esters of 2-naphthoic acid and 3-(4-trifluoromethylphenyl)-2-naphthoic acids.

TABLE XIII

Evaluation of Reagent Quality

| Entry | DMF | MS 3 Å$^a$ | Cs$_{2CO_3}$$^b$ | % Yield by GC$^c$ |
|---|---|---|---|---|
| B1 | Aldrich (anhydrous) | flame-dried | dry | quantitative |
| B2 | Fluka (anhydrous) | flame-dried | dry | quantitative |
| B3 | Aldrich (anhydrous) | none | dry | 19 |
| B4 | Aldrich (ReagentPlus™) | wet | dry | quantitative |
| B5 | Aldrich (ReagentPlus™) | wet | wet | quantitative |
| B6 | Acros (regular) | flame-dried | dry | quantitative |
| B7 | Acros (regular) | wet | wet | quantitative |

TABLE XIII-continued

Evaluation of Reagent Quality

| Entry | DMF | MS 3 Å[a] | $Cs_2CO_3$[b] | % Yield by GC[c] |
|---|---|---|---|---|
| B8 | Aldrich (anhydrous) | wet | wet | 89 |
| B9 | Aldrich (anhydrous) | flame-dried, air-flushed[d] | dry | 97 |

[a]Flame-dried under reduced pressure for at least 2 h. Wet: commercial sieves, not dried, kept without special precautions under air.
[b]Dried at 170° C. under reduced pressure for at least 24 h. Wet: commercial material, stored without special precautions.
[c]Determined using hexadecane as internal standard.
[d]After being taken out of the glovebox, 1 mL of air was injected into reaction mixture and vial was resealed.

C. Procedure for the Determination of Regioselectivity of Arylation

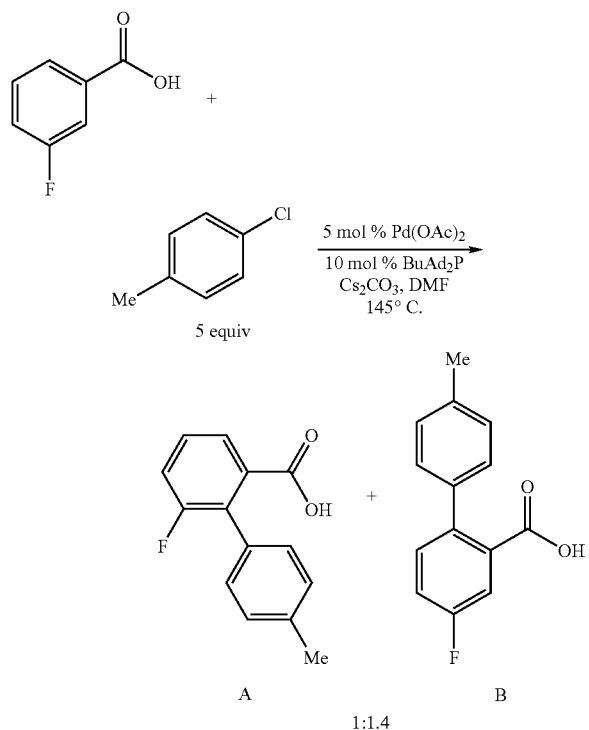

1:1.4

Figure 46:
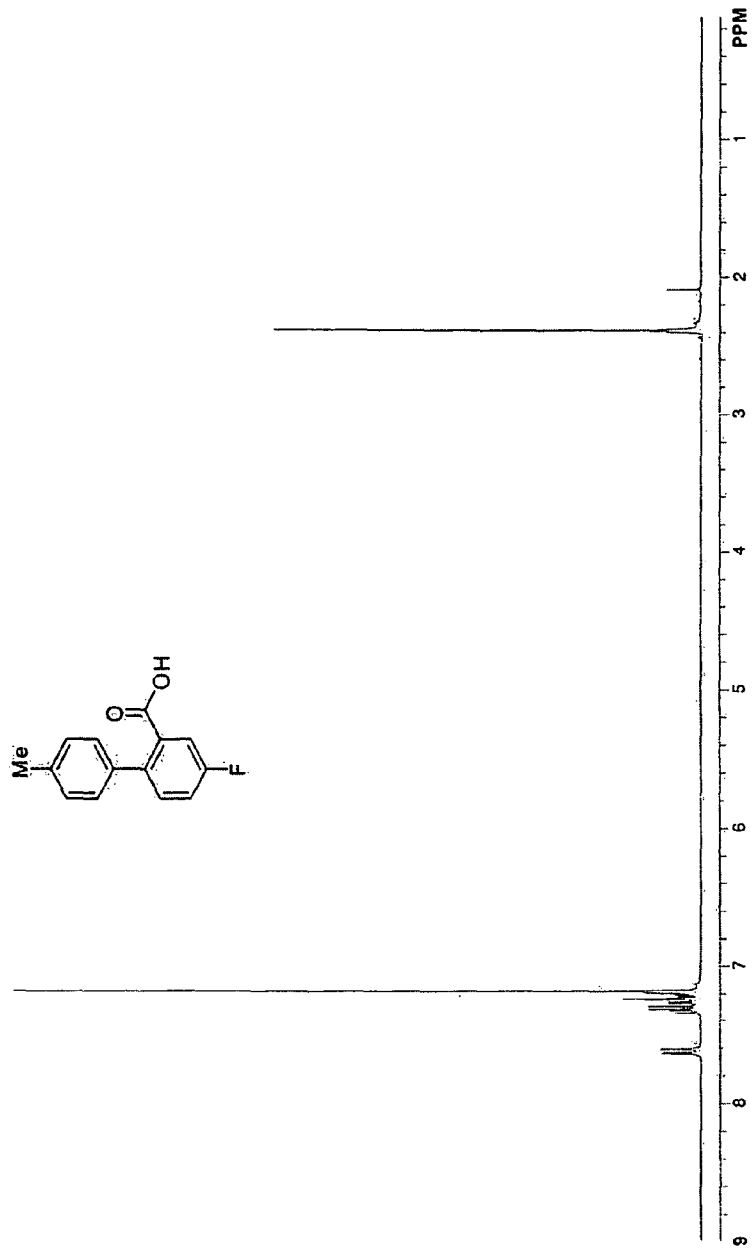
FIG. 46 depicts a $^1$H NMR spectrum of 3-Fluoro-2-(4-methylphenyl)benzoic acid.
Figure 47A:
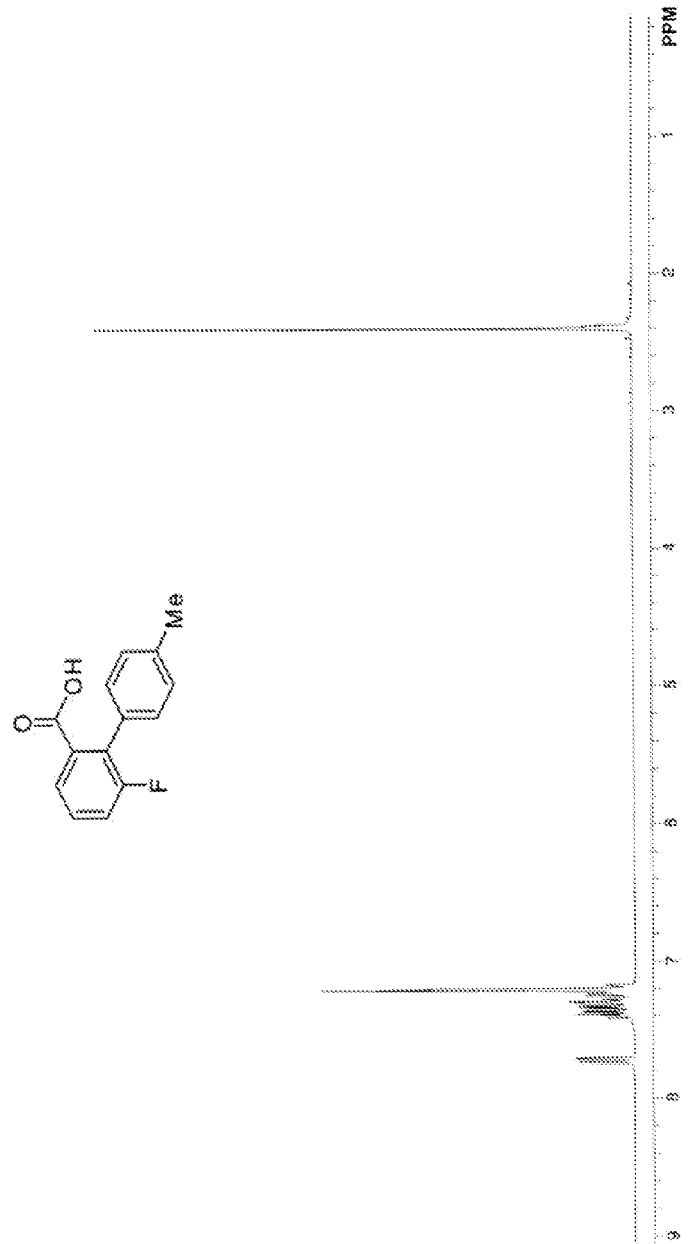
FIG. 47A depicts a $^1$H NMR spectrum of 3-Fluoro-2-(4-methylphenyl)benzoic acid.
Figure 47B:
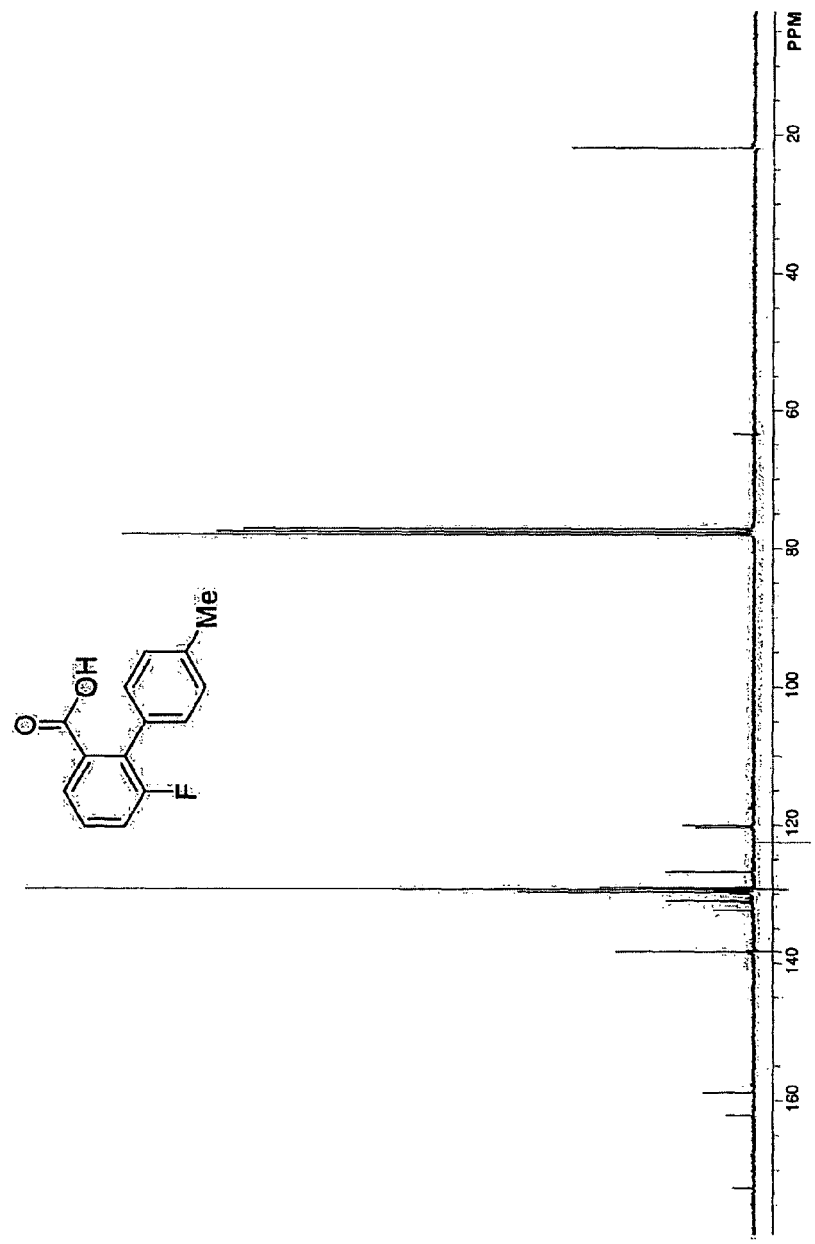
FIG. 47B depicts a $^{13}$C NMR spectrum of 3-Fluoro-2-(4-methylphenyl)benzoic acid.

Outside the glovebox a 2-dram vial equipped with a magnetic stir bar was charged with Pd(OAc)$_2$ (5.6 mg, 5 mol %), 3-fluorobenzoic acid (95 mg, 0.5 mmol) and chlorotoluene (625 mg, 5 mmol). The vial was flushed with argon, capped and placed inside a glovebox. To this mixture was added butyldi-1-adamantylphosphine (19.2 mg, 0.05 mmol), Cs$_2$CO$_3$ (325 mg), molecular sieves 3 Å (155 mg) and anhydrous DMF (2.5 mL). The sealed vial was taken out of the glovebox, stirred at room temperature for 2 h and placed in a preheated oil bath (145° C.) for ~3 h (before the onset of biarylation as determined by GC). The reaction mixture was allowed to cool to room temperature and quenched with 15% aqueous HCl (4 mL). Resulting suspension was extracted with ethyl acetate (3×3 mL) and the organic layer filtered through a pad of Celite®. The regioisomers were separated by preparative HPLC and dried under reduced pressure (50° C.).

a) 5-Fluoro-2-(4-methylphenyl)benzoic acid (30 mg, 26%). $^1$H NMR (300 MHz, CDCl$_3$) δ 2.39 (s, 3H), 7.19-7.35 (m, 6H), 7.62 (dd, J-8.6 Hz, 3.0 Hz, 1H). Signal of carboxylate proton could not be located. Analytical data are consistent with that of previously reported data.[7] The $^1$H NMR spectrum is shown in FIG. 46.

b) 3-Fluoro-2-(4-methylphenyl)benzoic acid (21 mg, 18%), mp 154-156° C. (isooctane), R$_f$-0.50 (1/9 ethyl acetate-dichloromethane). $^1$H NMR (300 MHz, CDCl$_3$) δ 2.40 (s, 3H), 7.17-7.41 (m, 7H), 7.72 (d, J-7.2 Hz). Signal of carboxylate proton could not be located. NMR (75 MHz, CDCl$_3$, C—F coupling constants assigned where possible list of signals where assignment not possible) δ 21.8, 120.0, 120.3, 126.8, 126.9, 128.8, 129.0, 129.1, 129.4, 129.7, 130.9, 131.3, 132.3, 138.3, 160.5 (d, J-244.5 Hz), 172.5. $^{13}$F NMR (283 MHz, CDCl$_3$) δ -160.9 (dd, J-8.6 Hz, 5.9 Hz). FT-IR (neat, cm$^1$) υ 1706, 1450, 1295, 1263. The $^1$H NMR and 13C NMR spectra are shown in FIGS. 47A&B, respectively.

D. Procedure for the Determination of Intramolecular Kinetic Isotope Effect (KIE)

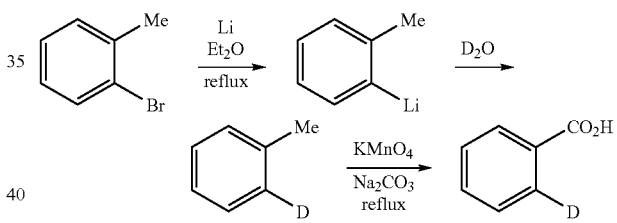

Synthesis of 2-deuteriobenzoic Acid a) A 200 mL flame-dried Schlenk flask equipped with a magnetic stir bar was charged with lithium metal in mineral oil (5 g, 720 mmol). The lithium metal was sequentially rinsed with toluene (2×30 mL) and ether (2×30 mL). The metal was suspended in 100 mL of ether and cooled in an ice bath. Under argon atmosphere, a solution of 2-bromotoluene (25 g, 146 mmol) in ether (40 mL) was added dropwise. The resulting suspension was allowed to warm to room temperature and stirred for an additional 2 hours then refluxed for 12 hours. After cooling to room temperature the mixture was filtered. The reaction vessel and the residue was rinsed with Et$_2$O. The filtrate was cooled in an ice bath and quenched with D$_2$O (5 mL) and allowed to warm to room temperature overnight. The mixture was diluted with water (100 mL) and the organic phase was separated. The organic phase was washed with water (3×100 mL followed by drying with MgSO$_4$. The mixture was distilled collecting diethyl ether and then 2-deuteriotoluene (7.6 g, 56%*).

b) A round-bottom flask equipped with a stir bar and condenser was charged with 2-deuteriotoluene (2.9 g, 31 mmol), KMnO$_4$ (12 g 76 mmol), Na$_2$CO$_3$ (1.5 g, 14 mmol) and water (100 ml). The suspension was refluxed for 8 hours then cooled to room temperature. The mixture was filtered through a pad of Celite®, acidified with 12M HCl, and extracted with dichloromethane (3×20 mL). The dichloromethane layer was washed with water. The crude product was recrystallized from water to yield 2.3 g (60%) of 2-deuteriobenzoic acid as fine white needles. The deuterium content was checked by NMR and EI-MS.

Determination of Intramolecular Kinetic Isotope Effect

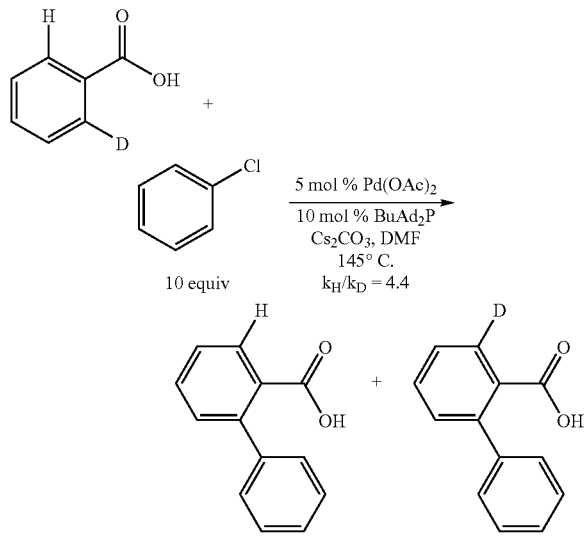

Outside the glovebox a 2-dram vial equipped with a magnetic stir bar was charged with Pd(OAc) (5.6 mg, 5 mol %), 2-deuteriobenzoic acid (61.5, 0.5 mmol) and chlorobenzene (565 mg, 5 mmol). The vial was flushed with argon, capped and placed inside a glovebox. To this mixture was added butyldi-1-adamantylphosphine (19.2 mg, 0.05 mmol), $Cs_2CO_3$ (325 mg), molecular sieves 3 Å (155 mg) and anhydrous DMF (2.5 mL). The sealed vial was taken out of the glovebox, stirred at room temperature for 2 h and placed in a preheated oil bath (145° C.) for 75 min. The reaction mixture was allowed to cool to room temperature and quenched with 15% aqueous HCl (4 mL). Resulting suspension was extracted with ethyl acetate (3×3 mL) and the organic layer filtered through a pad of Celite®. The product was purified by preparative HPLC and dried under reduced pressure (50° C.) for 12 h. The ratio of the deuterated to non-deuterated product was found to be 4.4:1 by $^1$H NMR (integration of the doublet at 7.94 ppm (o-H) relative to a triplet at 7.56 ppm (p-H)). A similar experiment using 10 mol % Pd(OAc)$_2$ and 20 mol % BuAd$_2$P gave the same result.

E. Procedure for the Determination of Intermolecular Kinetic isotope effect (KIE)

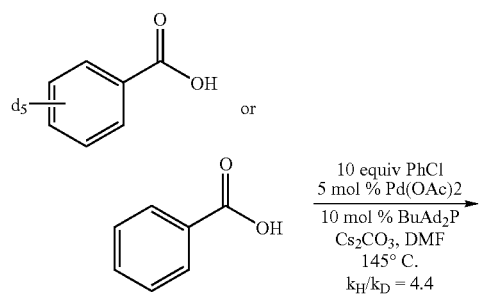

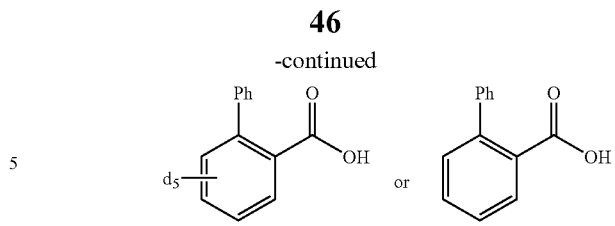

The 1,2,3,4,5-pentadeuteriobenzoic acid was prepared by KMnO$_4$ oxidation of the perdeuterated toluene by using a method used in synthesis of 2-deuterobenzoic acid.

Outside the glovebox a 2-dram vial equipped with a magnetic stir bar was charged with Pd(OAc)$_2$ (5.6 mg, 5 molY %), benzoic acid (either H$_5$- or D$_5$) (0.5 mmol and chlorobenzene (565 mg, 5 mmol). The vial was flushed with argon, capped and placed inside a glovebox. To this mixture was added butyldi-1-adamantylphosphine (19.2 mg, 0.05 mmol), Cs$_2$CO$_3$ (325 mg), molecular sieves 3 Å (155 mg) and anhydrous DMF (2.5 mL). The sealed vial was taken out of the glovebox, stirred at room temperature for 2 h and placed in a preheated oil bath (145° C.) and taken out after the indicated reaction time (see Table S3 and S4). After cooling the reaction mixture to room temperature, a weighed amount of hexadecane internal standard was added (~25 mg) and the mixture was quenched with 15% aqueous HCl (4 mL). Resulting suspension was extracted with ethyl acetate (3×3 mL) and the organic layer was filtered through a pad of Celite® and diluted with ethyl acetate (1 mL). An aliquot was analyzed by GC. The response factors were determined by a separate injection of a known mixture of starting material, product and internal standard.

TABLE XIV

Reaction of Benzoic Acid with PhCl under Optimum Conditions Versus Time in Minutes

| SM$_i$ | SM$_f$ | time, min | log (SM$_i$/SM$_f$) × 10$^3$ |
|---|---|---|---|
| 0.5000 | 0.4881 | 30 | 10.5 |
| 0.5000 | 0.4869 | 45 | 11.5 |
| 0.5000 | 0.4774 | 60 | 20.1 |
| 0.5000 | 0.4714 | 75 | 25.6 |
| 0.5000 | 0.4483 | 105 | 47.4 |

Figure 21:
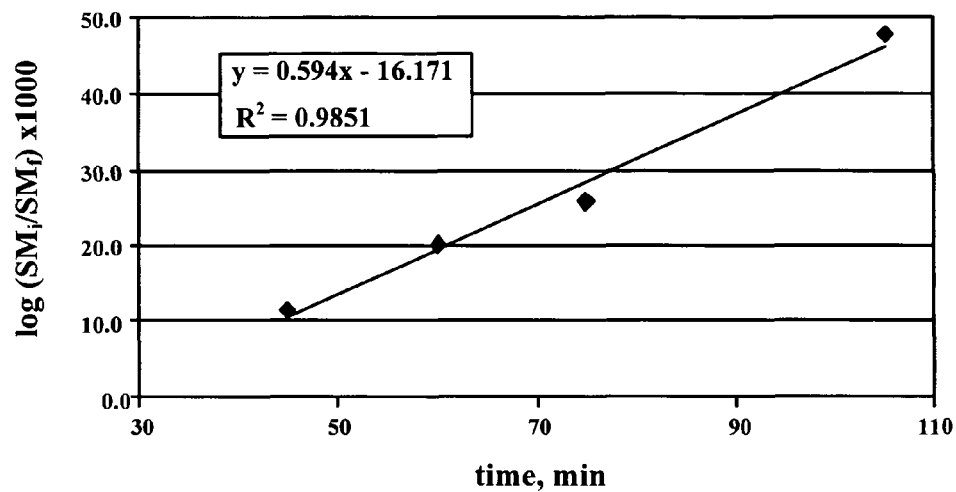
FIG. 21 depicts a graph of the reaction of Benzoic Acid with PhCl.

Referring now to FIG. 21, a. plot of time in minutes versus log(SM$_i$/SM$_f$)×10$^3$ for the data of Table XIV is shown.

TABLE XV

Reaction of 1,2,3,4,5-Pentadeuteriobenzoic Acid with PhCl under Optimum Conditions Versus Time in Minutes

| SM$_i$ | SM$_f$ | time, min | log (SM$_i$/SM$_f$) × 10$^3$ |
|---|---|---|---|
| 0.5000 | 0.4977 | 30 | 2.0 |
| 0.5000 | 0.4967 | 45 | 2.9 |
| 0.5000 | 0.4948 | 60 | 4.6 |
| 0.5000 | 0.4919 | 75 | 7.1 |
| 0.5000 | 0.4877 | 105 | 10.8 |

Figure 22:
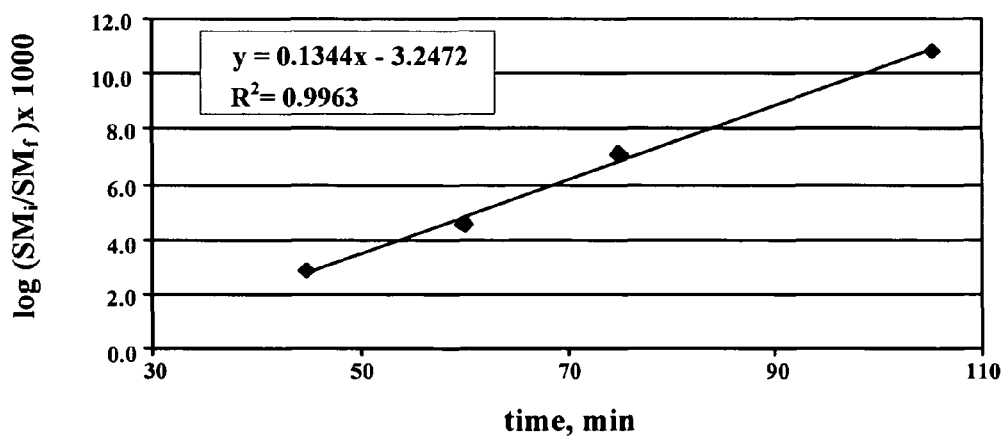
FIG. 22 depicts a graph of the reaction of 1,2,3,4,5-Pentadeuteriobenzoic Acid with PhCl.

Referring now to FIG. 22, a. plot of time in minutes versus log(SM$_i$/SM$_f$)×10$^3$ for the data of Table XV is shown.

E. Procedure for the Decarboxylation

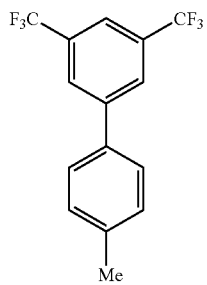

3,5-Bis(Trifluoromethyl)-4'-Methylbiphenyl

Figure 48:
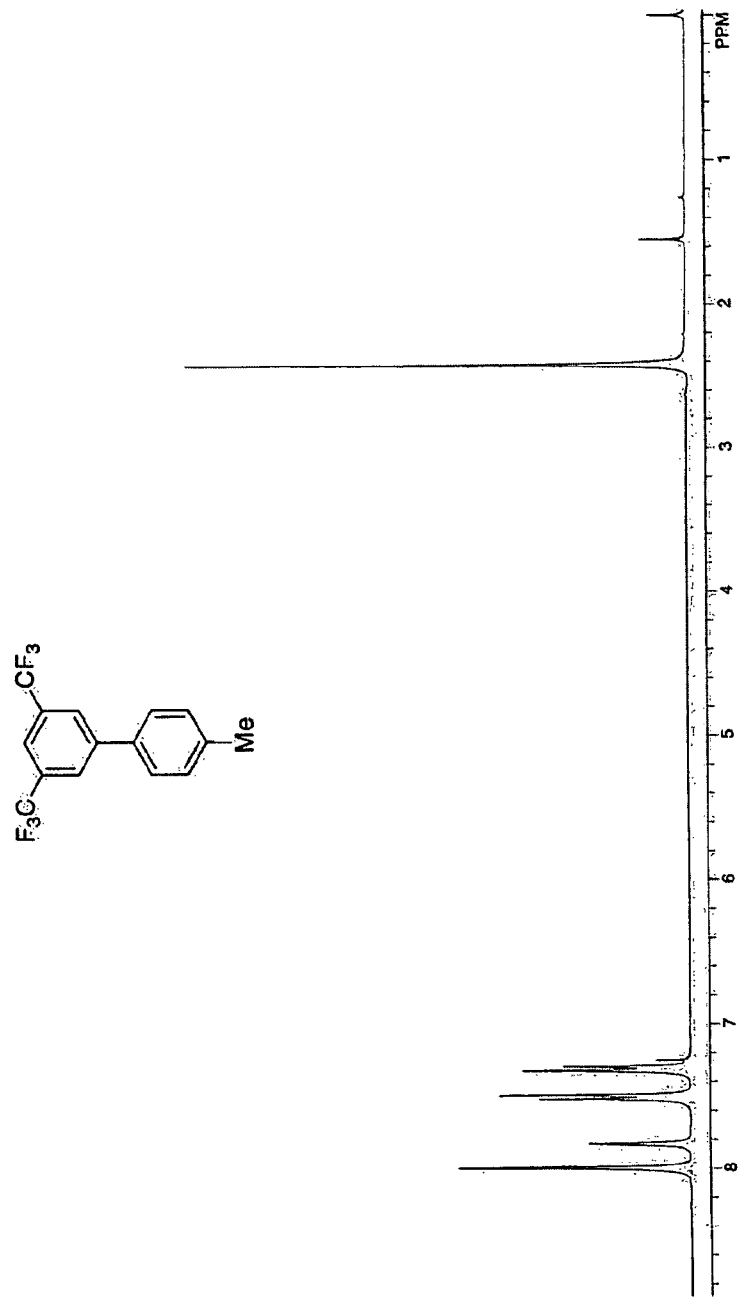
FIG. 48 depicts a $^1$H NMR spectrum of 3,5-Bis(Trifluoromethyl)-4'-Methylbiphenyl.

Outside the glovebox a 2-dram vial equipped with a magnetic stir bar was charged with CuO (12 mg, 0.15 mmol), 1,10-phenanthroline (27 mg, 0.15 mmol), quinoline (19 mg, 0.15 mmol), $K_2CO_3$ (21 mg, 0.15 mmol) and 2-(3,5-bis(trifluoromethyl)phenyl)-5-methylbenzoic acid (115 mg, 33 mmol). The vial was flushed with argon, capped and placed inside a glovebox. To this mixture was added anhydrous NMP (3 mL), the vial was sealed and taken out of the glovebox. The mixture was stirred at 160° C. for 24 h. The mixture was allowed to cool to room temperature and quenched with 15% KOH (4 mL). Resulting suspension was extracted with dichloromethane (3×3 mL) and the organic layer filtered through a pad of Celite®. The filtrate was concentrated carefully under vacuum (~30° C.) to a volume of about 2 mL. The mixture was adsorbed on silica gel and subjected to flash chromatography (hexanes). After removal of the solvent, the residue was dried under reduced pressure (~30° C.) to yield a colorless oil (86 mg, 86%). Analytical data are consistent with that of previously reported data.[8] $^1$H NMR (300 MHz, $CDCl_3$) δ2.42 (s, 3H), 7.31 (d, J-8.1 Hz, 2H), 7.51 (d, J-8.1 Hz, 2H), 7.83 (s, 1H), 8.00 (s, 2H). The $^1$H NMR spectrum is shown in FIG. 48.

F. Arylation by Using Either Pd(II) or Pd(0) Sources

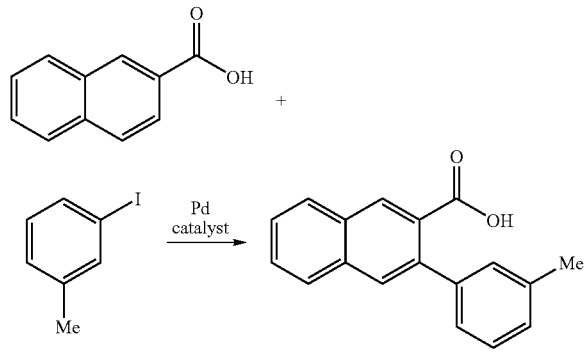

A mixture of a Pd complex (0.2 mmol Pd), 2-naphthoic acid (x g, 1 mmol), 3-iodotoluene (x g, 3 mmol), and AcOH (0.2 mL) was heated at 130° C. for 30 h. GC analysis was performed as in the case of isotope effect determination:
- a) $Pd(tBu_3)_2$, no arylation observed by GC.
- b) $Pd_2(dba)_3*CHCl_3$, no arylation observed by GC.
- c) $Pd(OAc)_2$, 24% conversion to the arylated product by GC.

It was also determined that under any of the above conditions 1-hydroxy-2-naphthoic, 3-hydroxy-2-naphthoic, 1-acetoxy-2-naphthoic, and 3-acetoxy-2-naphthoic acids were not formed (GC analysis of crude reaction mixtures; comparison with authentic samples).

REFERENCE CITED IN SECTION II 1. (a) Croxall, W. J.; Sowa, F. J. Nieuwland, J. A. *J. Am. Chem. Soc.* 1935, 57, 1549. (b) Lazareva, A.; Daugulis, O. *Org. Lett* 2006, 8, 5211.
2. Screttas, C. G.; Micha-Screttas, M. J. *Organomet. Chem.* 1985, 290, 1.
3. Buckles, R. E.; Filler, R.; Hilfman, L. *J. Org. Chem.* 1952, 17, 233.
4. Matsui, T; Matsushita, Y. (Jpn. Kokai Tokkyo Koho) 1994 JP 19941004.
5. a) Gutsche, C. D.; Johnson, W. S. *J. Am. Chem. Soc.* 1946, 68, 2239. b) Oi, S.; Aizawa, E.; Ogino, Y.; Inoue, Y. *J. Org. Chem.* 2005, 70, 3113.
6. Ames, G. R.; Davey, W. *J. Chem. Soc.* 1957, 3480.
7. Takasugi, H.; Inoue, Y.; Terasawa, T.; Nagayoshi, A.; Furukawa, Y.; Mikami, M.; Hinoue, K.; Ohtsubo, M.; Fukumoto, D. WO2002-JP11034, 2002.
8. Brune, H.-A.; Hess, R.; Schmidtberg, G. *Z Naturforsch* 1984, 39b, 1772.

Figure 23:
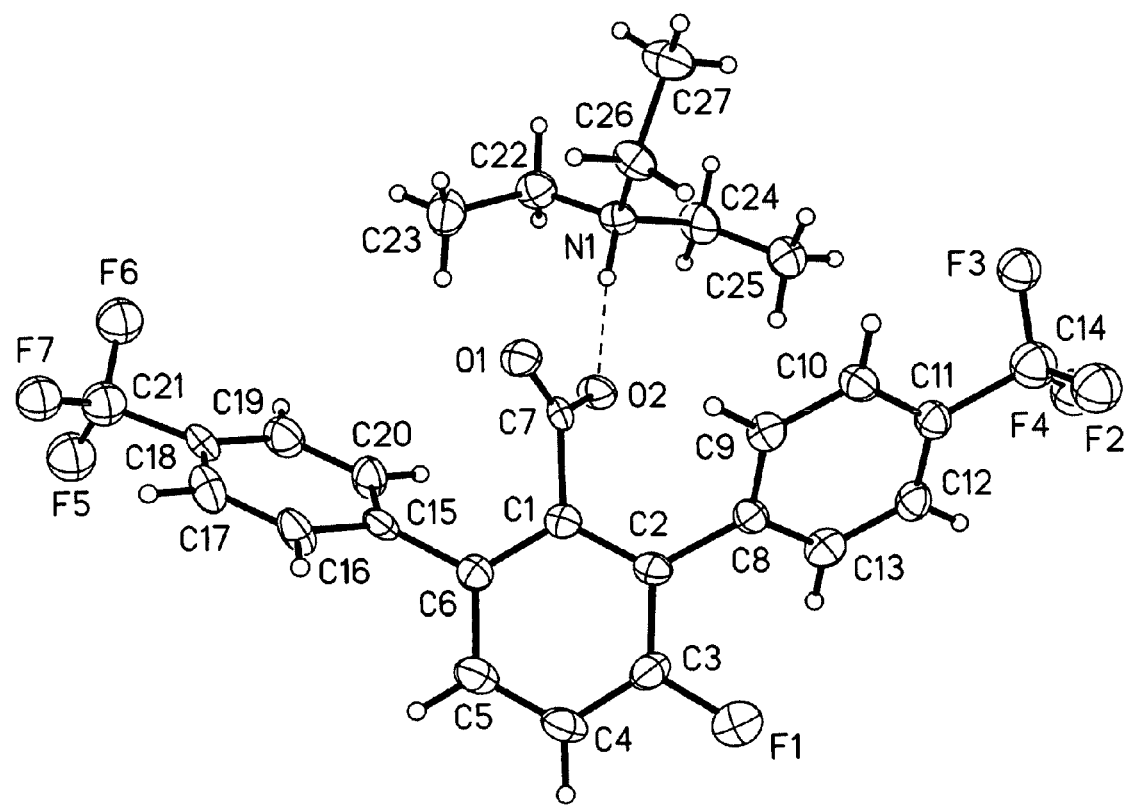
FIG. 23 depicts a crystal structure of the compound of Entry 4 of Table III.

G. X-Ray Data for Triethylammonium 3-Fluoro-2,6-bis(4-Trifluoromethyl-phenyl)Benzoate All measurements were made with a Siemens SMART platform diffractometer equipped with a 4K CCD APEX II detector. A hemisphere of data (1271 frames at 6 cm detector distance) was collected using a narrow-frame algorithm with scan widths of 0.30% in omega and an exposure time of 35 s/frame. The data were integrated using the Bruker-Nonius SAINT program, with the intensities corrected for Lorentz factor, polarization, air absorption, and absorption due to variation in the path length through the detector faceplate. A psi scan absorption correction was applied based on the entire data set. Redundant reflections were averaged Final cell constants were refined using 2066 reflections having I>10\s(I), and these, along with other information pertinent to data collection and refinement, are listed in Table XVI. The Laue symmetry was determined to be –1, and the space group was shown to be either P1 or P–1. The asymmetric unit consists of two independent cation/anion pairs which differ mainly in the orientations of the cations. Each of the CF3 groups was found to be disordered, and this was treated by refinement of two or three ideal rigid body models at each location. Occupancy factors were estimated based on comparison of isotropic displacement parameters. The structure of the composition as determined by the crystal analysis is shown in FIG. 23.

TABLE XVI

Crystal Data and Structure Refinement for
Triethylammonium 3-Fluoro-2,6-bis(4-Trifluoromethylphenyl)Benzoate
(Table 3, Entry 4).

| | |
|---|---|
| Empirical formula | $C_{27}H_{26}F_7NO_2$ |
| Formula weight | 529.49 |
| Temperature | 223(2) K |

TABLE XVI-continued

Crystal Data and Structure Refinement for
Triethylammonium 3-Fluoro-2,6-bis(4-Trifluoromethylphenyl)Benzoate
(Table 3, Entry 4).

| | |
|---|---|
| Wavelength | 0.71073 Å |
| Crystal system, space group Triclinic, | P-1 |
| Unit cell dimensions | a = 9.748(2) Å alpha = 105.117(2). |
| | b = 12.943(2) Å beta = 94.607(3) deg. |
| | c = 20.949(3) Å gamma = 94.565(3) deg. |
| Volume | 2529.5(8) Å$^3$ |
| Z, Calculated density 4, | 1.390 Mg/m$^3$ |
| Absorption coefficient | 0.122 mm$^{-1}$ |
| F(000) | 1096 |
| Crystal size | 0.35 × 0.15 × 0.15 mm |
| Theta range for data collection | 1.64 to 23.54 deg. |
| Limiting indices | −10 <= h <= 10, −14 <= k <= 14, 0 <= l <= 23 |
| Reflections collected/unique | 10955/7424 [R(int) = 0.0394] |
| Completeness to theta = 23.54 | 98.9% |
| Absorption correction Empirical | |
| Max. and min. transmission | 0.9972 and 0.7276 |
| Refinement method Full-matrix least-squares on F$^2$ | |
| Data/restraints/parameters | 2626/11/626 |
| Goodness-of-fit on F$^2$ | 0.912 |
| Final R indices [I > 4sigma(I)] | R1 = 0.0591, wR2 = 0.1471 |
| R indices (all data) | R1 = 0.1606, wR2 = 0.1978 |
| Largest diff. peak and hole | 0.718 and −0.633 e.Å$^{-3}$ |

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

We claim:

1. A method comprising the step of:
contacting one or a plurality of electron-rich, five-membered heterocycles, benzoic acids, and/or phenols with one or a plurality of aryl chlorides in the presence of a palladium catalyst solution for a period of time and at an elevated temperature sufficient to produce arylated heterocyles, benzoic acids, and/or phenols, where the method affords a simpler and faster method for forming complex molecular entities.

2. The method of claim 1, further comprising the step of:
isolating the complex molecular entities and/or purifying the complex molecular entities.

3. The method of claim 1, wherein the palladium catalyst solution includes a palladium catalyst selected from the group consisting of palladium acetate, palladium trifluoroacetate, palladium complexes with dibenzilideneacetone, palladium on carbon and mixtures thereof.

4. The method of claim 3, wherein the palladium catalyst solution further includes a base, a promoter and a solvent.

5. The method of claim 4, wherein the promoter is selected from the group consisting of a bulky, electron-rich phosphine, a secondary phosphine oxide, an N-heterocyclic carbene, and mixtures thereof.

6. The method of claim 5, wherein the bulky, electron-rich, phosphine is selected from the group consisting of butyl-di-1-adamantylphosphine, t-butyldicyclohexylphosphine, methyl-di-t-butylphosphine, and mixtures thereof.

7. The method of claim 4, wherein the inorganic base is compatible with the solvent.

8. The method of claim 7, wherein the base is selected from the group consisting of CsOAc, CsF, K$_3$PO$_4$, K$_2$CO$_3$, Cs$_2$CO$_3$, other carbonates, phosphates, fluorides, and mixtures thereof.

9. The method of claim 8, wherein the base is potassium phosphate, which affords improved selectivity to complex molecular entities comprising monoarylated products.

10. The method of claim 8, wherein the base is potassium phosphate, which affords improved formation of complex molecular entities comprising arylated heterocycles.

11. The method of claim 8, wherein the base is cesium carbonate, which affords improved formation of complex molecular entities comprising arylated benzoic acids and arylated phenols.

12. The method of claim 4, wherein the solvent is selected from the group consisting of N-methylpyrrolidinone, dimethylformamide, toluene, and mixtures thereof.

13. The method of claim 4, wherein the solvent is N-methylpyrrolidinone for heterocycles.

14. The method of claim 4, wherein the solvent is dimethylformamide for benzoic acids and phenols.

15. The method of claim 1, wherein the complex molecular entities include multiple arylated compounds.

16. The method of claim 15, wherein the multiple arylated compounds include between 2 and a maximum number of aryl groups the heterocycle, benzoic acid or phenol can accommodate.

17. The method of claim 15, wherein the multiple arylated products include between 2 and 4 aryl groups.

18. The method of claim 15, wherein the multiple arylated products include between 2 and 3 aryl groups.

19. The method of claim 15, wherein the multiple arylated products include 2 aryl groups.

20. The method of claim 1, wherein the elevated temperature is between about 90° C. and about 160° C.

21. The method of claim 1, wherein the time is a period between about 30 minutes and about 24 hours.

22. A one-step method comprising the steps of:
contacting one or a plurality of electron-rich, five-membered heterocycles with one or a plurality of aryl chlorides in the presence of a palladium catalyst solution, where the method affords a simpler and faster method for forming complex molecular entities comprising monoarylated products, multiple arylated products or mixtures thereof, and isolating the complex molecular entities and/or purifying the complex molecular entities, where the palladium catalyst solution includes (i) a palladium catalyst selected from the group consisting of palladium acetate, palladium trifluoroacetate, palladium complexes with dibenzilideneacetone, and palladium on carbon and mixtures thereof, (ii) a solvent selected from consisting of dipolar, aprotic solvents, toluene and mixtures thereof, (iii) a promoter selected from the group consisting of a bulky, electron-rich phosphine, a secondary phosphine oxide, an N-heterocyclic carbene, and mixtures thereof; (iv) an inorganic base compatible with the solvent and (v) a molecular sieve.

23. The method of claim 22, wherein the contacting occurs at a time and at an elevated temperature.

24. A one-step method comprising the steps of:

contacting one or a plurality of benzoic acids with one or a plurality of aryl chlorides in the presence of a palladium catalyst solution, where the method affords a simpler and faster method for forming complex molecular entities comprising monoarylated products, multiple arylated products or mixtures thereof; and isolating the complex molecular entities and/or purifying the complex molecular entities, where the palladium catalyst solution includes (i) a palladium catalyst is selected from the group consisting of palladium acetate, palladium trifluoroacetate, palladium complexes with dibenzilideneacetone, and palladium on carbon and mixtures thereof, (ii) a solvent selected from consisting of dipolar, aprotic solvents, toluene and mixtures or, (iii) a promoter selected from the group consisting of a bulky, electron-rich phosphine, a secondary phosphine oxide, an N-heterocyclic carbene, and mixtures thereof; (iv) an inorganic base compatible with the solvent and (v) a molecular sieve.

25. The method of claim 24, wherein the contacting occurs at a time and at an elevated temperature.

26. A one-step method comprising the steps of:

contacting one or a plurality of phenols with one or a plurality of aryl chlorides in the presence of a palladium catalyst solution, where the method affords a simpler and faster method for forming complex molecular entities comprising monoarylated products, multiple arylated products or mixtures thereof, and isolating the complex molecular entities and/or purifying the complex molecular entities, where the palladium catalyst solution includes (i) a palladium catalyst selected from the group consisting of palladium acetate, palladium trifluoroacetate, palladium complexes with dibenzilideneacetone, and palladium on carbon and mixtures thereof, (ii) a solvent selected from the group consisting of dipolar, aprotic solvents, toluene and mixtures thereof, (ii) a promoter selected from the group consisting of a bulky, electron-rich phosphine, a secondary phosphine oxide, an N-heterocyclic carbene, and mixtures thereof; (iii) an inorganic base compatible with the solvent and (iv) a molecular sieve.

27. The method of claim 26, wherein the contacting occurs at a time and at an elevated temperature.

28. The method of claim 4, wherein the solvent is selected from the group consisting of dipolar, aprotic solvents, toluene and mixtures thereof.

* * * * *